(12) United States Patent
Corson et al.

(10) Patent No.: US 10,143,692 B2
(45) Date of Patent: *Dec. 4, 2018

(54) POLYMORPHS OF ARRY-380, A SELECTIVE HER2 INHIBITOR AND PHARMACEUTICAL COMPOSITIONS CONTAINING THEM

(71) Applicant: Array BioPharma Inc., Boulder, CO (US)

(72) Inventors: Donald T. Corson, Boulder, CO (US); Christopher M. Lindemann, Fort Collins, CO (US); Daniel J. Watson, Lafayette, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,444

(22) Filed: Jan. 3, 2018

(65) Prior Publication Data
US 2018/0140603 A1 May 24, 2018

Related U.S. Application Data

(63) Continuation of application No. 14/923,172, filed on Oct. 26, 2015, now Pat. No. 9,889,134, which is a continuation of application No. 14/351,835, filed as application No. PCT/US2012/060138 on Oct. 12, 2012, now Pat. No. 9,168,254.

(60) Provisional application No. 61/606,185, filed on Mar. 2, 2012, provisional application No. 61/547,615, filed on Oct. 14, 2011.

(51) Int. Cl.
| C07D 471/04 | (2006.01) |
| A61K 31/437 | (2006.01) |
| A61K 31/517 | (2006.01) |
| A61P 35/00 | (2006.01) |
| A61K 45/06 | (2006.01) |

(52) U.S. Cl.
CPC .......... *A61K 31/517* (2013.01); *A61K 31/437* (2013.01); *A61K 45/06* (2013.01); *A61P 35/00* (2018.01); *C07D 471/04* (2013.01)

(58) Field of Classification Search
CPC ............................ C07D 471/04; A61K 31/437
USPC .................... 544/283, 284; 514/266.1, 266.2
See application file for complete search history.

(56) References Cited

U.S. PATENT DOCUMENTS

| 8,648,087 | B2 |  | 2/2014 | Lyssikatos et al. | |
| 9,168,254 | B2 | * | 10/2015 | Corson | C07D 471/04 |
| 9,457,093 | B2 |  | 10/2016 | Fry et al. | |
| 9,676,791 | B2 |  | 6/2017 | Wallace et al. | |
| 9,693,989 | B2 |  | 7/2017 | Lyssikatos et al. | |
| 9,889,134 | B2 | * | 2/2018 | Corson | A61K 31/517 |

| 2014/0023643 | A1 | 1/2014 | Lyssikatos et al. |
| 2014/0296267 | A1 | 10/2014 | Fry et al. |
| 2015/0110780 | A1 | 4/2015 | Lee et al. |
| 2017/0136022 | A1 | 5/2017 | Fry et al. |
| 2017/0252317 | A1 | 9/2017 | Lyssikatos et al. |
| 2017/0260202 | A1 | 9/2017 | Wallace et al. |

FOREIGN PATENT DOCUMENTS

| WO | 2003077914 A1 | 9/2003 |
| WO | 2005026151 A1 | 3/2005 |
| WO | 2005026152 A1 | 3/2005 |
| WO | 2007059257 A2 | 5/2007 |

OTHER PUBLICATIONS

U.S. Appl. No. 10/642,440, U.S. Pat. No. 7,501,427.
U.S. Appl. No. 12/081,725, U.S. Pat. No. 7,585,975.
U.S. Appl. No. 12/496,973, U.S. Pat. No. 7,777,032.
U.S. Appl. No. 10/914,974, U.S. Pat. No. 7,452,895.
U.S. Appl. No. 12/249,421, U.S. Pat. No. 8,278,314.
U.S. Appl. No. 13/607,016, U.S. Pat. No. 9,676,791.
U.S. Appl. No. 15/606,928, 2017-0260202.
U.S. Appl. No. 12/085,048, U.S. Pat. No. 8,648,087.
U.S. Appl. No. 14/034,361, U.S. Pat. No. 9,693,989.
U.S. Appl. No. 15/599,867, 2017-0252317.
U.S. Appl. No. 14/351,840, U.S. Pat. No. 9,457,093.
U.S. Appl. No. 15/275,163, 2017-0136022.
U.S. Appl. No. 14/387,533, 2015-0110780.
U.S. Appl. No. 14/351,835, U.S. Pat. No. 9,168,254.
U.S. Appl. No. 14/923,172, U.S. Pat. No. 9,889,134.
"Cecil Textbook of Medicine", edited by Bennet, J.C. and Plum F., 20th edition, vol. 1, 1004-1010 (2004).
Ashizawa, et al., "Iyakuhin no takei genshou to shouseki no kagaku", Science of Polymorphism and Crystallization of Pharmaceuticals, 272-317 (2002) [Non-English Document.].
Brittain, "Polymorphism in Pharmaceutical Solids", New York, NY, Marcel Dekker, Inc.; pp. 1-4, 15-19 and 318-427 (1999).
Caira, et al., "Crystalline Polymorphism of Organic Compounds", Topics in Current Chemistry, vol. 198, 163-208 (1998).
Chmielecki, et al., "Oncogenic Alterations in ERBB2/HER2 Represent Potential Therapeutic Targets Across Tumors From Diverse Anatomic Sites of Origin", The Oncologist 20, 7-12 (2015).
Clinical Trials (PDQ®), "Paclitaxel, and Carboplatin With or Without Trastuzumab in Treating Patients With Esophageal Cancer", National Cancer Institute, http://www.cancergov/clinicaltrials/search/view?cdrid=683717&version=HealthProfessional&protocolsearchid=6183056, 33 pages, Jan. 22, 2015.
Clinical Trials (PDQ®), "Study of Herceptin (Trastuzumab) in Combination With Cisplatin/Capecitabine Chemotherapy in Patients With HER2-Positive Metastatic Gastric or Gastro-Esophageal Junction Cancer", National Cancer Institute, HELOISE Study, http://www.cancer.gov/clinicaltrials/search/view?cdrid=714394&version=HealthProfessional&protocolsearchid=6183056, 9 pages, Jan. 22, 2015.

(Continued)

*Primary Examiner* — Venkataraman Balasubramanian
(74) *Attorney, Agent, or Firm* — Viksnins Harris Padys Malen LLP; Corey M. Williams

(57) ABSTRACT

Polymorphs of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine are provided herein. Processes for preparing the polymorphs and pharmaceutical composition comprising the polymorphs are also disclosed.

36 Claims, 58 Drawing Sheets

(56) References Cited

OTHER PUBLICATIONS

Clinical Trials (PDQ®), "Trastuzumab in Treating Patients with Metastatic Pancreatic Cancer That Progressed After Previous Treatment with Gemcitabine", National Cancer Institute, http://www.cancer.gov/clinicaltrials/search/view?cdrid=636018&version=HealthProfessional&protocolsearchid=6183056, 4 pages, Oct. 20, 2014.

Dermer, "Another Anniversary for the War on Cancer", Bio/Technology 12, 320 (1994).

Erjala, et al "Signaling via ErbB2 and ErbB3 Associates with Resistance and Epidermal Growth Factor Receptor (EGFR) Amplification with Sensitivity to EGFR Inhibitor Gefitinib in Head and Neck Squamous Cell Carcinoma Cells", Clinical Cancer Res 12 (13), 4103-4111 (2006).

Fabbro, et al., "Protein kinases as targets for anticancer agents: from inhibitors to useful drugs", Pharmacology & Therapeutics 93, 79-98 (2002).

Freshney, et al., "Culture of Animal Cells, A Manual of Basic Technique", Alan R. Liss, Inc., New York, p. 4, (1983).

Golub, et al., "Molecular Classification of Cancer: Class Discovery and Clas Prediction by Gene Expression Monitoring", Science 286, 531-537 (1999).

Herceptin®, [trastuzumab], Full Prescribing Information, http://www.gene.com/download/pdf/herceptin_prescribing.pdf, 35 pages, Jun. 2014.

Hirayama, "Yuuki kagoubutsu kesshou sakusei handbook", Handbook for Making Organic Compound Crystals, 57-84 (2008) [Non-English Document.].

Hynes, et al., "ErbB receptors and signaling pathways in cancer", Current Opinion in Cell Biology 21, 177-184 (2009).

Japanese Office Action, for corresponding JP Application No. 2015-237564, 9 pages, dated Jun. 30, 2017.

Koch, "Arry 380: A Selective, Oral HER2 Inhibitor for the Treatment of Solid Tumors", American Association of Cancer Research 102nd Annual Meeting, 29 pages, Apr. 3, 2011.

Lindemann, et al., "Amorphous Dispersion Development of ARRY-380, an ErbB2 Selective Inhibitor", American Association of Pharmaceutical Scientists, Annual Meeting and Exposition. Oct. 17, 2012.

Lindemann, et al., "Solid-State Characterization of Seven Isomorphic Solvates of ARRY-380", Full Poster along with enlarged sections of full poster, American Association of Pharmaceutical Scientists, Annual Meeting and Exposition, 5 pages, Oct. 17, 2012.

Mass, "The HER Receptior Family: A Rich Target for Therapeutic Development", Int J Radiation Oncology Bio Phys. vol. 58(3), 932-940 (2004).

Melisko, et al., "New Challenges and opportunities in the management of brain metastases in patients with ErbB2-positive metastatic breast cancer", Nature Clinical Practice Oncology, vol. 6 (1), 25-33 (2009).

Office Action, issued in corresponding Colombian Application No. 14-103.945, 14 pages, dated Jun. 19, 2015.

Patent Cooperation Treaty, International Searching Authority, Search Report and Written Opinion for PCT/US2012/060138, 10 pages, dated Feb. 5, 2013.

Roskoski, "The ErbB/HER family of protein-tyrosine kinases and cancer", Pharmacological Research 79, 34-74 (2014).

* cited by examiner

POLYMORPHS OF ARRY-380, A SELECTIVE HER2 INHIBITOR AND PHARMACEUTICAL COMPOSITIONS CONTAINING THEM

CROSS-REFERENCE TO RELATED APPLICATIONS

This application is a Continuation of U.S. application Ser. No. 14/923,172, filed Oct. 26, 2015, which is a Continuation of U.S. application Ser. No. 14/351,835, filed Apr. 14, 2014, now U.S. Pat. No. 9,168,254, which is a 35 U.S.C. § 371 application of PCT/US2012/060138, filed Oct. 12, 2012, which claims priority to U.S. Provisional Application No. 61/606,185, filed Mar. 2, 2012 and 61/547,615, filed Oct. 14, 2011. The entire content of these applications is hereby incorporated herein by reference.

FIELD OF THE INVENTION

Polymorphs of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine are provided herein. Also, pharmaceutical compositions comprising polymorphs of N4-(4-([1,2,4]triazolo[1,5-a]pyridin-7-yloxy)-3-methylphenyl)-N6-(4,4-dimethyl-4,5-dihydrooxazol-2-yl)quinazoline-4, 6-diamine and processes for preparing the polymorphs are provided herein.

DESCRIPTION OF THE STATE OF THE ART

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine (also called "ARRY-380"), which has the structure:

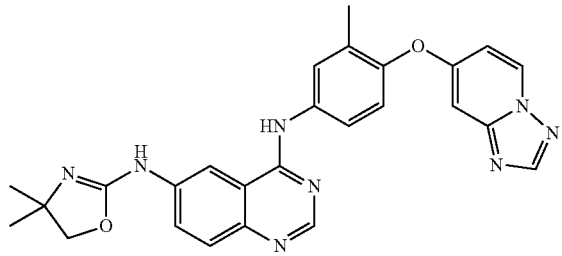 [SMILES: Cc1cc(Nc2ncnc3ccc(NC4=NC(C)(C)CO4)cc23)ccc1Oc1ccn2ncnc2c1]

is a selective ErbB2 (HER2) inhibitor described in WO 2007/059257, which is incorporated by reference in its entirety. N4-(4-([1,2,4]Triazolo[1,5-a]pyridin-7-yloxy)-3-methylphenyl)-N6-(4,4-dimethyl-4,5-dihydrooxazol-2-yl) quinazoline-4,6-diamine has been tested in human clinical trials for hyperproliferative diseases, particularly cancer (see Koch, Kevin. "ARRY-380: A Selective, Oral HER2 Inhibitor for the Treatment of Solid Tumors." American Association of Cancer Research 102nd Annual Meeting, Apr. 3, 2011; which may also be found at: http://www.arraybiopharma.com/_documents/Publication/PubAttachment462.pdf).

Polymorphism is the occurrence of different crystalline forms of a single compound and it is a property of some compounds and complexes. Thus, polymorphs are distinct solids sharing the same molecular formula, yet each polymorph may have distinct solid state physical properties. Therefore, a single compound may give rise to a variety of polymorphic forms where each form has different and distinct solid state physical properties, such as different solubility profiles, melting point temperatures, flowability, dissolution rates and/or different X-ray diffraction peaks. These practical physical characteristics are influenced by the conformation and orientation of molecules in the unit cell, which defines a particular polymorphic form of a substance. Due to the possibility of variable solubility of each polymorph, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy, such as X-ray powder diffraction ("XRPD"), and by other methods, such as infrared spectrometry. Additionally, polymorphic forms of the same drug substance or active pharmaceutical ingredient can be administered by itself or formulated as a drug product (pharmaceutical composition) and are well known in the pharmaceutical art to affect, for example, the solubility, stability, flowability, tractability and compressibility of drug substances and the safety and efficacy of drug products. For more, see Hilfiker, Rolf (ed.), *Polymorphism in the Pharmaceutical Industry*. Weinheim, Germany: Wiley-VCH 2006.

The discovery of new polymorphic forms of a pharmaceutically useful compound provides a new opportunity to improve the performance characteristics of a pharmaceutical product. It has now been surprisingly found that new crystalline forms of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine exist.

SUMMARY OF THE INVENTION

Polymorphic forms of N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine are described herein, including Forms A, B, C, D, E, F, G, H, I, J, K, L, M, N, O and P. Additionally, amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine is described herein. Accordingly, the compounds are useful in the treatment of hyperproliferative diseases, such as cancer.

Another aspect provides methods of preventing or treating a disease or disorder modulated by ErbB2, comprising administering to a mammal in need of such treatment an effective amount of a compound described herein.

Another aspect provides methods of preventing or treating cancer, comprising administering to a mammal in need of such treatment an effective amount of a compound described herein, alone or in combination with one or more additional compounds having anti-cancer properties.

Another aspect provides a method of treating a hyperproliferative disease in a mammal comprising administering a therapeutically effective amount of a compound described herein to the mammal.

Another aspect provides the use of a compound of this invention in the manufacture of a medicament for the treatment of a hyperproliferative disease.

Another aspect provides compounds described herein for use in the treatment of cancer.

Another aspect provides a pharmaceutical composition comprising a compound described herein, and a pharmaceutically acceptable carrier or excipient.

Another aspect provides processes for preparing compounds described herein.

DETAILED DESCRIPTION OF THE INVENTION

Figure 1:
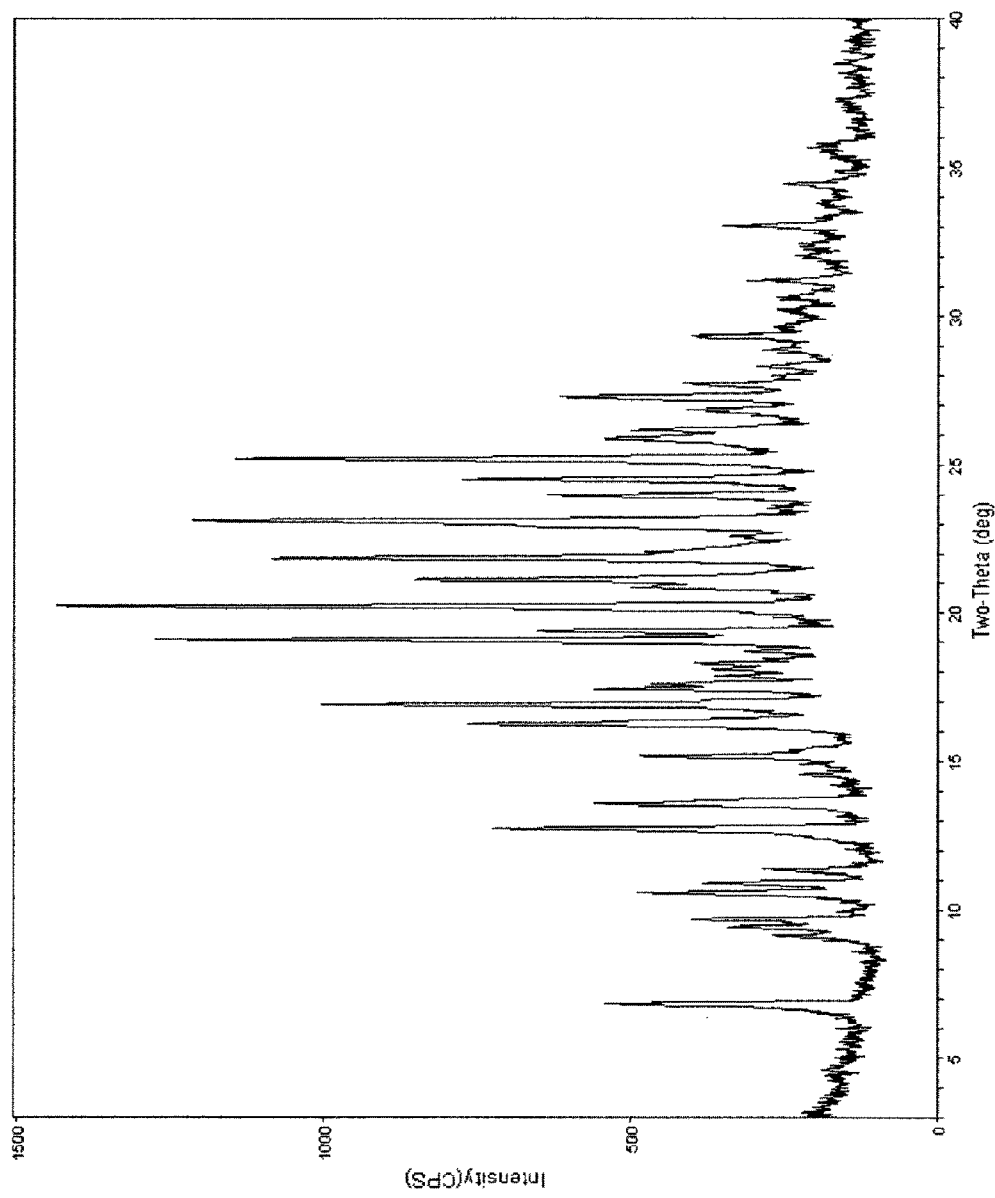
FIG. 1 shows a characteristic XRPD scan of Form A.

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

Some alkyl moieties have been abbreviated, for example, methyl ("Me") and ethyl ("Et"). The abbreviations are sometimes used in conjunction with elemental abbreviations and chemical structures, for example, methanol ("MeOH") or ethanol ("EtOH"). Additional abbreviations used throughout the application may include, for example, acetate ("Ac"), acetonitrile ("ACN"), dichloromethane ("DCM"), dimethoxyethane ("DME"), ethyl acetate ("EtOAc"), isopropyl alcohol ("IPA"), methyl acetate ("MeOAc"), methyl isobutyl ketone ("MIBK"), methyl tert-butyl ether ("MTBE"), sodium carboxymethyl cellulose ("NaCMC") and tetrahydrofuran ("THF").

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. In regard to 2θ degrees, the term about means±0.2 degrees for polymorphs and ±0.6 degrees for isomorphic polymorphs, unless stated otherwise.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, brain, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The term "mammal" means a warm-blooded animal that has or is at risk of developing a disease described herein and includes, but is not limited to, guinea pigs, dogs, cats, rats, mice, hamsters, and primates, including humans.

The phrase "pharmaceutically acceptable" indicates that the substance or composition is compatible chemically and/or toxicologically, with the other ingredients comprising a formulation, and/or the mammal being treated therewith.

The phrase "substantially pure" means the polymorphic form or amorphous material includes less than about 15% by weight of impurities, including other polymorphic forms. In certain embodiments, the substantially pure polymorphic form or amorphous material includes less than about 10% by weight of impurities, including other polymorphic forms. In certain embodiments, the substantially pure polymorphic form or amorphous material includes less than about 5% by weight of impurities, including other polymorphic forms. In certain embodiments, the substantially pure polymorphic form or amorphous material includes less than about 1% by weight of impurities, including other polymorphic forms.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

Polymorphs

Provided herein are polymorphs of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine freebase, designated Forms A, B, C, D, E, F, G, H, I, J, K, L, M, N, O and P. Also, provided herein is amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine. Processes for preparing the polymorphs, and pharmaceutical compositions thereof that are potentially useful in the treatment of diseases, conditions and/or disorders modulated by ErbB2 are also provided.

Many of the polymorphs described herein are solvates. However, some of the polymorphs are not solvates, but exist, for example, as anhydrous forms. Also, some of the polymorphs are isomorphic solvate polymorphs (or solvatomorph), which crystallize in the same space group with slight variation of cell parameters and comprise chemically related structures but different elemental composition. In this case, the variation in chemical composition among the isomorphs arises from incorporation of different water/solvent molecules. Consequently, the isomorphs display similar but non-identical XRPD patterns. For more information on isomorphic polymorphs, see Hilfiker, supra.

Form A

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A is provided. In certain embodiments, a substantially pure crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form A is provided. Form A can be distinguished by the XRPD diffraction in FIG. 1 and/or peak assignments of the XRPD diffraction of FIG. 1 in Table 1.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A, characterized by at least one specific XRPD diffraction peak at about (2θdegrees±0.2) 20.3 is provided. In a further embodiment, a crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form A, characterized by at least one specific XRPD diffraction peak at about (2θdegrees±0.2) 20.278 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A, characterized by XRPD diffraction peaks at about (2θdegrees±0.2) 19.1, 20.3, 21.9, 23.1 and 25.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline- 4,6-diamine Form A, characterized by XRPD diffraction peaks at about (2θdegrees±0.2) 19.138, 20.278, 21.863, 23.139 and 25.202 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A, characterized by XRPD diffraction peaks at about (2θdegrees±0.2) 16.9, 19.1, 20.3, 21.1, 21.9, 23.1 and 25.2 is provided. In a further embodiment, a crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form A, characterized by XRPD diffraction peaks at about (2θdegrees±0.2) 16.94, 19.138, 20.278, 21.16, 21.863, 23.139 and 25.202 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A, characterized by XRPD diffraction peaks at about (2θdegrees±0.2) 12.8, 13.6, 16.3, 16.9, 19.1, 19.4, 20.3, 21.1, 21.9, 23.1, 24.5 and 25.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A, characterized by XRPD diffraction peaks at about (2θdegrees±0.2) 12.78, 13.637, 16.3, 16.94, 19.138, 19.44, 20.278, 21.16, 21.863, 23.139, 24.519 and 25.202 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A which has an XRPD diffraction pattern substantially the same as FIG. 1 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A which is characterized by XRPD diffraction peaks (2θdegrees±0.2) substantially the same as Table 1 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A which is characterized by endotherms at about 203.7° C. and 240.0° C. is provided.

Figure 31:
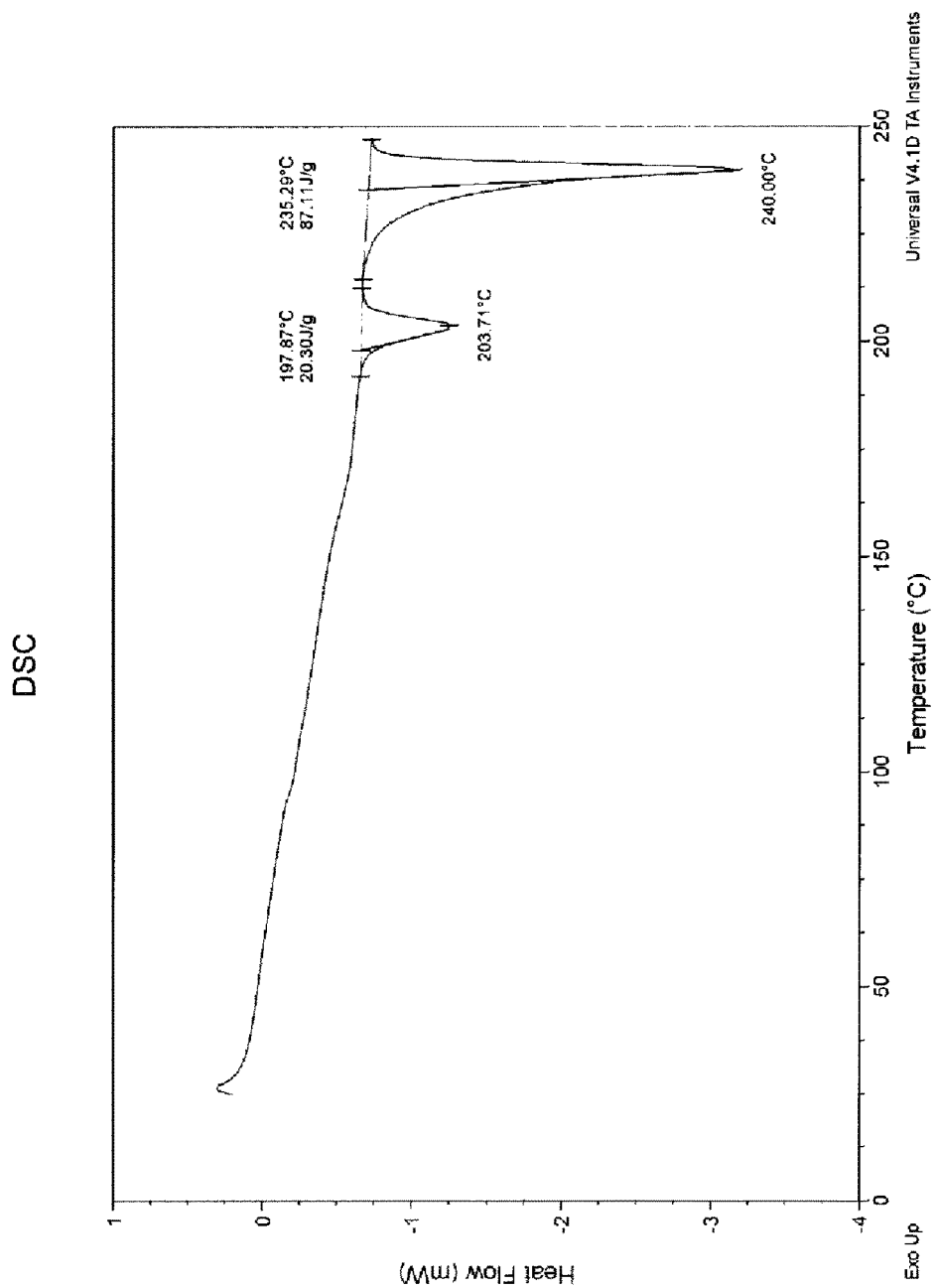
FIG. 31 shows a characteristic differential scanning calorimetry ("DSC") scan of Form A.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A which is characterized by a DSC scan substantially the same as FIG. 31 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A comprising:

(a) mixing amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine and 1:1 EtOH:water; and (b) recrystallizing the solid to prepare Form A.

In certain embodiments, the mixture in Step (a) is heated. In a further embodiment, the mixture in Step (a) is heated to about 50° C.

Form B

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B is provided. In certain embodiments, a substantially pure crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B is provided. Form B forms isomorphic solvates. Form B can be distinguished by the representative XRPD diffraction in FIGS. 2 to 9 and/or representative peak assignments of the XRPD diffraction of FIGS. 2 to 9 in Tables 2 to 9.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B, characterized by XRPD diffraction peaks at about (2θdegrees±0.3) 9.9 and 25.5 is provided. In certain embodiments, a crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B, characterized by XRPD diffraction peaks at about (2θdegrees±0.2) 9.9 and 25.5 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B, characterized by XRPD diffraction peaks at about (2θdegrees±0.3) 9.9, 16.9, 18.0, 20.7 and 25.5 is provided. In certain embodiments, a crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B, characterized by XRPD diffraction peaks at about (2θdegrees±0.2) 9.9, 16.9, 18.0, 20.7 and 25.5 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B, characterized by XRPD diffraction peaks at about (2θdegrees±0.3) 8.4, 9.9, 13.4, 16.9, 18.0, 20.7, 21.2, 24.7 and 25.5 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B, characterized by XRPD diffraction peaks at about (2θdegrees±0.2) 8.4, 9.9, 16.9, 18.0, 20.7, 21.2 and 25.5 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B comprising:

(a1) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E with a solvent selected from MeOH, or (a2) mixing amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine and a solvent selected from MeOH, acetone and DCM, or (a3) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C/G mixture with a solvent selected from EtOH, or (a4) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A with a solvent selected from IPA, (b) creating a solution with the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and the solvent, and (c) recrystallizing the solid to prepare Form B; or (d1) mixing either N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and ACN, or (d2) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran and THF, and (e) recrystallizing the solid to prepare Form B; or (f) heating N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, and (g) recovering the solid to prepare Form B.

In certain embodiments, the solution in Step (b) is created by heating the mixture of Step (a2) or (a4) to reflux.

In certain embodiments, the solution in Step (b) is created by using EtOH as the solvent and heating the mixture of Step (a3) to about 70° C.

In certain embodiments, the heating in Step (f) is done at about 100 to about 200° C.

In certain embodiments, the solvent in Step (a2) is selected from acetone and DCM In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (d1).

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol is provided. Form B Methanol can be distinguished by the XRPD diffraction in FIG. 2 and/or peak assignments of the XRPD diffraction of FIG. 2 in Table 2.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by at least one specific XRPD diffraction peak at about (2θdegrees±0.2) 10.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by at least one specific XRPD diffraction peak at about (2θdegrees±0.2) 9.98 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by XRPD diffraction peaks at about (2θdegrees±0.2) 8.5, 10.0, 13.4, 17.0 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by XRPD diffraction peaks at about (2θdegrees±0.2) 8.46, 9.98, 13.438, 16.981 and 25.519 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by XRPD diffraction peaks at about (2θdegrees±0.2) 8.5, 10.0, 13.4, 17.0, 18.0, 20.8, 24.7 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by XRPD diffraction peaks at about (2θdegrees±0.2) 8.46, 9.98, 13.438, 16.981, 18.042, 20.799, 24.72 and 25.519 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol, characterized by XRPD diffraction peaks at about (2θdegrees±0.2) 8.5, 10.0, 13.4, 15.8, 17.0, 18.0, 19.7, 20.8, 21.1, 21.6, 23.2, 24.7 and 25.5 is provided. In a further embodiment, a crystalline polymorph N4-(4-([1,2,4]triazolo[1,5-c]pyridin-7-yl oxy)-3-methylphenyl)-N6-(4,4-dimethyl-4,5-dihydrooxazol-2-yl)quinazoline-4,6-diamine Form B Methanol, characterized by XRPD diffraction peaks at about (2θdegrees±0.2) 8.46, 9.98, 13.438, 15.802, 16.981, 18.042, 19.72, 20.799, 21.143, 21.622, 23.161, 24.72 and 25.519 is provided.

Figure 2:
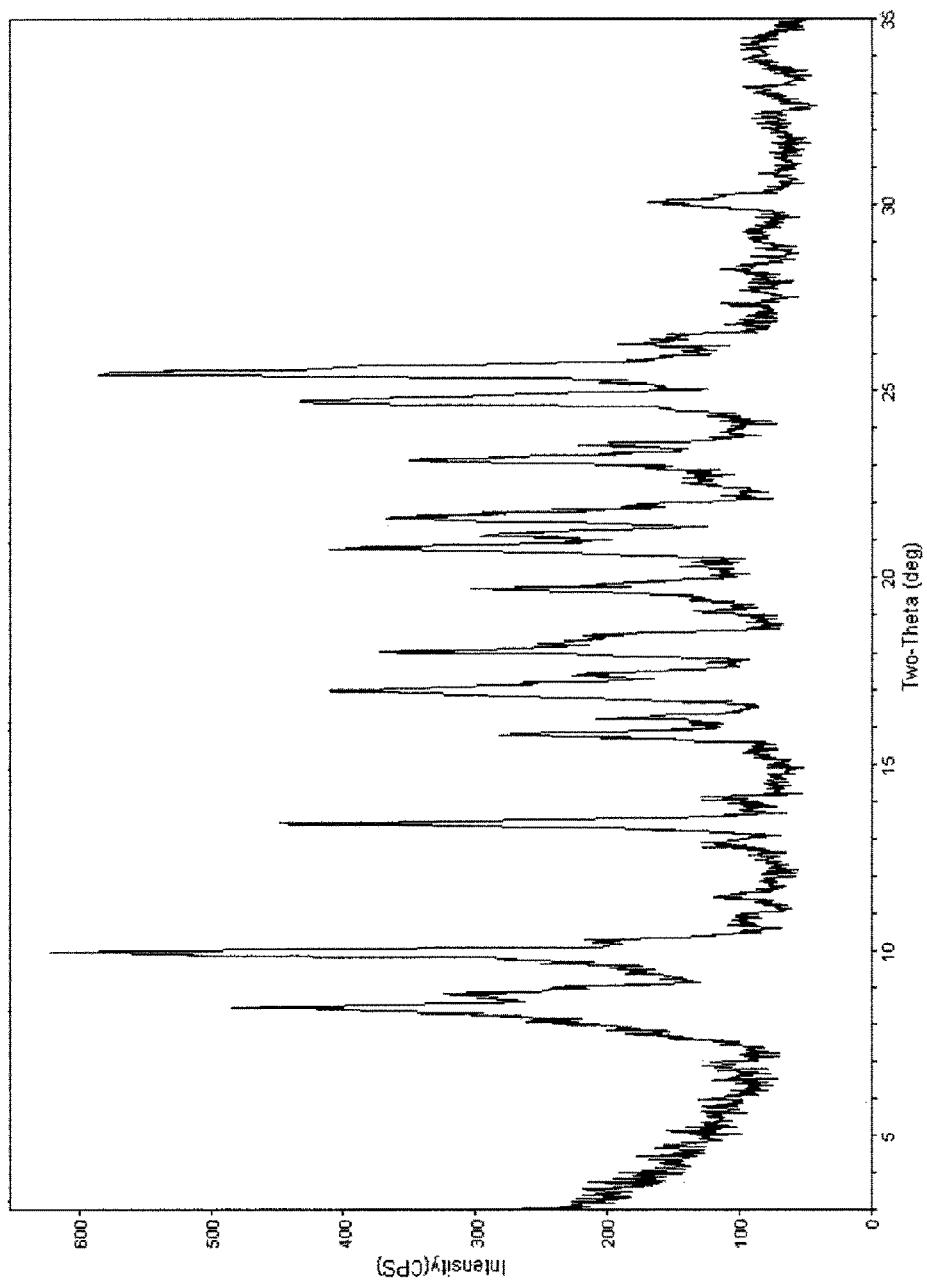
FIG. 2 shows a characteristic XRPD scan of Form B Methanol.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol which has an XRPD diffraction pattern substantially the same as FIG. 2 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol which is characterized by XRPD diffraction peaks (2θdegrees±0.2) substantially the same as Table 2 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol which is characterized by an endotherm at about 226.8° C. is provided.

Figure 32:
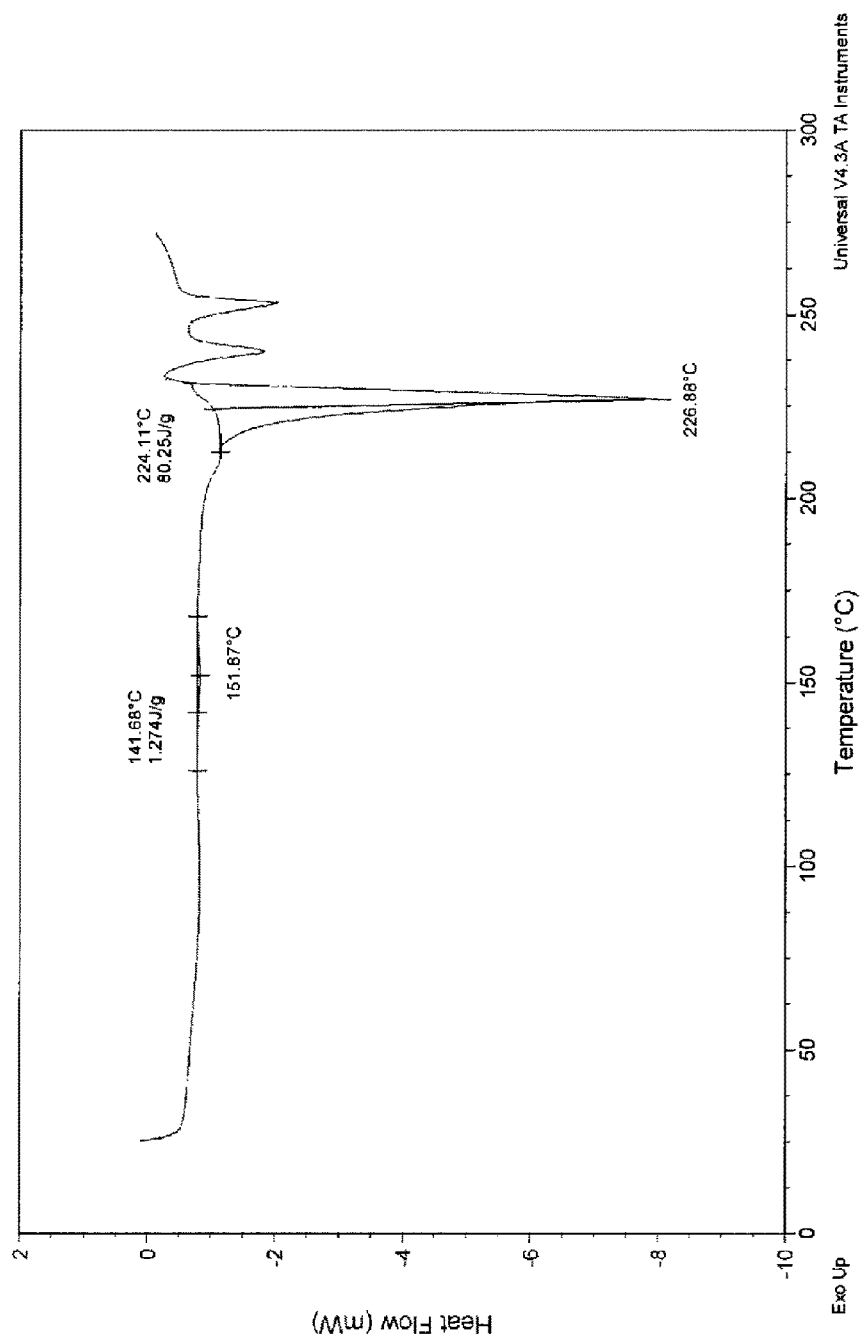
FIG. 32 shows a characteristic DSC scan of Form B Methanol.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol which is characterized by a DSC scan substantially the same as FIG. 32 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Methanol comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine with MeOH;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and MeOH; and (c) recrystallizing the solid to prepare Form B Methanol.

In certain embodiments, the solution in Step (b) is created by heating the mixture of Step (a) to reflux.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol is provided. Form B Ethanol can be distinguished by the XRPD diffraction in FIG. 3 and/or peak assignments of the XRPD diffraction of FIG. 3 in Table 3.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, characterized by at least one specific XRPD diffraction peak at about (2θdegrees±0.2) 25.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, characterized by at least one specific XRPD diffraction peak at about (2θdegrees±0.2) 25.4 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, characterized by XRPD diffraction peaks at about (2θdegrees±0.2) 9.9, 13.3, 20.7, 24.6 and 25.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, characterized by XRPD diffraction peaks at about (2θdegrees±0.2) 9.859, 13.3, 20.718, 24.621 and 25.419 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, characterized by XRPD diffraction peaks at about (2θdegrees±0.2) 9.9, 13.3, 16.9, 17.9, 19.6, 20.7, 21.5, 23.1, 24.6 and 25.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol, characterized by XRPD diffraction peaks at about (2θdegrees±0.2) 9.859, 13.3, 16.862, 17.94, 19.602, 20.718, 21.502, 23.08, 24.621 and 25.419 is provided.

Figure 3:
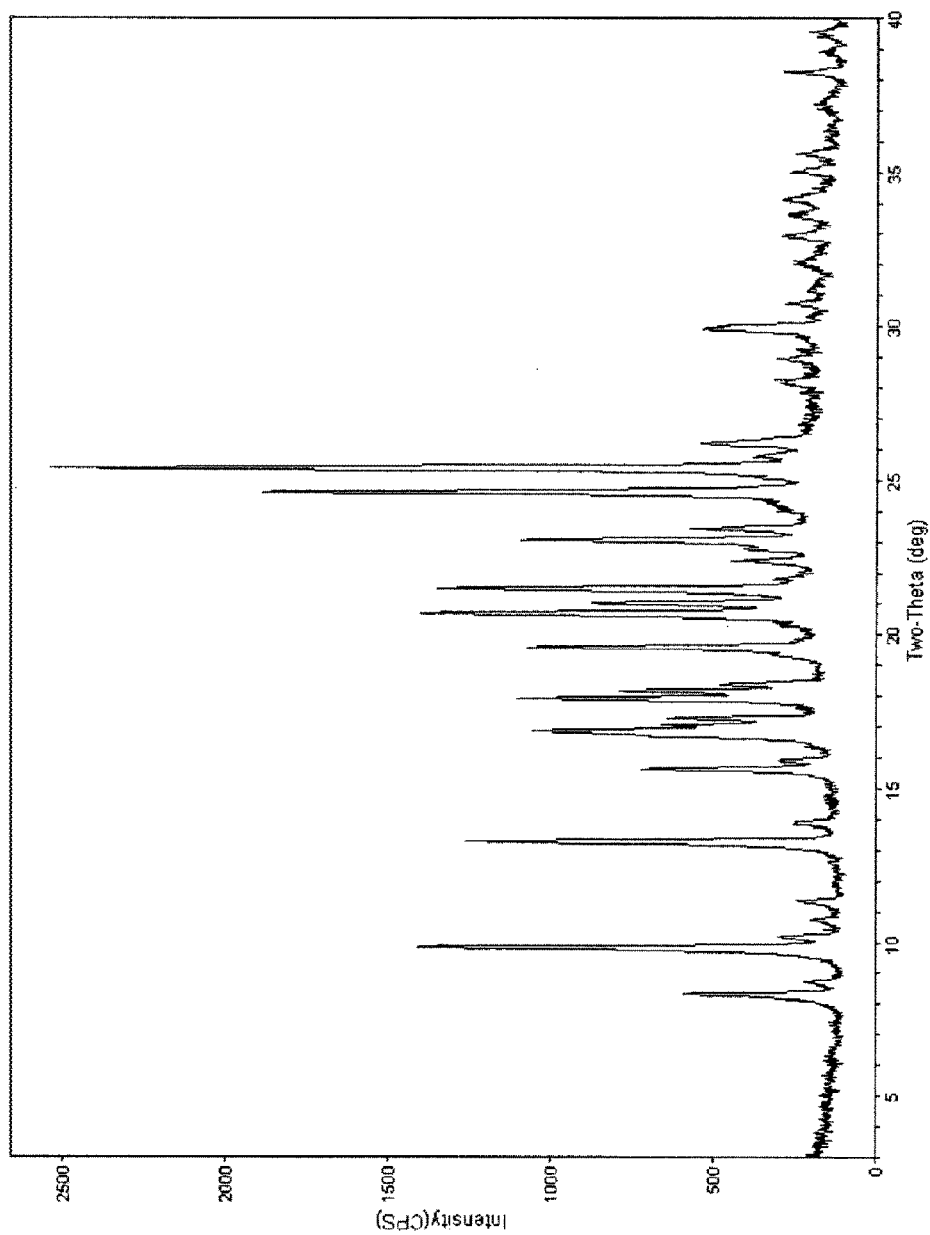
FIG. 3 shows a characteristic XRPD scan of Form B Ethanol.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol which has an XRPD diffraction pattern substantially the same as FIG. 3 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol which is characterized by XRPD diffraction peaks (2θdegrees±0.2) substantially the same as Table 3 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol which is characterized by an endotherm at about 224.8° C. is provided.

Figure 33:
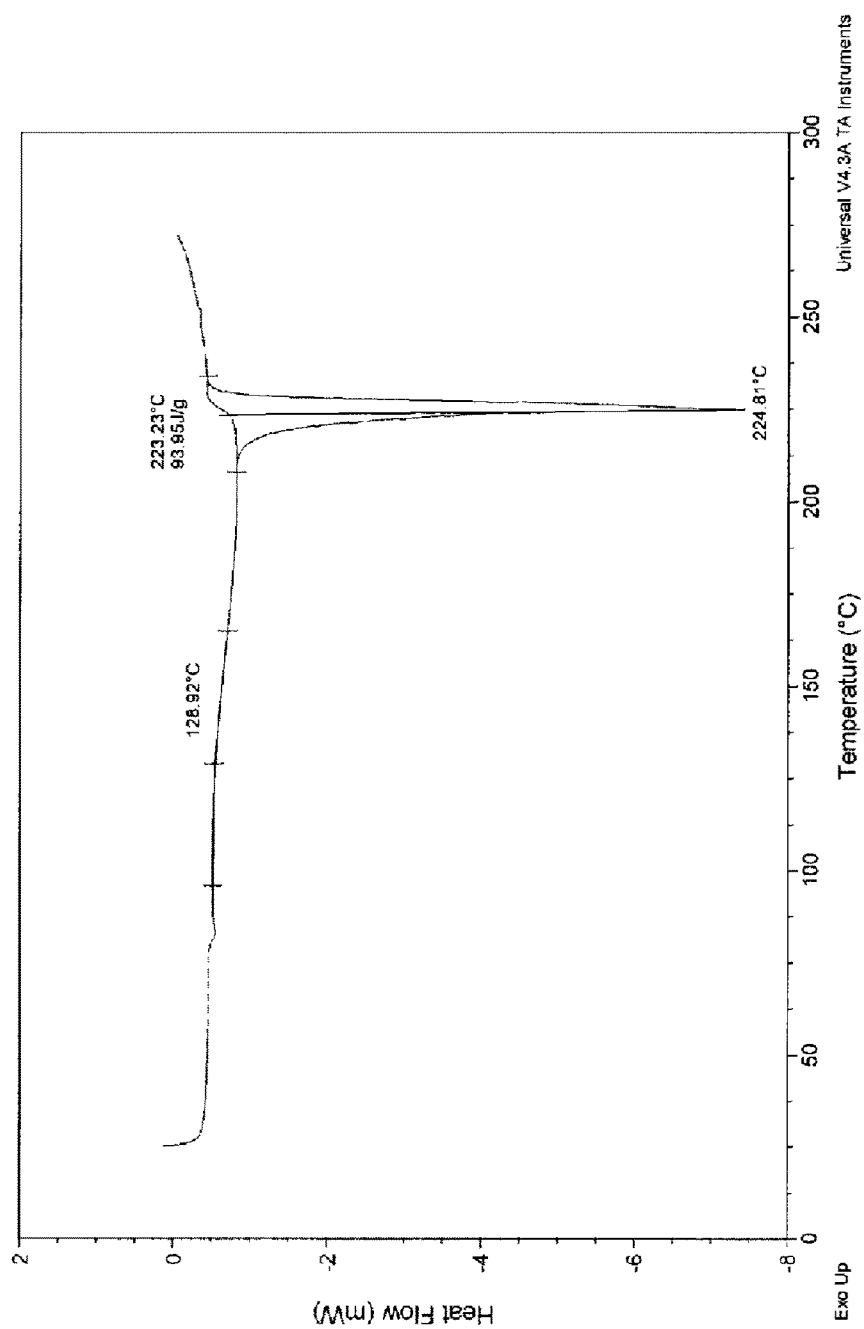
FIG. 33 shows a characteristic DSC scan of Form B Ethanol.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol which is characterized by a DSC scan substantially the same as FIG. 33 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form C/G mixture with EtOH;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and EtOH; and (c) recrystallizing the solid to prepare Form B Ethanol.

In certain embodiments, the solution in Step (b) is created by heating the mixture of Step (a) to about 70° C.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol is provided. Form B Isopropyl Alcohol can be distinguished by the XRPD diffraction in FIG. 4 and/or peak assignments of the XRPD diffraction of FIG. 4 in Table 4.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by at least one specific XRPD diffraction peak at about (2θdegrees±0.2) 16.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by at least one specific XRPD diffraction peak at about (2θdegrees±0.2) 16.88 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by XRPD diffraction peaks at about (2θdegrees±0.2) 9.8, 16.9, 17.9, 20.6 and 25.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by XRPD diffraction peaks at about (2θdegrees±0.2) 9.78, 16.88, 17.899, 20.6 and 25.082 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by XRPD diffraction peaks at about (2θdegrees±0.2) 9.8, 13.2, 16.9, 17.9, 20.6, 25.1 and 25.3 is provided. In a further embodiment, a crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B Isopropyl Alcohol, characterized by XRPD diffraction peaks at about (2θdegrees±0.2) 9.78, 13.201, 16.88, 17.899, 20.6, 25.082 and 25.362 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by XRPD diffraction peaks at about (2θdegrees±0.2) 8.3, 9.8, 13.2, 16.9, 17.9, 20.6, 21.2, 23.0, 24.2, 24.6, 25.1 and 25.3 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol, characterized by XRPD diffraction peaks at about (2θdegrees±0.2) 8.283, 9.78, 13.201, 16.88, 17.899, 20.6, 21.202, 22.981, 24.198, 24.582, 25.082 and 25.362 is provided.

Figure 4:
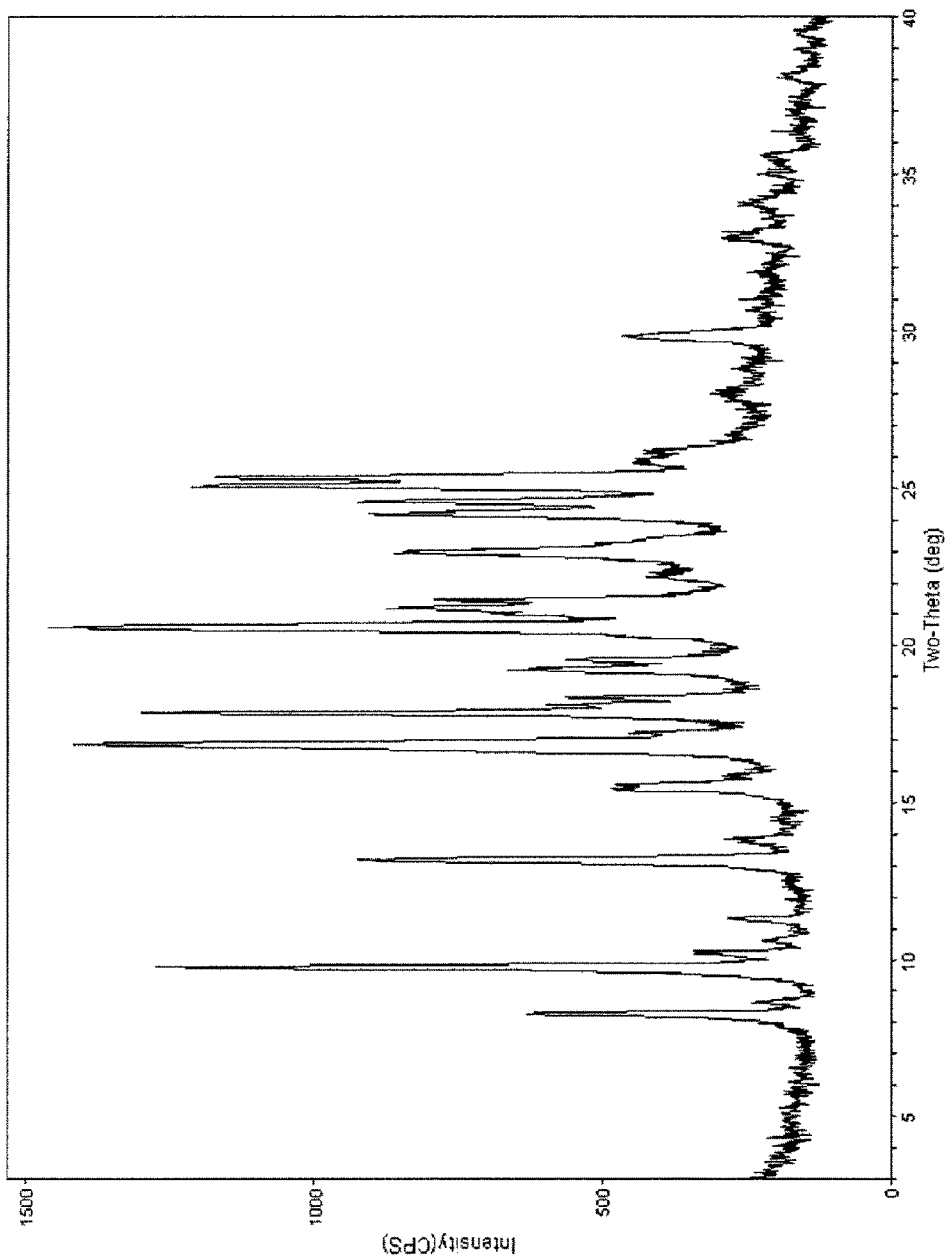
FIG. 4 shows a characteristic XRPD scan of Form B Isopropyl Alcohol.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol which has an XRPD diffraction pattern substantially the same as FIG. 4 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol which is characterized by XRPD diffraction peaks (2θdegrees±0.2) substantially the same as Table 4 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol which is characterized by an endotherm at about 222.3° C. is provided.

Figure 34:
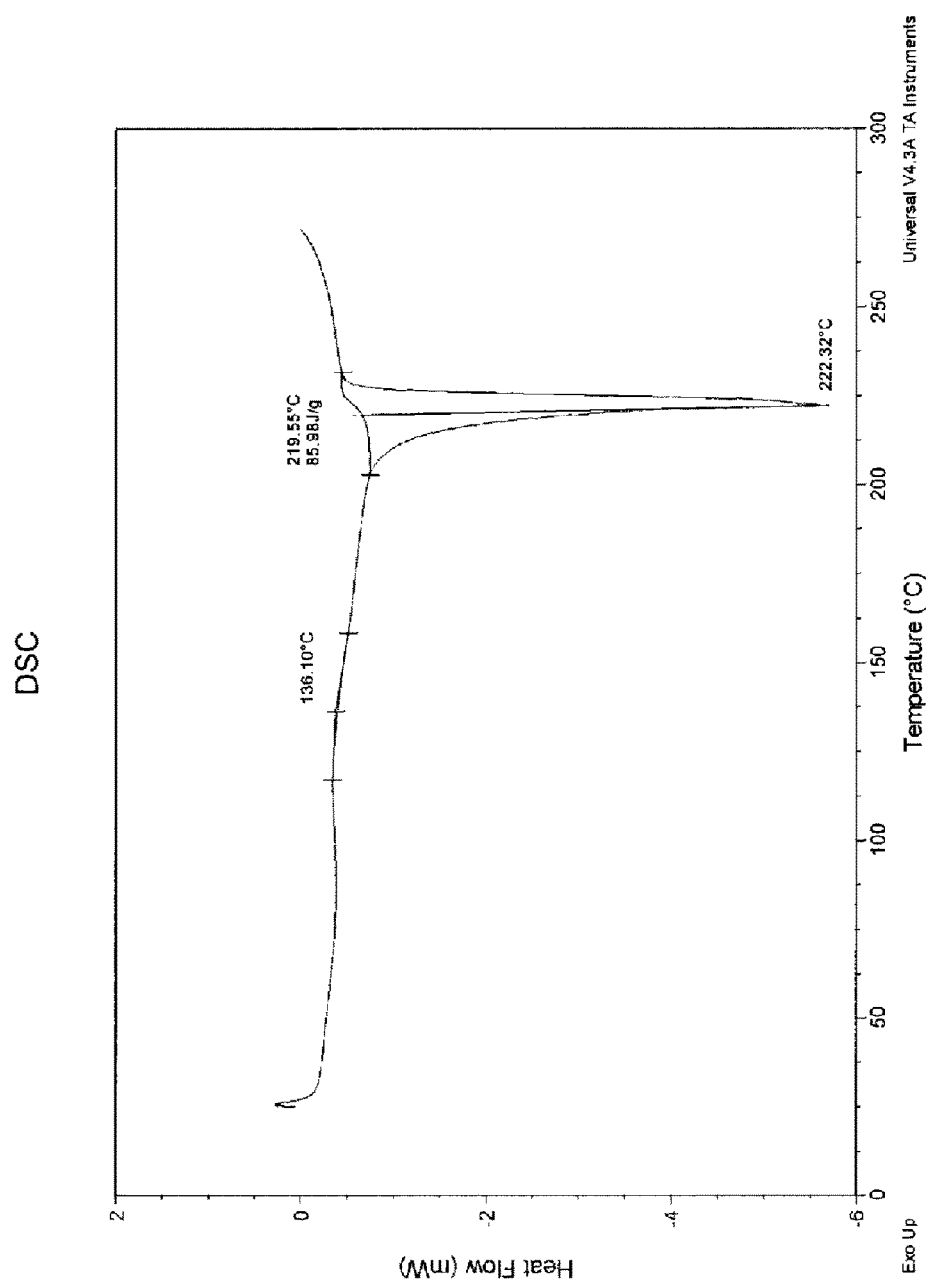
FIG. 34 shows a characteristic DSC scan of Form B Isopropyl Alcohol.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol which is characterized by a DSC scan substantially the same as FIG. 34 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form A with IPA;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and IPA; and (c) recrystallizing the solid to prepare Form B Isopropyl Alcohol.

In certain embodiments, the solution in Step (b) is created by heating the mixture of Step (a) to reflux.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile is provided. Form B Acetonitrile can be distinguished by the XRPD diffraction in FIG. 5 and/or peak assignments of the XRPD diffraction of FIG. 5 in Table 5.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by at least one specific XRPD diffraction peak at about (2θdegrees±0.2) 25.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine Form B Acetonitrile, characterized by at least one specific XRPD diffraction peak at about (2θdegrees±0.2) 25.661 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by XRPD diffraction peaks at about (2θdegrees±0.2) 10.0, 13.5, 16.9, 24.9 and 25.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by XRPD diffraction peaks at about (2θdegrees±0.2) 9.98, 13.46, 16.921, 24.899 and 25.661 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by XRPD diffraction peaks at about (2θdegrees±0.2) 10.0, 13.5, 16.9, 21.7, 24.9 and 25.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by XRPD diffraction peaks at about (2θdegrees±0.2) 9.98, 13.46, 16.921, 21.741, 24.899 and 25.661 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by XRPD diffraction peaks at about (2θdegrees±0.2) 8.5, 10.0, 13.5, 16.9, 18.1, 19.8, 21.2, 21.7, 23.3, 24.9 and 25.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile, characterized by XRPD diffraction peaks at about (2θdegrees±0.2) 8.46, 9.98, 13.46, 16.921, 18.12, 19.842, 21.239, 21.741, 23.319, 24.899 and 25.661 is provided.

Figure 5:
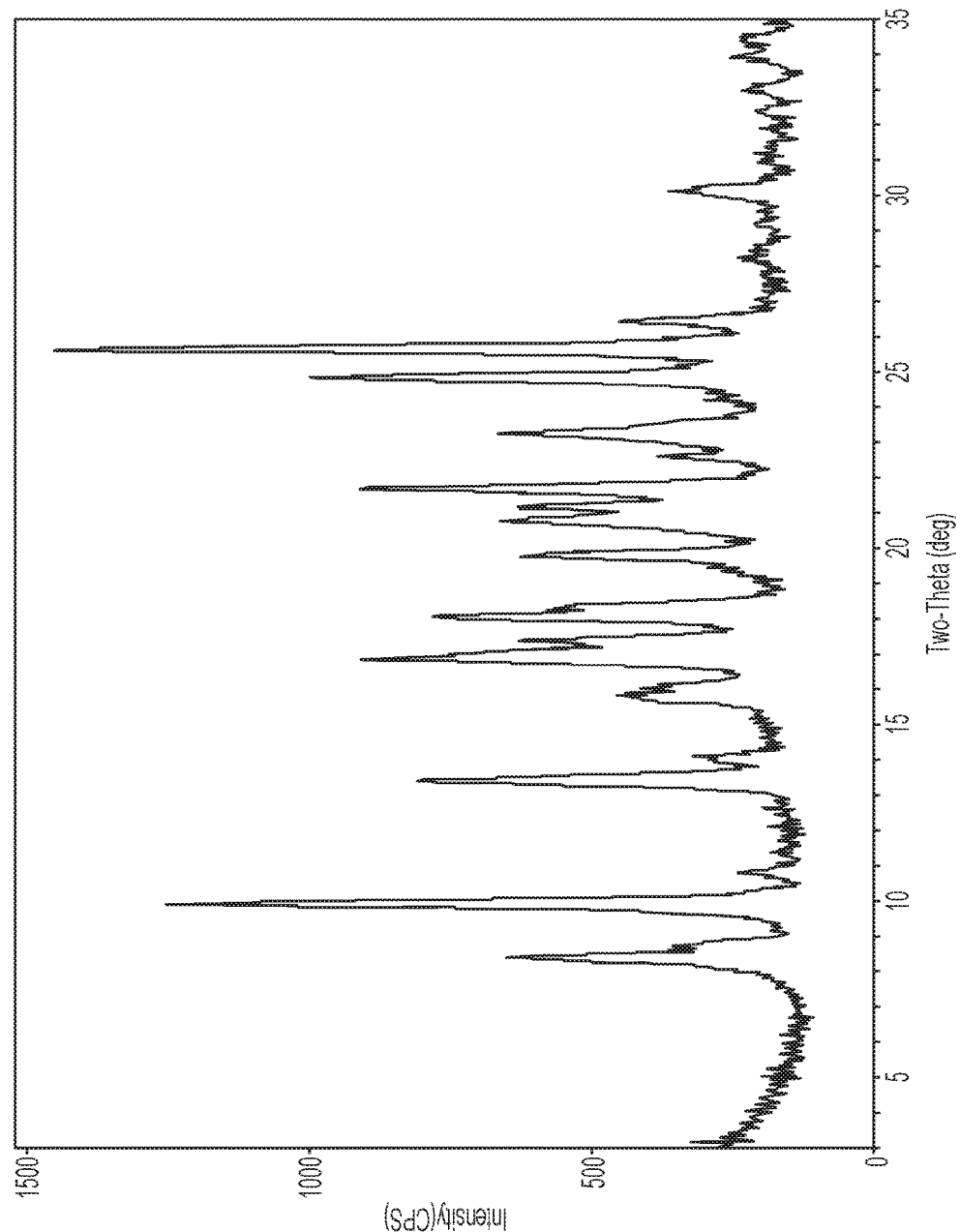
FIG. 5 shows a characteristic XRPD scan of Form B Acetonitrile.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile which has an XRPD diffraction pattern substantially the same as FIG. 5 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile which is characterized by XRPD diffraction peaks (2θdegrees±0.2) substantially the same as Table 5 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile which is characterized by an endotherm at about 224.2° C. is provided.

Figure 35:
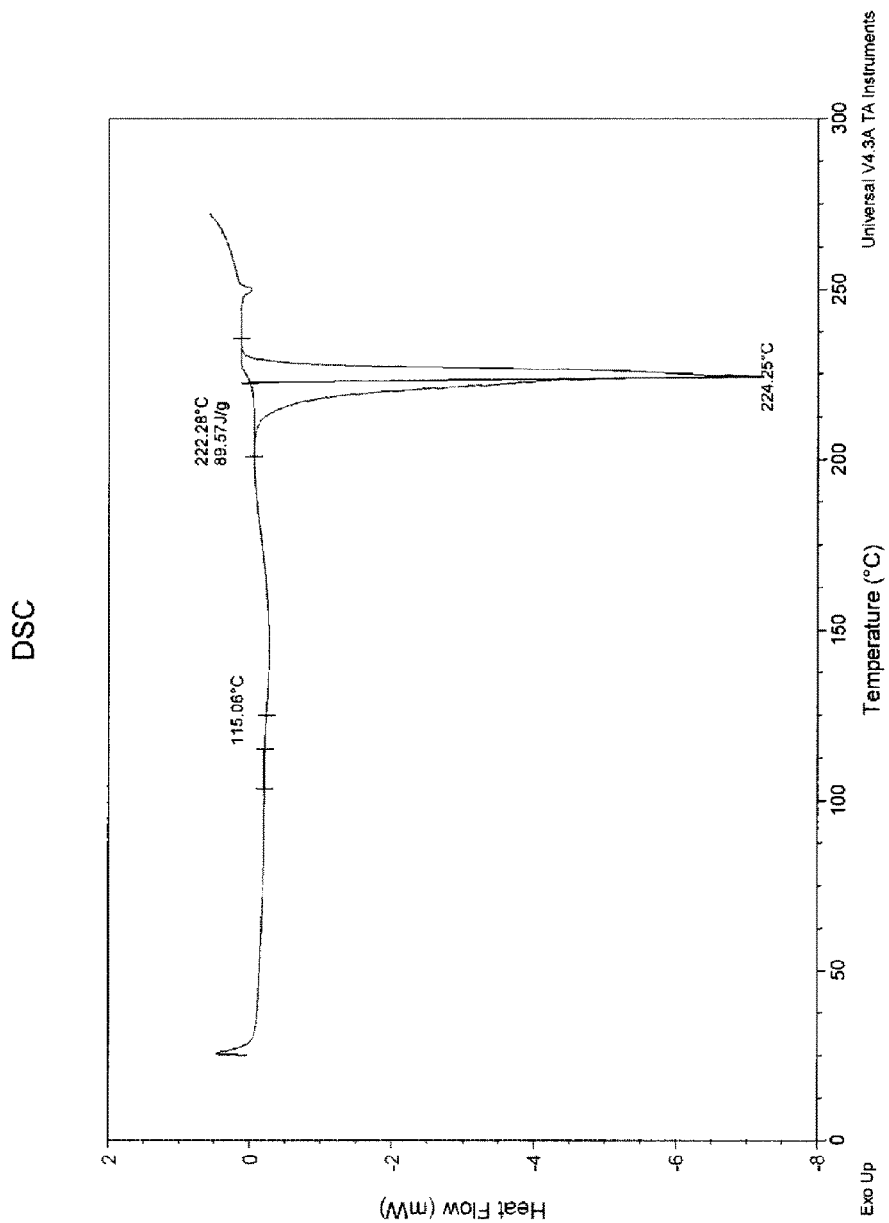
FIG. 35 shows a characteristic DSC scan of Form B Acetonitrile.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile which is characterized by a DSC scan substantially the same as FIG. 35 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetonitrile comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and ACN; and (b) recrystallizing the solid to prepare Form B Acetonitrile.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

In certain embodiments, a crystalline polymorph N4-(4-([1,2,4]triazolo[1,5-a]pyridin-7-yloxy)-3-methylphenyl)-

N6-(4,4-dimethyl-4,5-dihydrooxazol-2-yl)quinazoline-4,6-diamine Form B Acetone is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone is provided. Form B Acetone can be distinguished by the XRPD diffraction in FIG. 6 and/or peak assignments of the XRPD diffraction of FIG. 6 in Table 6.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone, characterized by at least one specific XRPD diffraction peak at about (2θdegrees±0.2) 9.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone, characterized by at least one specific XRPD diffraction peak at about (2θdegrees±0.2) 9.936 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone, characterized by XRPD diffraction peaks at about (2θdegrees±0.2) 9.9, 17.0, 18.0, 24.7 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone, characterized by XRPD diffraction peaks at about (2θdegrees±0.2) 9.936, 17.02, 17.98, 24.679 and 25.52 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone, characterized by XRPD diffraction peaks at about (2θdegrees±0.2) 8.4, 9.9, 13.0, 17.0, 18.0, 19.8, 23.5, 24.7 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone, characterized by XRPD diffraction peaks at about (2θdegrees±0.2) 8.378, 9.936, 13.041, 17.02, 17.98, 19.758, 23.498, 24.679 and 25.52 is provided.

Figure 6:
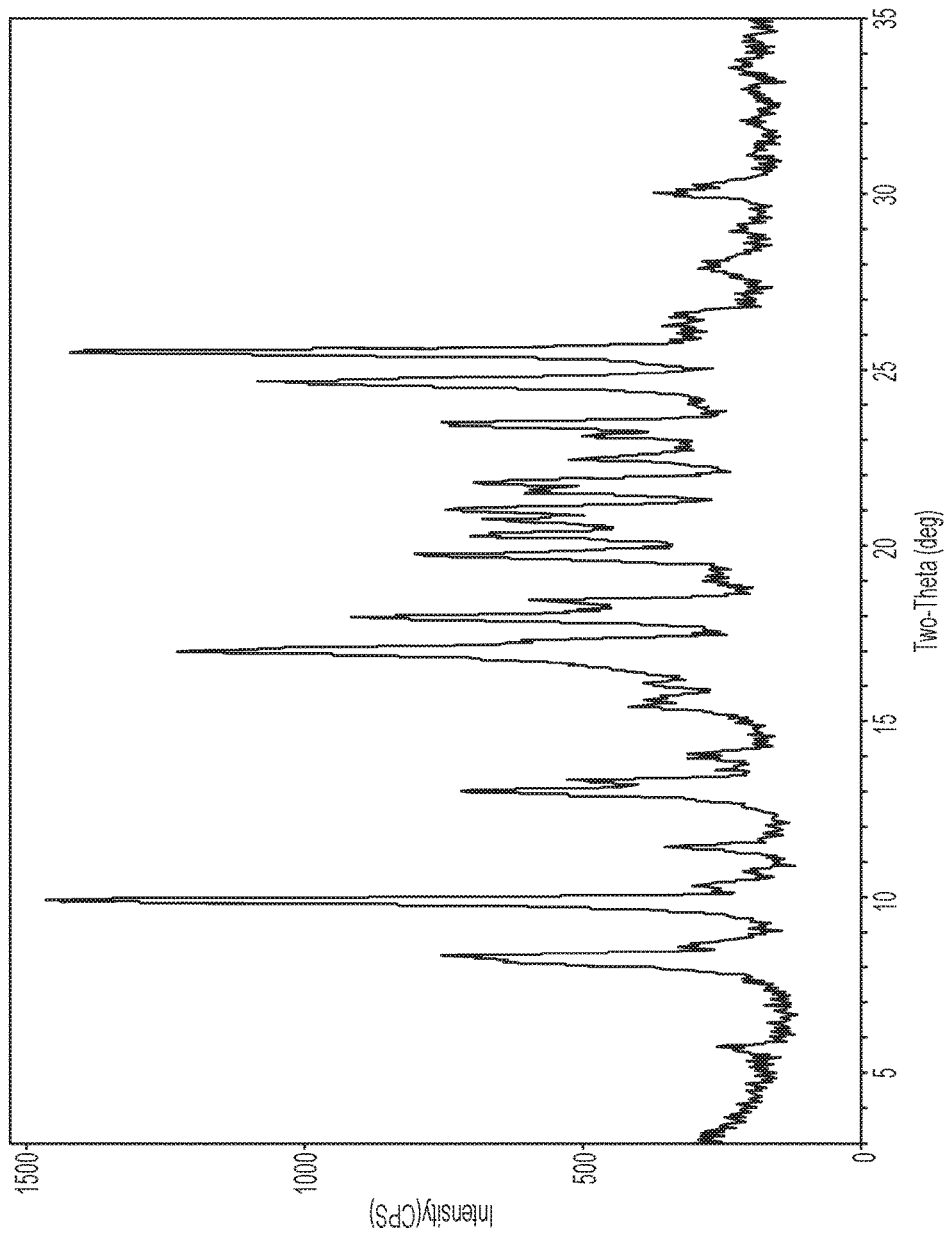
FIG. 6 shows a characteristic XRPD scan of Form B Acetone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone which has an XRPD diffraction pattern substantially the same as FIG. 6 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone which is characterized by XRPD diffraction peaks (2θdegrees±0.2) substantially the same as Table 6 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone which is characterized by an endotherm at about 114.5° C. and 224.1° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone which is characterized by an endotherm at about 224.1° C. is provided.

Figure 36:
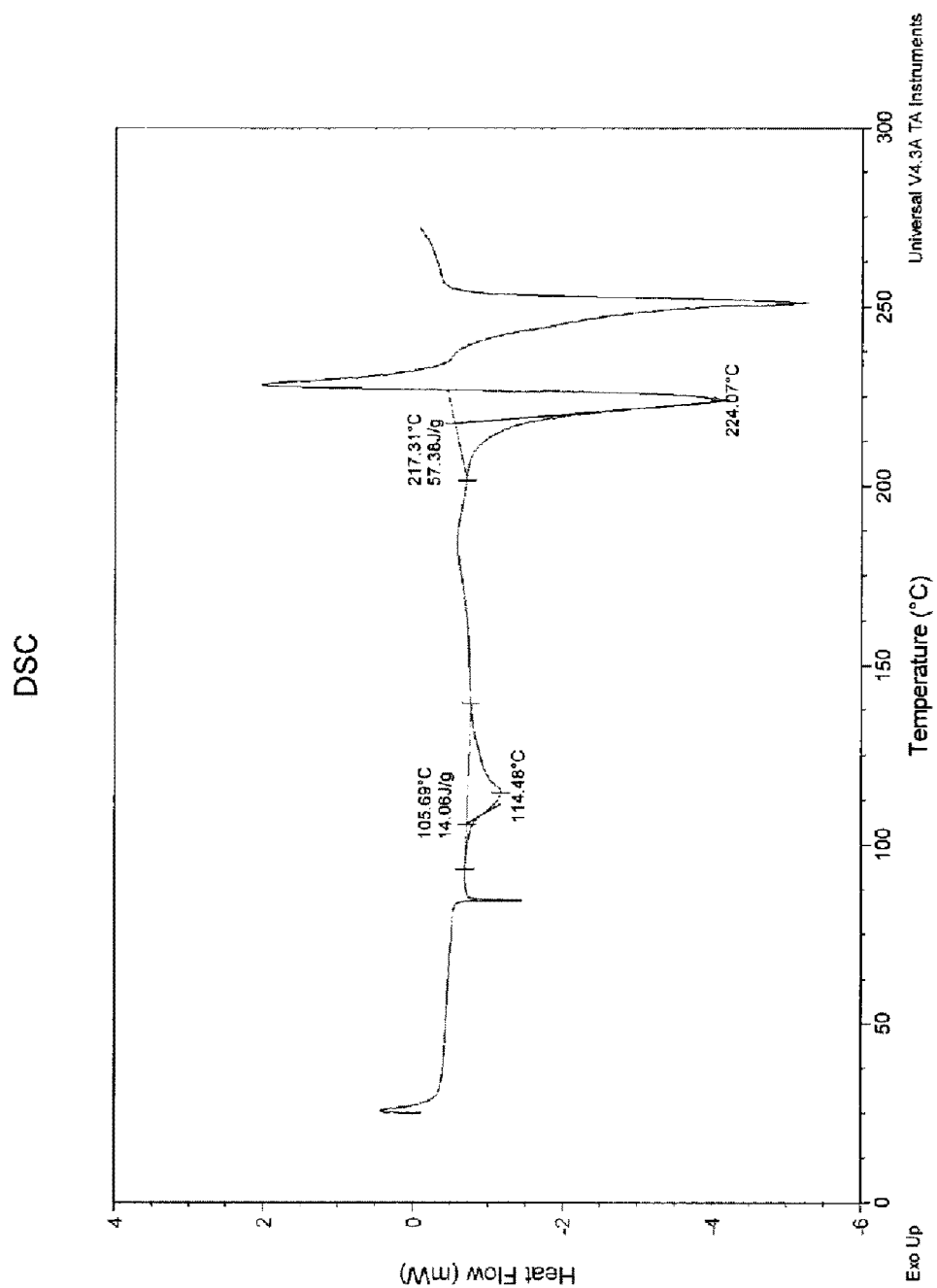
FIG. 36 shows a characteristic DSC scan of Form B Acetone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone which is characterized by a DSC scan substantially the same as FIG. 36 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Acetone comprising:

(a) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and acetone;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and acetone; and (c) recrystallizing the solid to prepare Form B Acetone.

In certain embodiments, the solution in Step (b) is created by heating the mixture of Step (a) to reflux.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane is provided. Form B Dichloromethane can be distinguished by the XRPD diffraction in FIG. 7 and/or peak assignments of the XRPD diffraction of FIG. 7 in Table 7.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by at least one specific XRPD diffraction peak at about (2θdegrees±0.2) 16.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by at least one specific XRPD diffraction peak at about (2θdegrees±0.2) 16.918 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by XRPD diffraction peaks at about (2θdegrees±0.2) 10.0, 13.4, 16.9, 20.7 and 25.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by XRPD diffraction peaks at about (2θdegrees±0.2) 9.977, 13.381, 16.918, 20.738 and 25.641 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by XRPD diffraction peaks at about (2θdegrees±0.2) 8.4, 10.0, 13.4, 16.9, 18.0, 20.7, 24.8 and 25.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by XRPD diffraction peaks at about (2θdegrees±0.2) 8.439, 9.977, 13.381, 16.918, 18.041, 20.738, 24.779 and 25.641 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6- diamine Form B Dichloromethane, characterized by XRPD diffraction peaks at about (2θdegrees±0.2) 8.4, 10.0, 13.4, 16.9, 17.4, 18.0, 18.3, 19.9, 20.7, 21.2, 21.8, 23.5, 24.8 and 25.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane, characterized by XRPD diffraction peaks at about (2θdegrees±0.2) 8.439, 9.977, 13.381, 16.918, 17.438, 18.041, 18.34, 19.899, 20.738, 21.161, 21.802, 23.46, 24.779 and 25.641 is provided.

Figure 7:
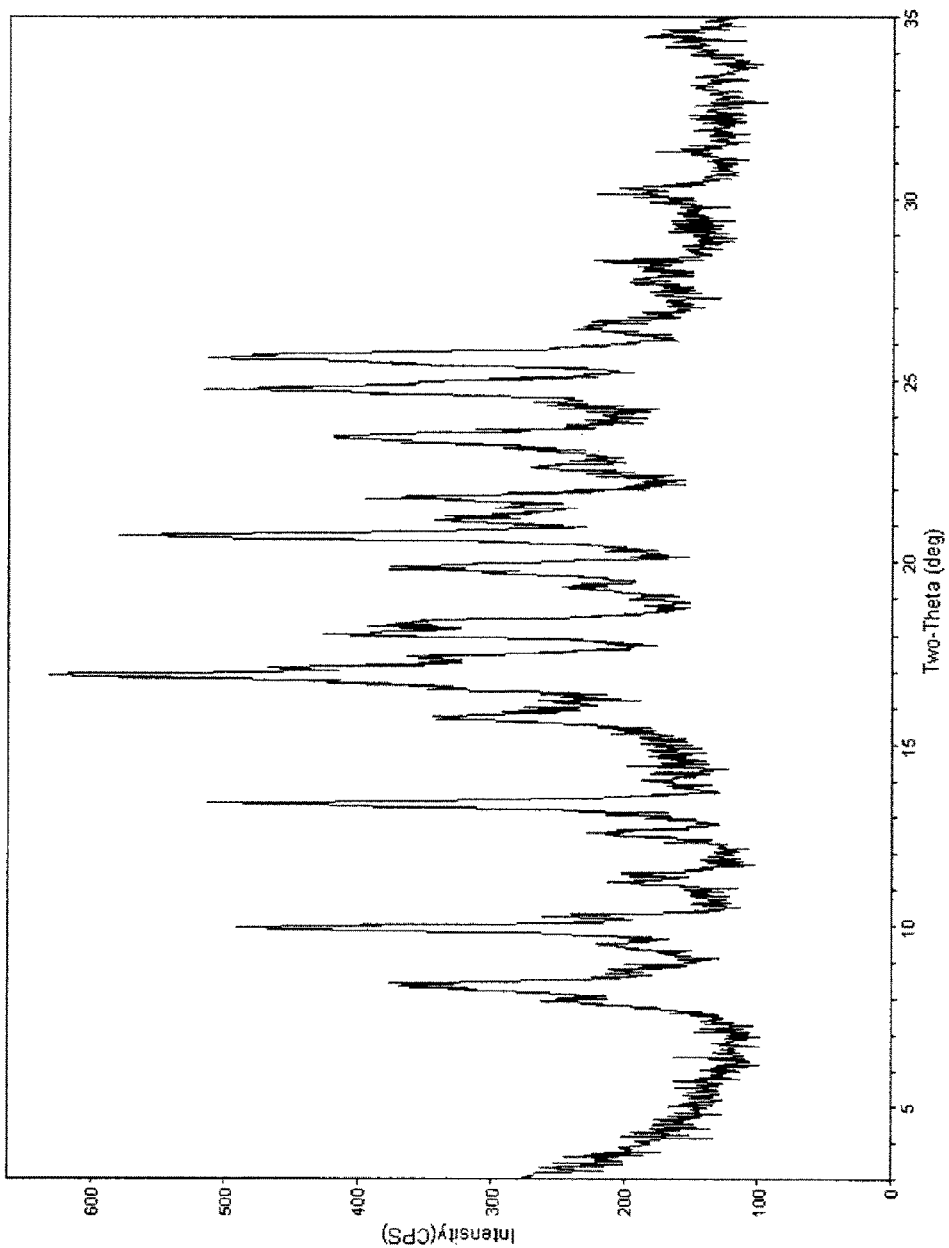
FIG. 7 shows a characteristic XRPD scan of Form B Dichloromethane.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane which has an XRPD diffraction pattern substantially the same as FIG. 7 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane which is characterized by XRPD diffraction peaks (2θdegrees±0.2) substantially the same as Table 7 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane which is characterized by an endotherm at about 129.1° C. and 220.7° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane which is characterized by an endotherm at about 220.7° C. is provided.

Figure 37:
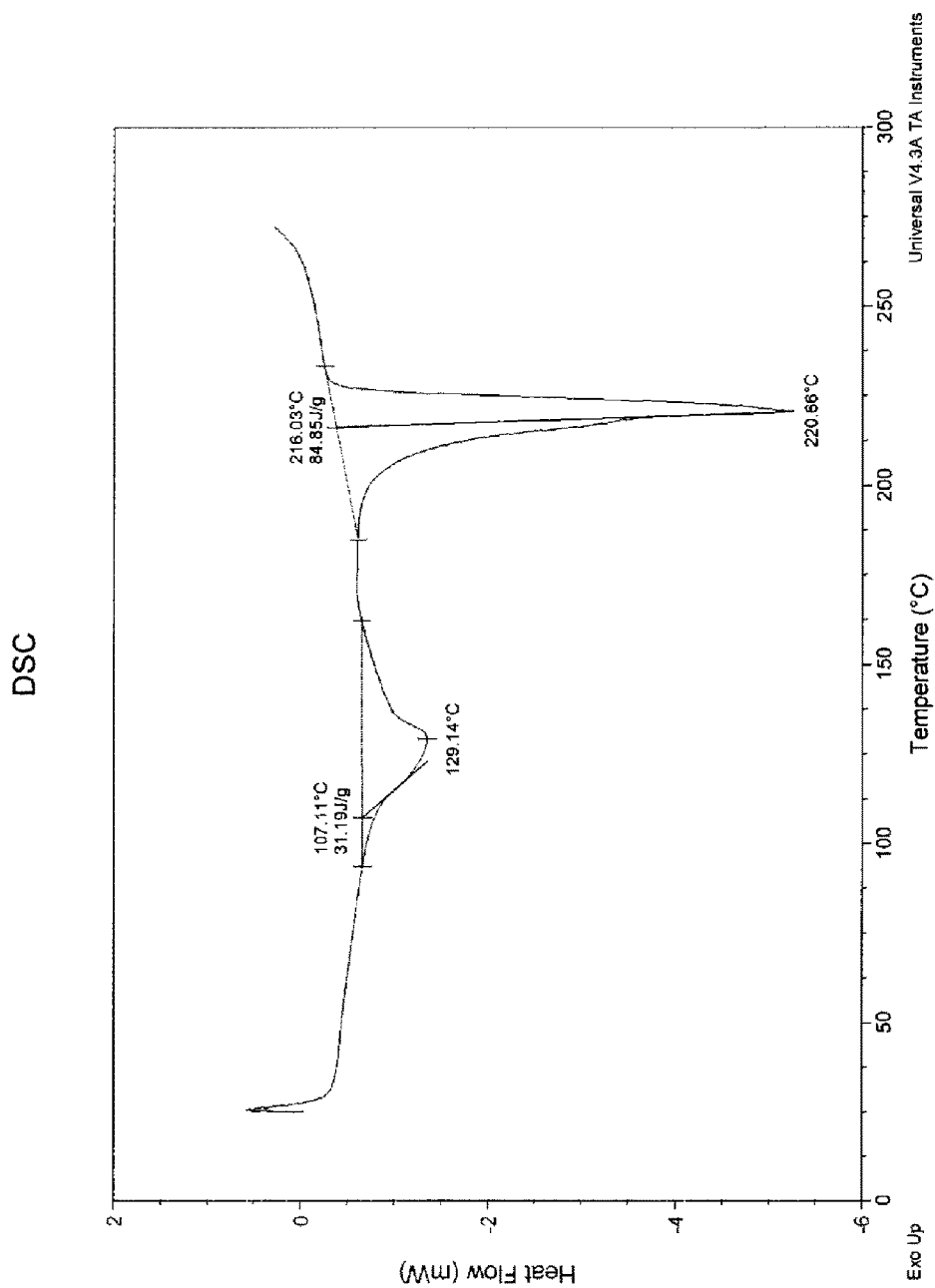
FIG. 37 shows a characteristic DSC scan of Form B Dichloromethane.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane which is characterized by a DSC scan substantially the same as FIG. 37 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Dichloromethane comprising:

(a) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and DCM;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and DCM; and (c) recrystallizing the solid to prepare Form B Dichloromethane.

In certain embodiments, the solution in Step (b) is created by heating the mixture of Step (a) to reflux.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran is provided. Form B Tetrahydrofuran can be distinguished by the XRPD diffraction in FIG. 8 and/or peak assignments of the XRPD diffraction of FIG. 8 in Table 8.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by at least one specific XRPD diffraction peak at about (2θdegrees±0.2) 25.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by at least one specific XRPD diffraction peak at about (2θdegrees±0.2) 25.44 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by XRPD diffraction peaks at about (2θdegrees±0.2) 9.8, 16.7, 17.9, 24.7 and 25.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by XRPD diffraction peaks at about (2θdegrees±0.2) 9.819, 16.7, 17.92, 24.66 and 25.44 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by XRPD diffraction peaks at about (2θdegrees±0.2) 9.8, 13.4, 16.7, 17.9, 21.4, 24.7 and 25.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by XRPD diffraction peaks at about (2θdegrees±0.2) 9.819, 13.38, 16.7, 17.92, 21.4, 24.66 and 25.44 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran, characterized by XRPD diffraction peaks at about (2θdegrees±0.2) 9.8, 13.4, 16.7, 17.9, 21.4, 22.9, 24.7 and 25.4 is provided. In a further embodiment, a crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B Tetrahydrofuran, characterized by XRPD diffraction peaks at about (2θdegrees±0.2) 9.819, 13.38, 16.7, 17.92, 21.4, 22.92, 24.66 and 25.44 is provided.

Figure 8:
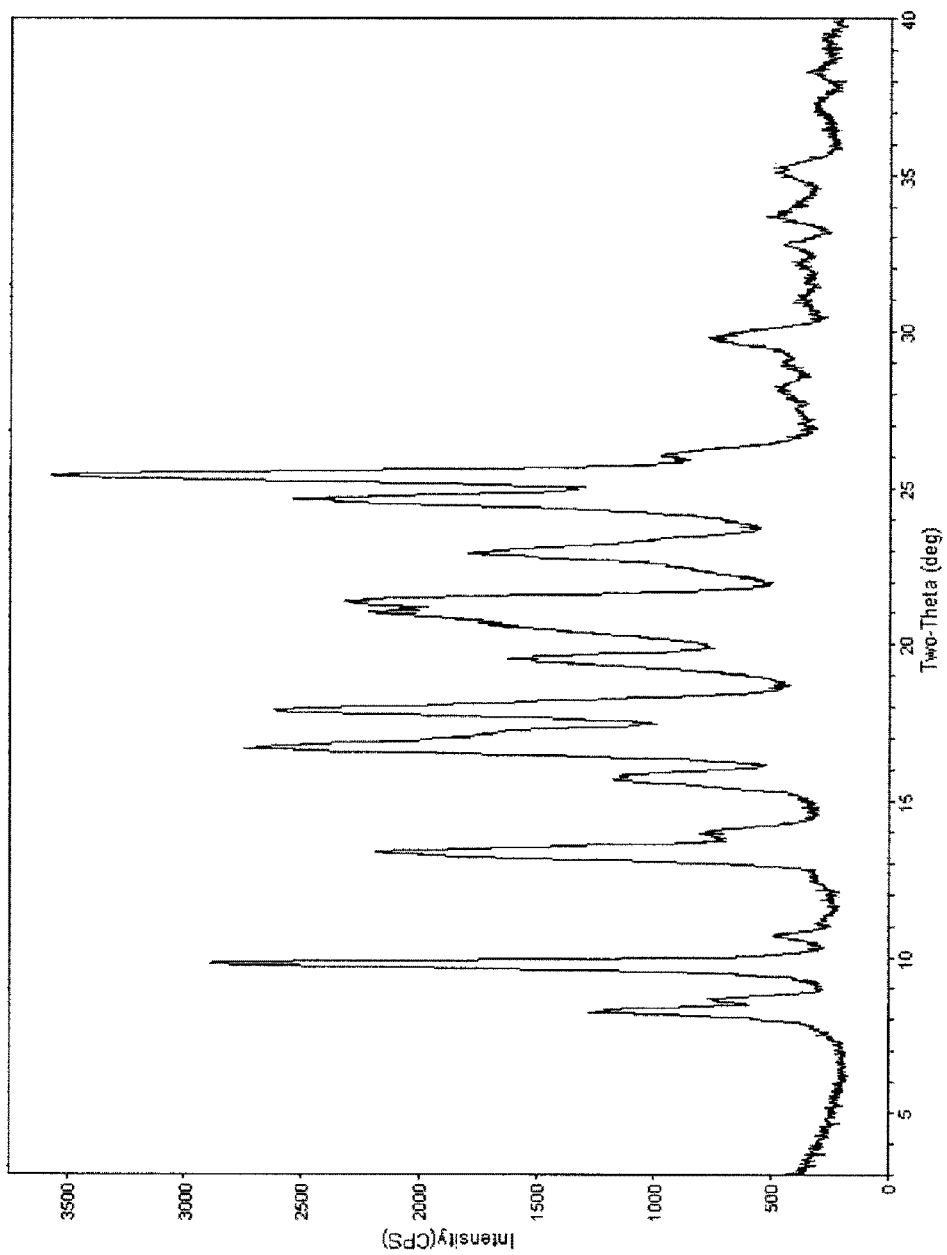
FIG. 8 shows a characteristic XRPD scan of Form B Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran which has an XRPD diffraction pattern substantially the same as FIG. 8 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran which is characterized by XRPD diffraction peaks (2θdegrees±0.2) substantially the same as Table 8 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran which is characterized by an endotherm at about 228.5° C. is provided.

Figure 38:
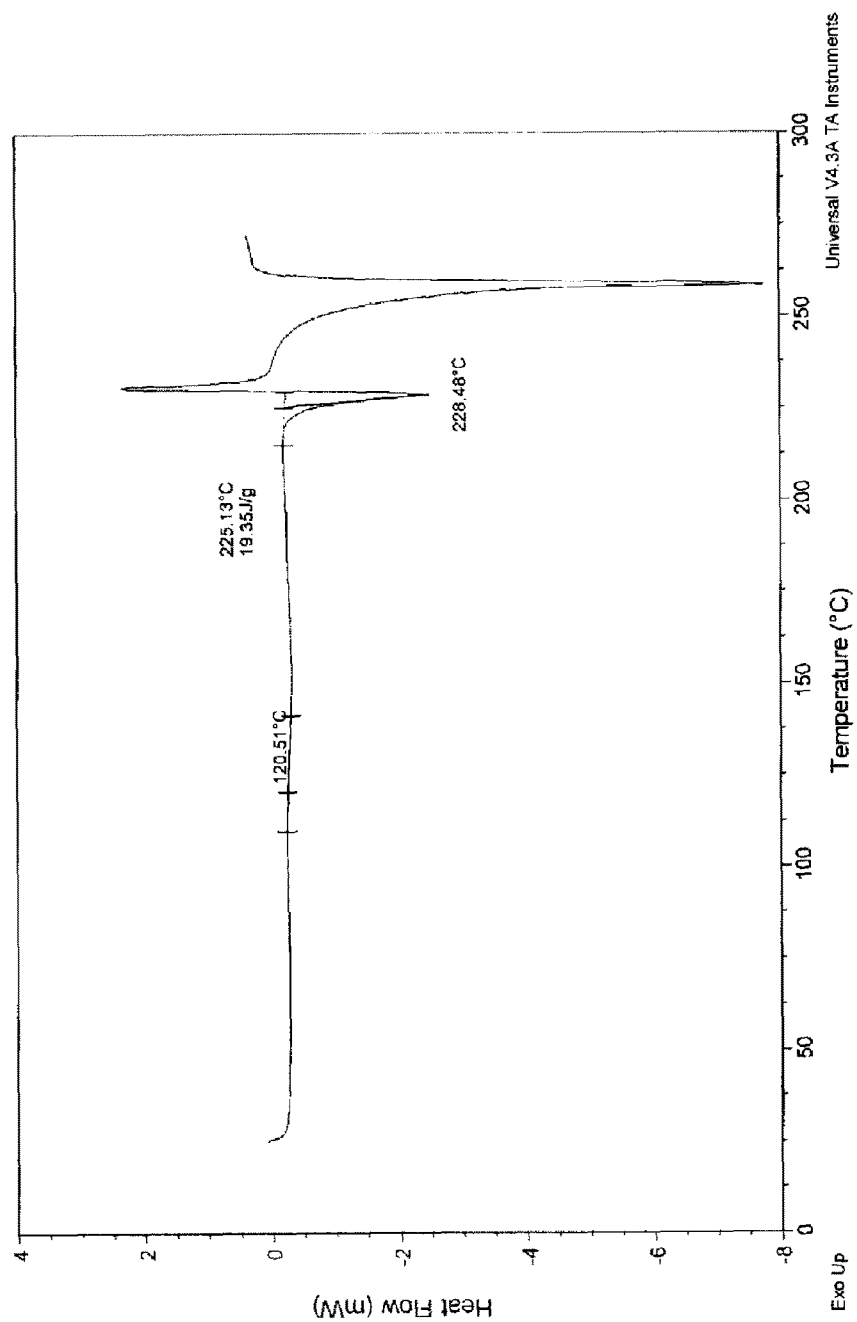
FIG. 38 shows a characteristic DSC scan of Form B Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran which is characterized by a DSC scan substantially the same as FIG. 38 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran comprising:

(a) mixing N4-(4-([1,2,4]triazolo[1,5-c]pyridin-7-yloxy)-3-methylphenyl)-N6-(4,4-dimethyl-4,5-dihydrooxazol-2-yl) quinazoline-4,6-diamine Form G mono-Tetrahydrofuran and THF; and (b) recrystallizing the solid to prepare Form B Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous is provided. Form B Anhydrous can be distinguished by the XRPD diffraction in FIG. 9 and/or peak assignments of the XRPD diffraction of FIG. 9 in Table 9.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous, characterized by at least one specific XRPD diffraction peak at about (2θdegrees±0.2) 9.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine Form B Anhydrous, characterized by at least one specific XRPD diffraction peak at about (2θdegrees±0.2) 9.938 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous, characterized by XRPD diffraction peaks at about (2θdegrees±0.2) 9.9, 13.6, 18.1, 21.5 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous, characterized by XRPD diffraction peaks at about (2θdegrees±0.2) 9.938, 13.641, 18.1, 21.498 and 25.541 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous, characterized by XRPD diffraction peaks at about (2θdegrees±0.2) 8.4, 9.9, 13.6, 16.8, 17.1, 18.1, 21.2, 21.5, 24.9 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous, characterized by XRPD diffraction peaks at about (2θdegrees±0.2) 8.44, 9.938, 13.641, 16.841, 17.099, 18.1, 21.22, 21.498, 24.901 and 25.541 is provided.

Figure 9:
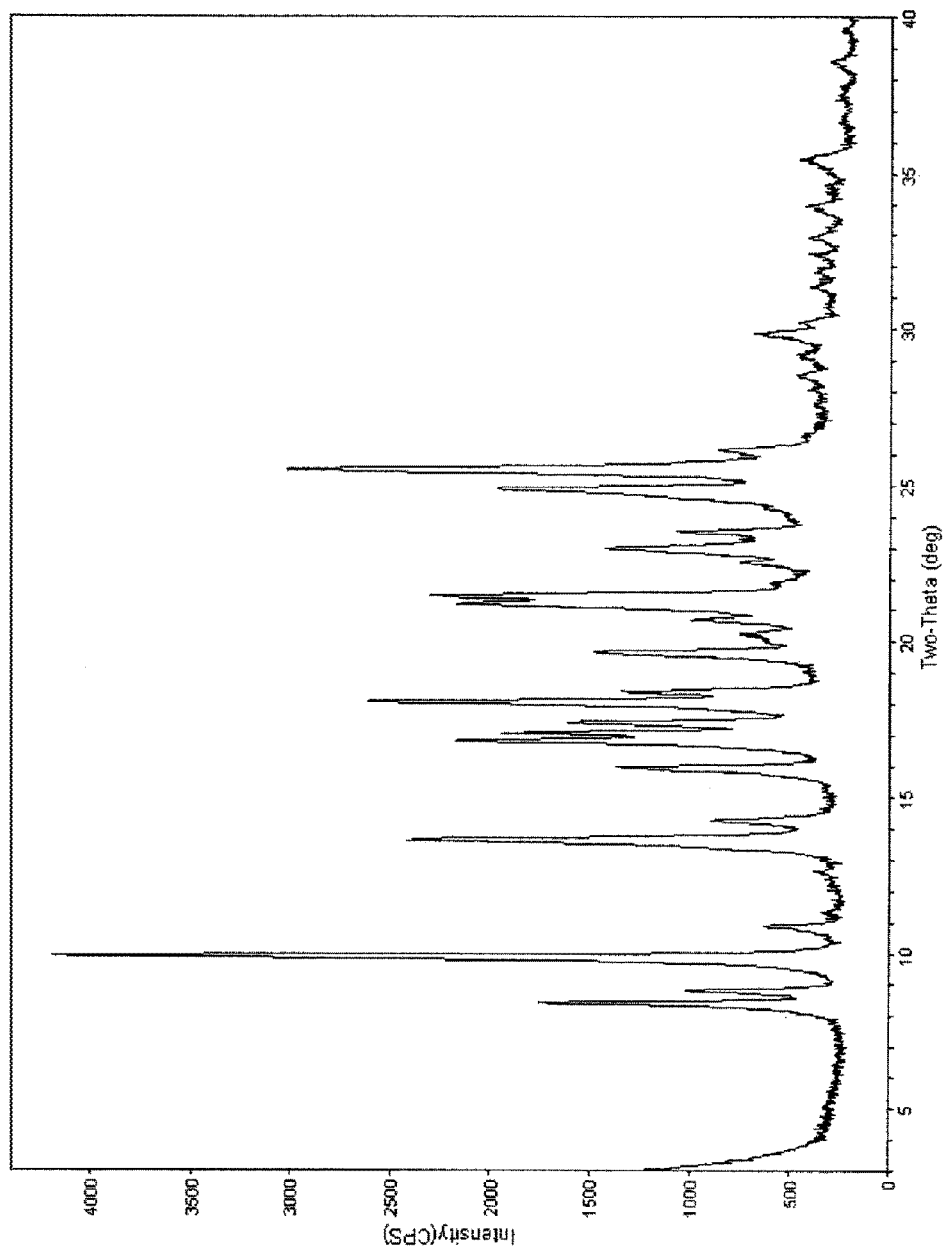
FIG. 9 shows a characteristic XRPD scan of Form B Anhydrous.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous which has an XRPD diffraction pattern substantially the same as FIG. 9 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous which is characterized by XRPD diffraction peaks (2θdegrees±0.2) substantially the same as Table 9 is provided.

Certain embodiments provide a process for preparing N4-(4-[1,2,4]triazolo[1,5-a]pyridin-7-yloxy)-3-methylphenyl)-N6-(4,4-dimethyl-4,5-dihydrooxazol-2-yl)quinazoline-4,6-diamine Form B Anhydrous comprising:

(a) heating N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine Form B; and (b) recovering the solid to prepare Form B Anhydrous.

The Form B in Step (a) may be Form B Methanol, Ethanol, Isopropyl Alcohol, Acetonitrile, Acetone, Dichloromethane or Tetrahydrofuran. In certain embodiments, the Form B in Step (a) is Form B Ethanol. In certain embodiments, the heating in Step (a) is done at about 100 to about 200° C.

Form C

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C is provided. Form C can be distinguished by the XRPD diffraction in FIG. 10 and/or peak assignments of the XRPD diffraction of FIG. 10 in Table 10.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by at least one specific XRPD diffraction peak at about (2θdegrees±0.2) 5.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by at least one specific XRPD diffraction peak at about (2θdegrees±0.2) 5.04 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by XRPD diffraction peaks at about (2θdegrees±0.2) 5.0, 14.4, 15.3, 18.4 and 18.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by XRPD diffraction peaks at about (2θdegrees±0.2) 5.04, 14.435, 15.301, 18.437 and 18.902 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by XRPD diffraction peaks at about (2θdegrees±0.2) 5.0, 7.2, 10.2, 14.4, 15.3, 15.7, 17.5, 18.4, 18.9, 19.6, 22.3 and 24.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by XRPD diffraction peaks at about (2θdegrees±0.2) 5.04, 7.159, 10.159, 14.435, 15.301, 15.717, 17.501, 18.437, 18.902, 19.638, 22.34 and 24.181 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by XRPD diffraction peaks at about (2θdegrees±0.2) 5.0, 7.2, 10.2, 14.4, 15.3, 15.7, 16.7, 17.5, 18.1, 18.4, 18.9, 19.6, 21.1, 21.4, 22.3 and 24.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C, characterized by XRPD diffraction peaks at about (2θdegrees±0.2) 5.04, 7.159, 10.159, 14.435, 15.301, 15.717, 16.719, 17.501, 18.059, 18.437, 18.902, 19.638, 21.08, 21.437, 22.34 and 24.181 is provided.

Figure 10:
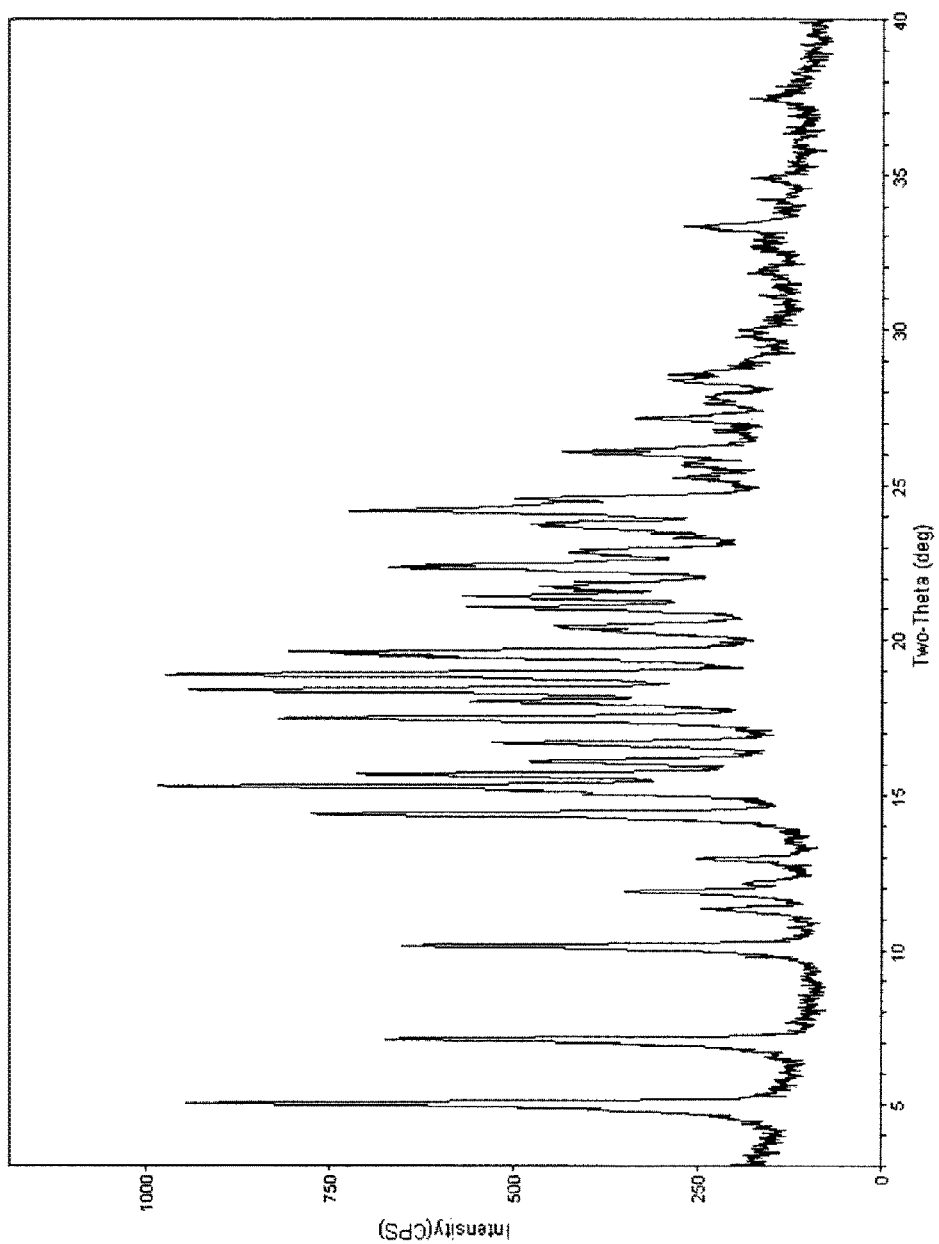
FIG. 10 shows a characteristic XRPD scan of Form C.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C which has an XRPD diffraction pattern substantially the same as FIG. 10 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C which is characterized by XRPD diffraction peaks (2θdegrees±0.2) substantially the same as Table 10 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C which is characterized by an endotherm at about 253.6° C. is provided.

Figure 39:
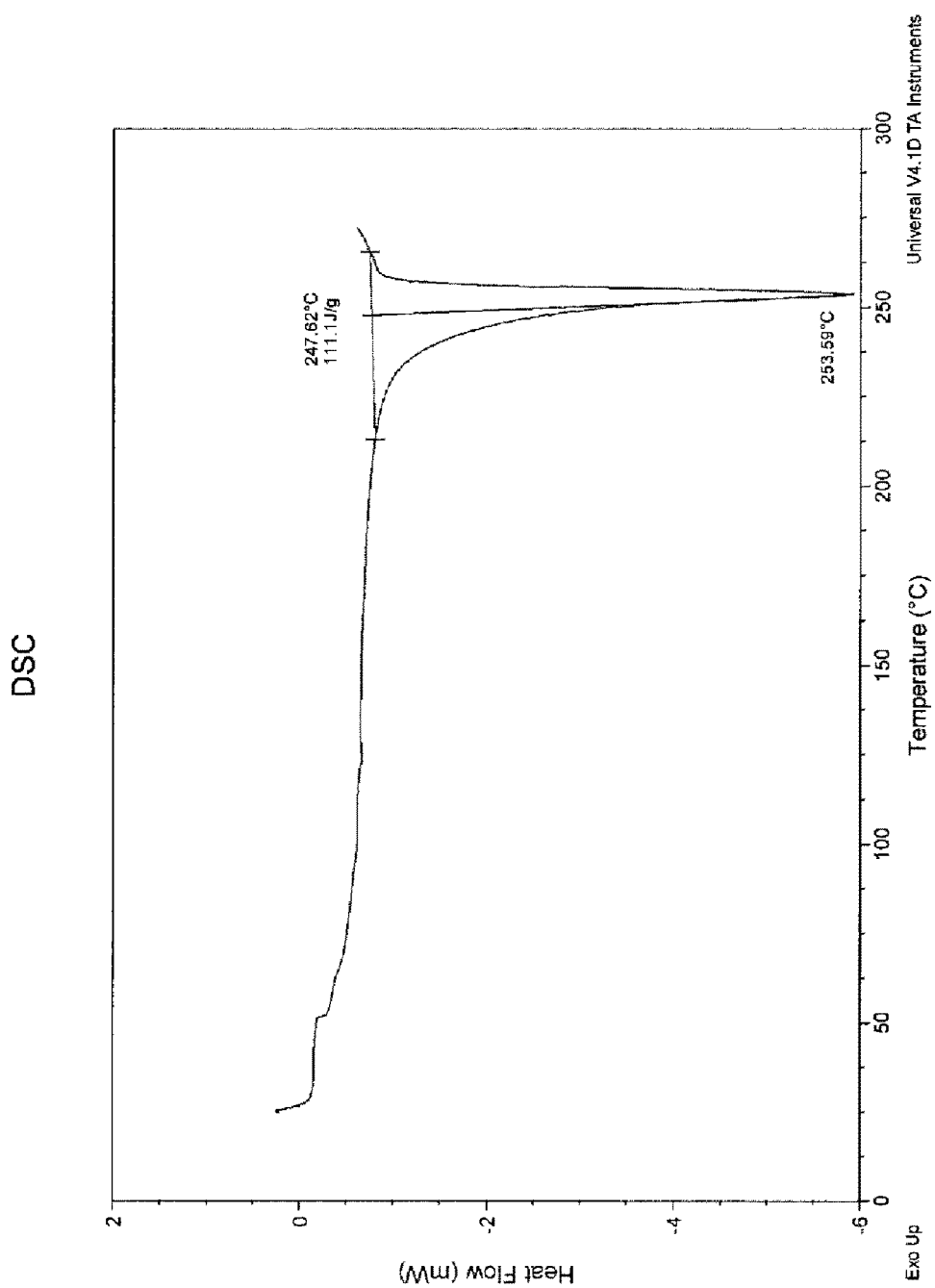
FIG. 39 shows a characteristic DSC scan of Form C.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C which is characterized by a DSC scan substantially the same as FIG. 39 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form C comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form A and 2-methoxyethanol;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and 2-methoxyethanol; and (c) recrystallizing the solid to prepare Form C.

In certain embodiments, the solution in Step (b) is created by heating the mixture of Step (a) to about 50° C.

Form D

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D is provided. Form D forms isomorphic solvates. Form D can be distinguished by the representative XRPD diffraction in FIGS. 11 to 14 and/or representative peak assignments of the XRPD diffraction of FIGS. 11 to 14 in Tables 11 to 14.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.3) 8.0 and 12.7 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.2) 8.0 and 12.7 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.3) 8.0 and 12.6 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.2) 8.0 and 12.6 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.4) 8.0, 9.8, 11.3, 12.7, 13.9, 16.1, 17.1 and 19.8 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.2) 8.0, 9.8, 11.3, 12.7, 13.9 and 17.1 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.3) 8.0, 9.8, 11.3, 12.6, 13.9, 16.2, 17.2 and 19.7 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.2) 8.0, 9.8, 11.3, 12.6, 13.9, 17.2 and 19.7 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.5) 8.0, 9.8, 11.3, 12.7, 13.9, 16.1, 17.1, 19.8, 21.4, 22.1, 23.6, 25.3 and 27.5 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.2) 8.0, 9.8, 11.3, 12.7, 13.9, 17.2, 22.1 and 25.3 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.3) 8.0, 9.8, 11.3, 12.6, 13.9, 16.2, 17.2, 19.7, 21.3, 22.1, 23.4, 25.3 and 27.4 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D, characterized by XRPD diffraction peaks at about (2θdegrees±0.2) 8.0, 9.8, 11.3, 12.6, 13.9, 17.2, 19.7, 22.1 and 25.3 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D comprising:

(a1) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and a solvent selected from EtOAc, dioxane and propyl acetate, or (a2) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E and a solvent selected from acetone and propyl acetate, and (b) recrystallizing the solid to prepare Form D.

In certain embodiments, the solvent in Step (a1) is selected from EtOAc and dioxane.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate is provided. Form D Ethyl Acetate can be distinguished by the XRPD diffraction in FIG. 11 and/or peak assignments of the XRPD diffraction of FIG. 11 in Table 11.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate, characterized by at least one specific XRPD diffraction peak at about (2θdegrees±0.2) 8.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate, characterized by at least one specific XRPD diffraction peak at about (2θdegrees±0.2) 7.959 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate, characterized by XRPD diffraction peaks at about (2θdegrees±0.2) 8.0, 12.7, 16.1, 17.1 and 19.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate, characterized by XRPD diffraction peaks at about (2θdegrees±0.2) 7.959, 12.66, 16.099, 17.118 and 19.761 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate, characterized by XRPD diffraction peaks at about (2θdegrees±0.2) 8.0, 9.8, 11.3, 12.7, 16.1, 17.1, 19.8 and 23.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate, characterized by XRPD diffraction peaks at about (2θdegrees±0.2) 7.959, 9.798, 11.321, 12.66, 16.099, 17.118, 19.761 and 23.599 is provided.

Figure 11:
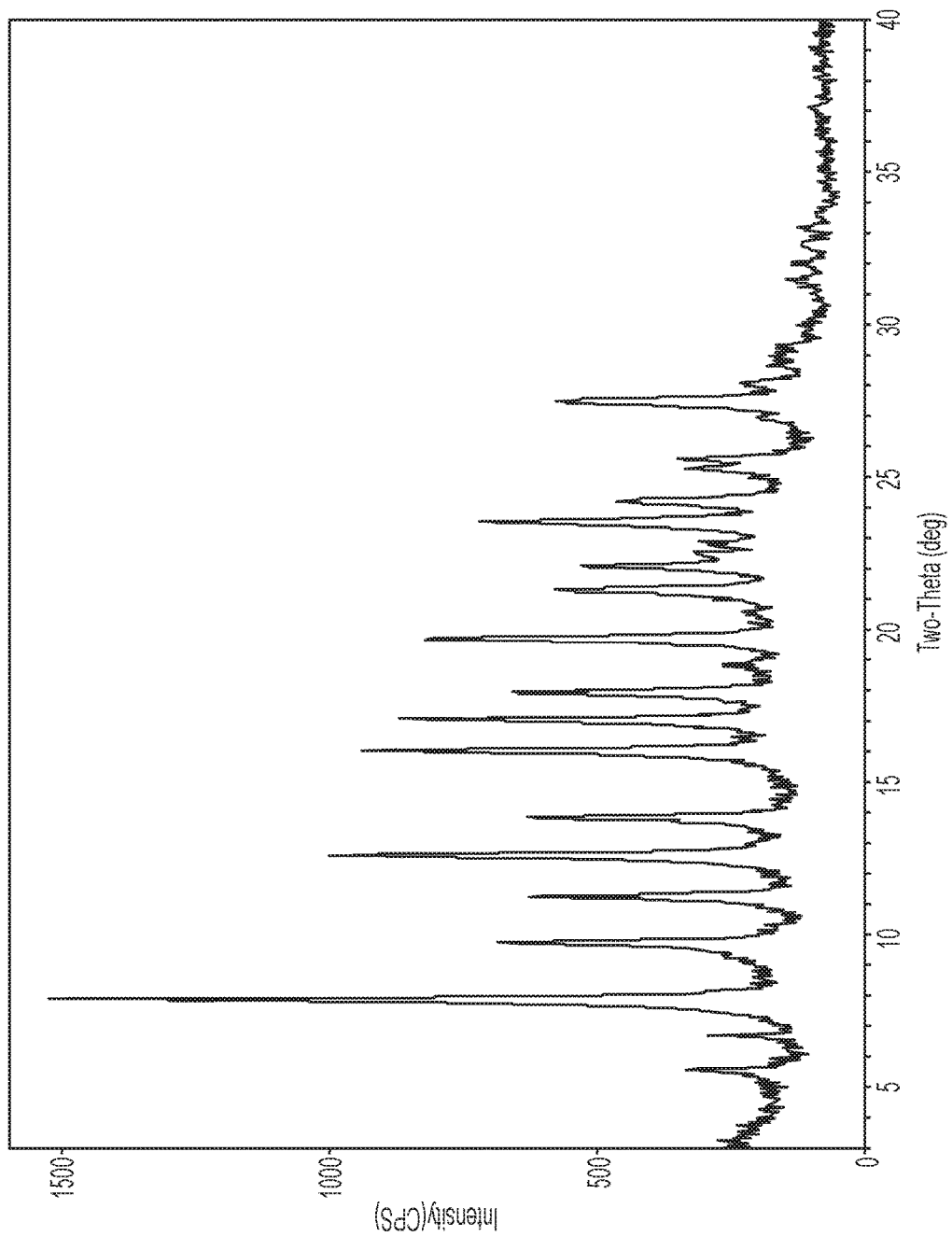
FIG. 11 shows a characteristic XRPD scan of Form D Ethyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate which has an XRPD diffraction pattern substantially the same as FIG. 11 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate which is characterized by XRPD diffraction peaks (2θdegrees±0.2) substantially the same as Table 11 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate which is characterized by endotherms at about 113.0° C. and 240.3° C. is provided.

Figure 40:
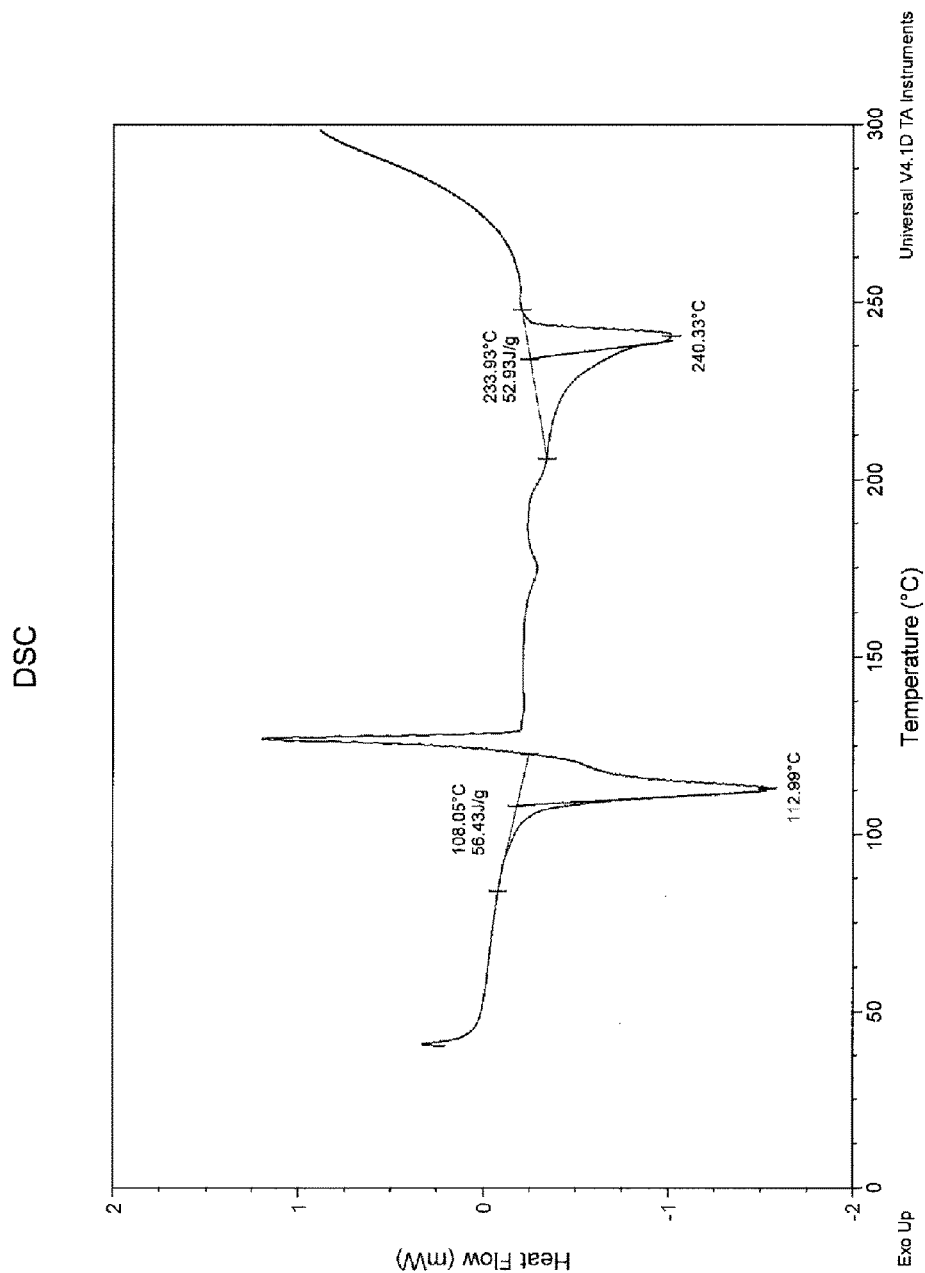
FIG. 40 shows a characteristic DSC scan of Form D Ethyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate which is characterized by a DSC scan substantially the same as FIG. 40 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate comprising:

(a) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and EtOAc; and (b) recrystallizing the solid to prepare Form D Ethyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane is provided. Form D Dioxane can be distinguished by the XRPD diffraction in FIG. 12 and/or peak assignments of the XRPD diffraction of FIG. 12 in Table 12.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by at least one specific XRPD diffraction peak at about (2θdegrees±0.2) 19.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by at least one specific XRPD diffraction peak at about (2θdegrees±0.2) 19.54 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by XRPD diffraction peaks at about (2θdegrees±0.2) 7.8, 11.1, 12.5, 19.5 and 23.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by XRPD diffraction peaks at about (2θdegrees±0.2) 7.822, 11.139, 12.5, 19.54 and 23.139 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by XRPD diffraction peaks at about (2θdegrees±0.2) 7.8, 11.1, 12.5, 19.5, 21.1, 23.1, 24.0 and 27.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by XRPD diffraction peaks at about (2θdegrees±0.2) 7.822, 11.139, 12.5, 19.54, 21.062, 23.139, 24.022 and 27.179 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by XRPD diffraction peaks at about (2θdegrees±0.2) 7.8, 11.1, 12.5, 17.1, 17.7, 19.5, 21.1, 23.1, 24.0 and 27.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane, characterized by XRPD diffraction peaks at about (2θdegrees±0.2) 7.822, 11.139, 12.5, 17.135, 17.703, 19.54, 21.062, 23.139, 24.022 and 27.179 is provided.

Figure 12:
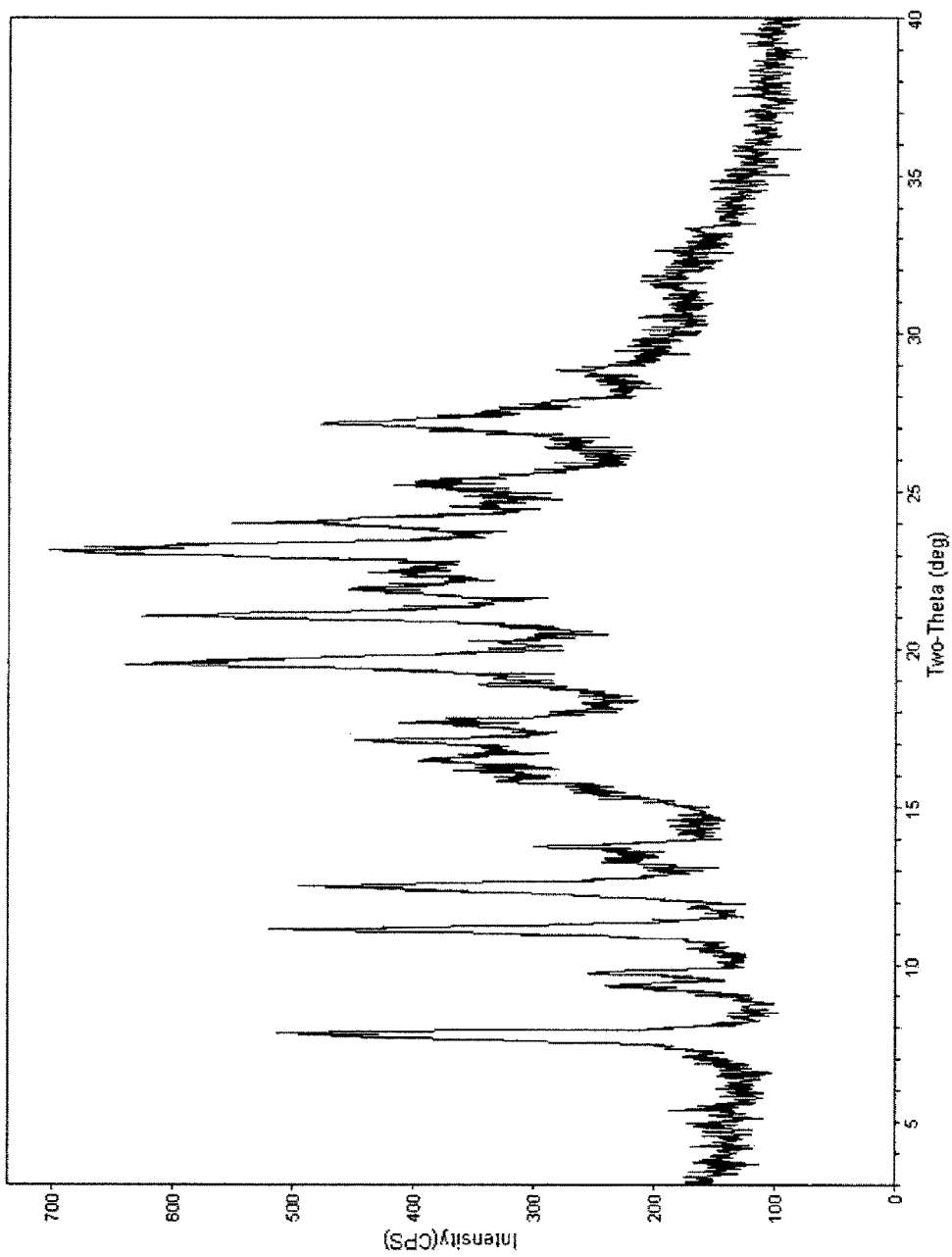
FIG. 12 shows a characteristic XRPD scan of Form D Dioxane.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane which has an XRPD diffraction pattern substantially the same as FIG. 12 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane which is characterized by XRPD diffraction peaks (2θdegrees±0.2) substantially the same as Table 12 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane which is characterized by endotherms at about 109.8° C., 238.2° C. and 250.2° C. and an exotherm at about 170.8° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane which is characterized by endotherms at about 109.8° C., 238.2° C. and 250.2° C. is provided.

Figure 41:
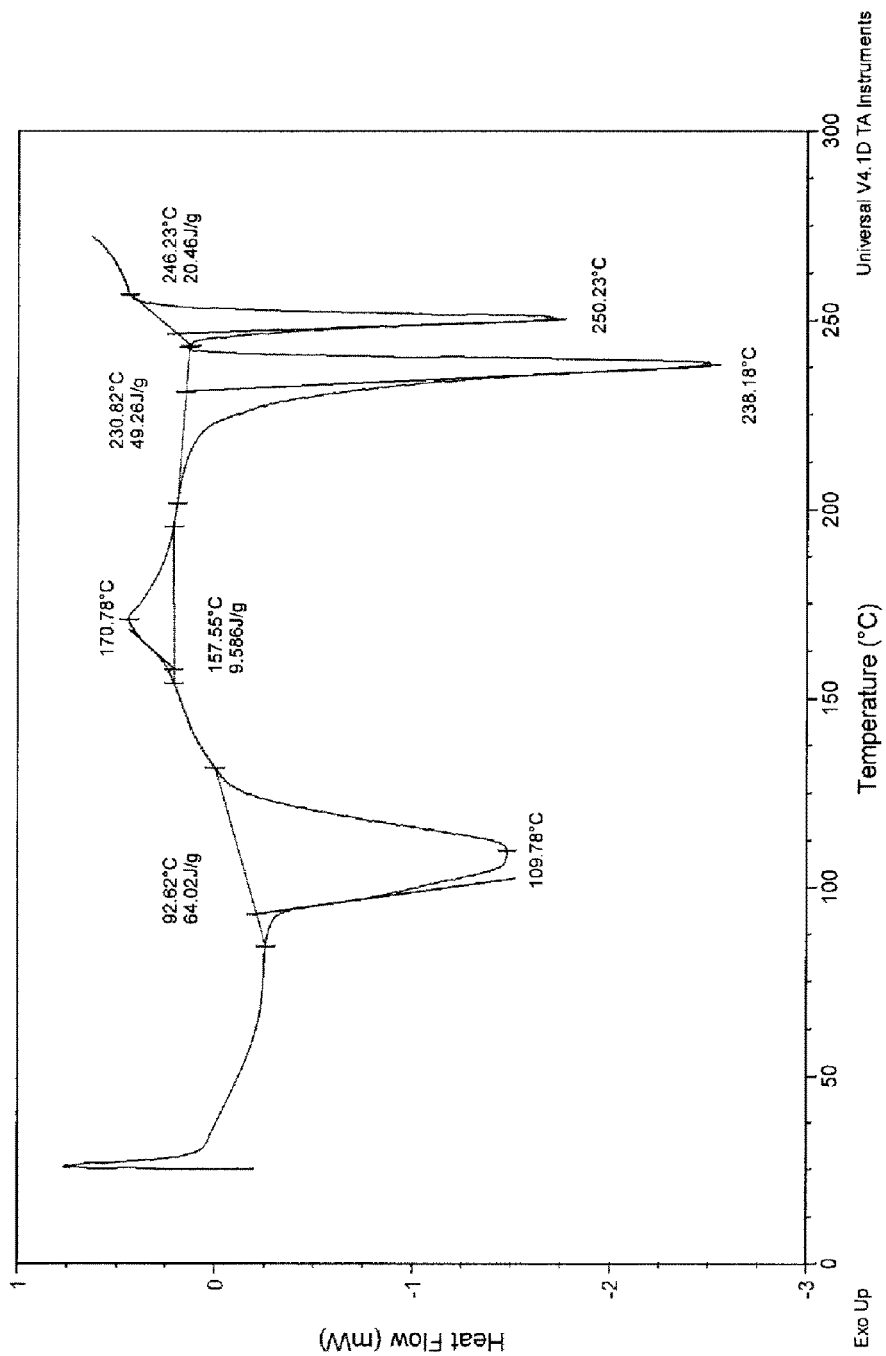
FIG. 41 shows a characteristic DSC scan of Form D Dioxane.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane which is characterized by a DSC scan substantially the same as FIG. 41 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Dioxane comprising:

(a) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and dioxane; and (b) recrystallizing the solid to prepare Form D Dioxane.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone is provided. Form D Acetone can be distinguished by the XRPD diffraction in FIG. 13 and/or peak assignments of the XRPD diffraction of FIG. 13 in Table 13.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by at least one specific XRPD diffraction peak at about (2θdegrees±0.2) 8.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by at least one specific XRPD diffraction peak at about (2θdegrees±0.2) 7.999 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by XRPD diffraction peaks at about (2θdegrees±0.2) 8.0, 17.1, 21.4, 23.6 and 27.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by XRPD diffraction peaks at about (2θdegrees±0.2) 7.999, 17.14, 21.378, 23.561 and 27.482 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by XRPD diffraction peaks at about (2θdegrees±0.2) 8.0, 13.9, 16.1, 17.1, 19.8, 21.4, 23.6 and 27.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by XRPD diffraction peaks at about (2θdegrees±0.2) 7.999, 13.923, 16.101, 17.14, 19.761, 21.378, 23.561 and 27.482 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone, characterized by XRPD diffraction peaks at about (2θdegrees±0.2) 8.0, 9.9, 12.7, 13.9, 16.1, 17.1, 18.0, 19.8, 21.4, 22.1, 23.6, 24.3 and 27.5 is provided. In a further embodiment, a crystalline polymorph N4-(4-([1,2,4]triazolo[1,5-c]pyridin-7-yl oxy)-3-methylphenyl)-N6-(4,4-dimethyl-4,5-dihydrooxazol-2-yl)quinazoline-4,6-diamine Form D Acetone, characterized by XRPD diffraction peaks at about (2θdegrees±0.2) 7.999, 9.856, 12.681, 13.923, 16.101, 17.14, 18, 19.761, 21.378, 22.103, 23.561, 24.259 and 27.482 is provided.

Figure 13:
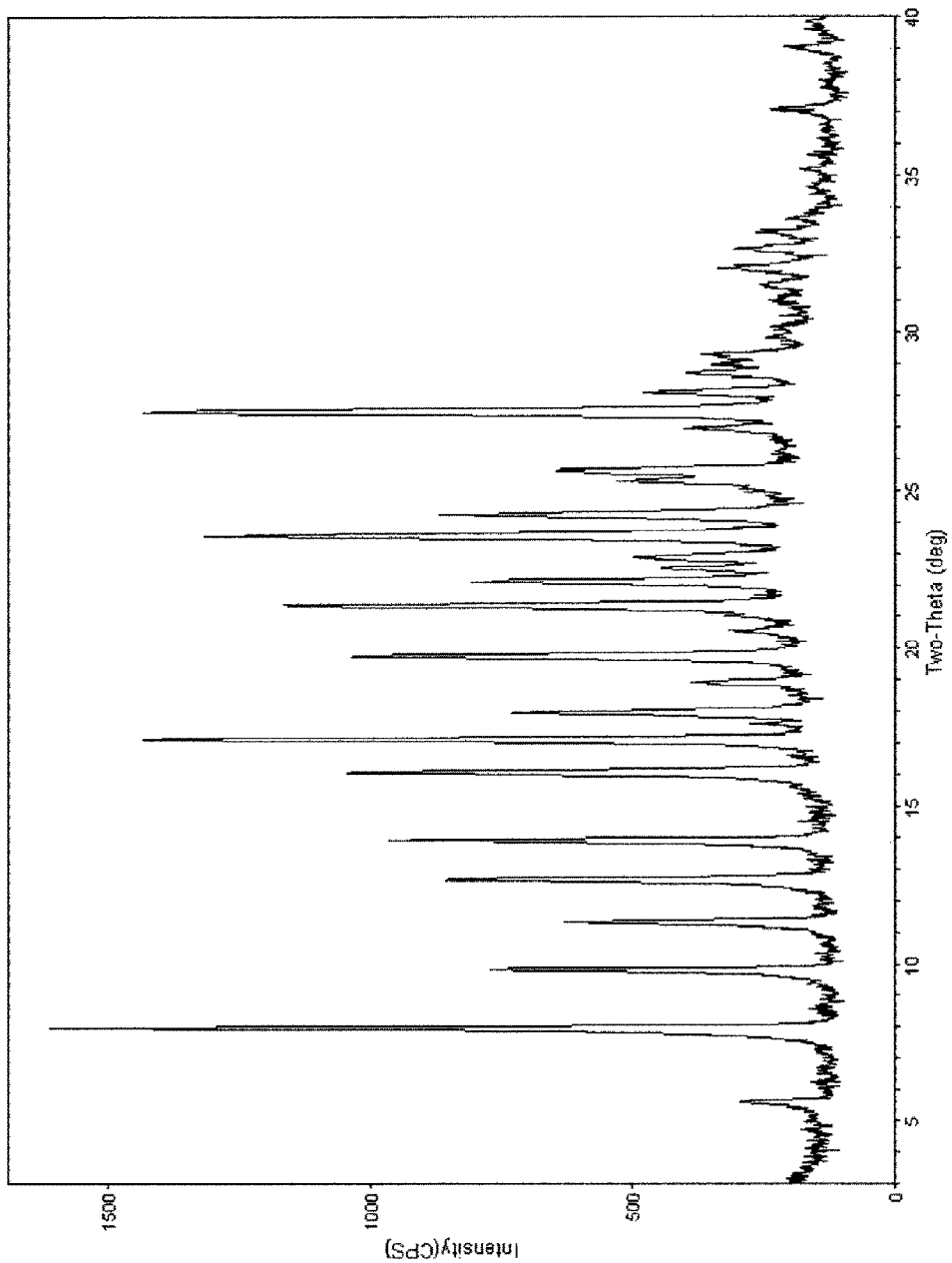
FIG. 13 shows a characteristic XRPD scan of Form D Acetone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone which has an XRPD diffraction pattern substantially the same as FIG. 13 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone which is characterized by XRPD diffraction peaks (2θdegrees±0.2) substantially the same as Table 13 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone which is characterized by endotherms at about 108.5° C. and 235.1° C. is provided.

Figure 42:
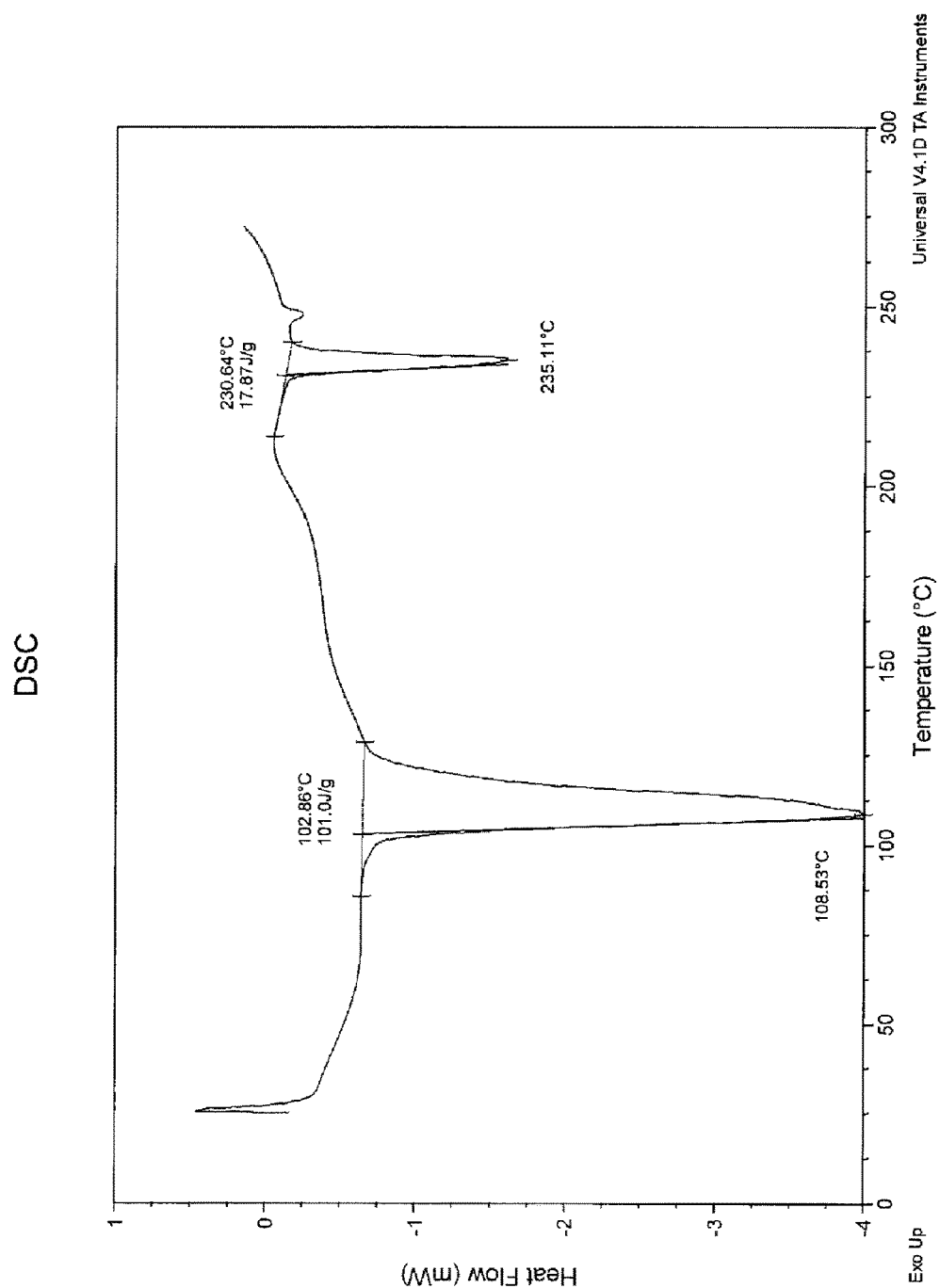
FIG. 42 shows a characteristic DSC scan of Form D Acetone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone which is characterized by a DSC scan substantially the same as FIG. 42 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Acetone comprising:

(a) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E and acetone; and (b) recrystallizing the solid to prepare Form D Acetone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline- 4,6-diamine Form D Propyl Acetate is provided. Form D Propyl Acetate can be distinguished by the XRPD diffraction in FIG. 14 and/or peak assignments of the XRPD diffraction of FIG. 14 in Table 14.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by at least one specific XRPD diffraction peak at about (2θdegrees±0.2) 8.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by at least one specific XRPD diffraction peak at about (2θdegrees±0.2) 7.999 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by XRPD diffraction peaks at about (2θdegrees±0.2) 8.0, 12.7, 16.1, 17.1 and 19.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by XRPD diffraction peaks at about (2θdegrees±0.2) 7.99, 12.719, 16.121, 17.16 and 19.782 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by XRPD diffraction peaks at about (2θdegrees±0.2) 8.0, 12.7, 16.1, 17.1, 19.8, 23.6 and 27.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by XRPD diffraction peaks at about (2θdegrees±0.2) 7.99, 12.719, 16.121, 17.16, 19.782, 23.62 and 27.579 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by XRPD diffraction peaks at about (2θdegrees±0.2) 8.0, 9.8, 12.7, 13.9, 16.1, 17.1, 18.0, 19.8, 21.4, 23.6, 24.3 and 27.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate, characterized by XRPD diffraction peaks at about (2θdegrees±0.2) 7.99, 9.839, 12.719, 13.903, 16.121, 17.16, 18.021, 19.782, 21.42, 23.62, 24.28 and 27.579 is provided.

Figure 14:
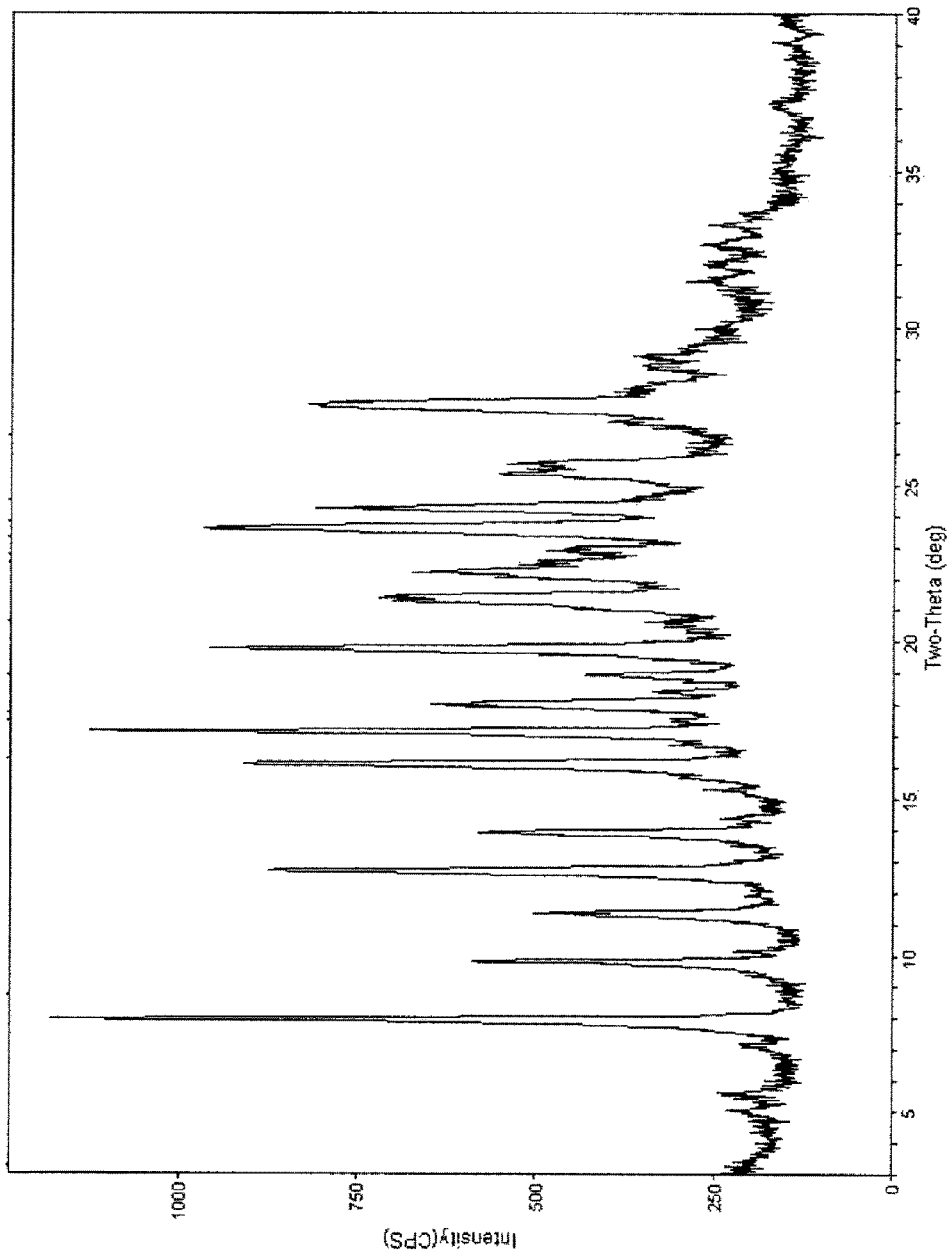
FIG. 14 shows a characteristic XRPD scan of Form D Propyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate which has an XRPD diffraction pattern substantially the same as FIG. 14 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate which is characterized by XRPD diffraction peaks (2θdegrees±0.2) substantially the same as Table 14 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate which is characterized by endotherms at about 119.6° C. and 247.7° C. is provided.

Figure 43:
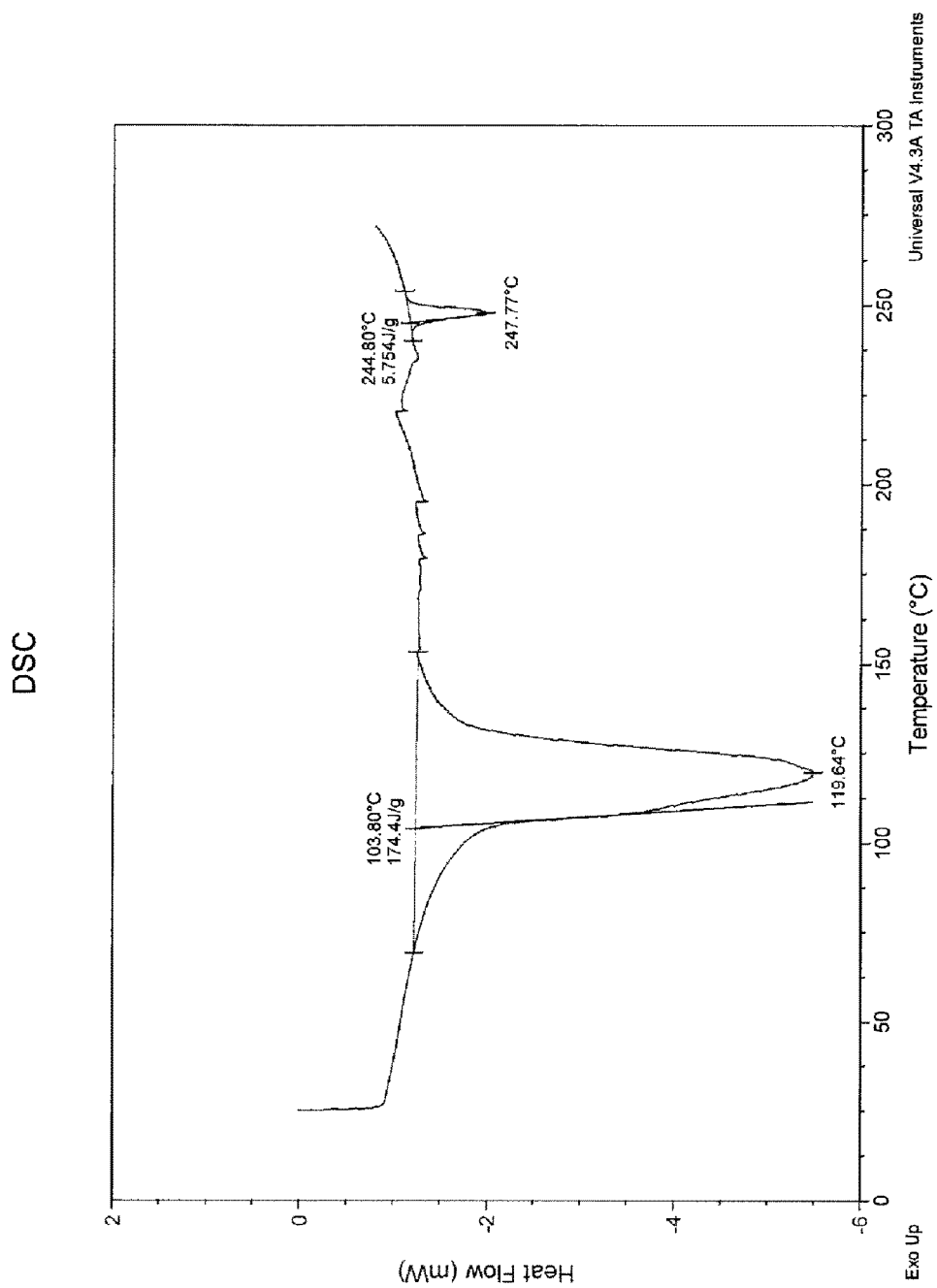
FIG. 43 shows a characteristic DSC scan of Form D Propyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate which is characterized by a DSC scan substantially the same as FIG. 43 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and propyl acetate; and (b) recrystallizing the solid to prepare Form D Propyl Acetate.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

Form E

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E is provided. Form E can be distinguished by the XRPD diffraction in FIG. 15 and/or peak assignments of the XRPD diffraction of FIG. 15 in Table 15.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E, characterized by at least one specific XRPD diffraction peak at about (2θdegrees±0.2) 16.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E, characterized by at least one specific XRPD diffraction peak at about (2θdegrees±0.2) 16.06 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E, characterized by XRPD diffraction peaks at about (2θdegrees±0.2) 8.7, 9.4, 11.9, 16.1 and 23.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E, characterized by XRPD diffraction peaks at about (2θdegrees±0.2) 8.659, 9.353, 11.904, 16.06 and 23.739 is provided.

Figure 15:
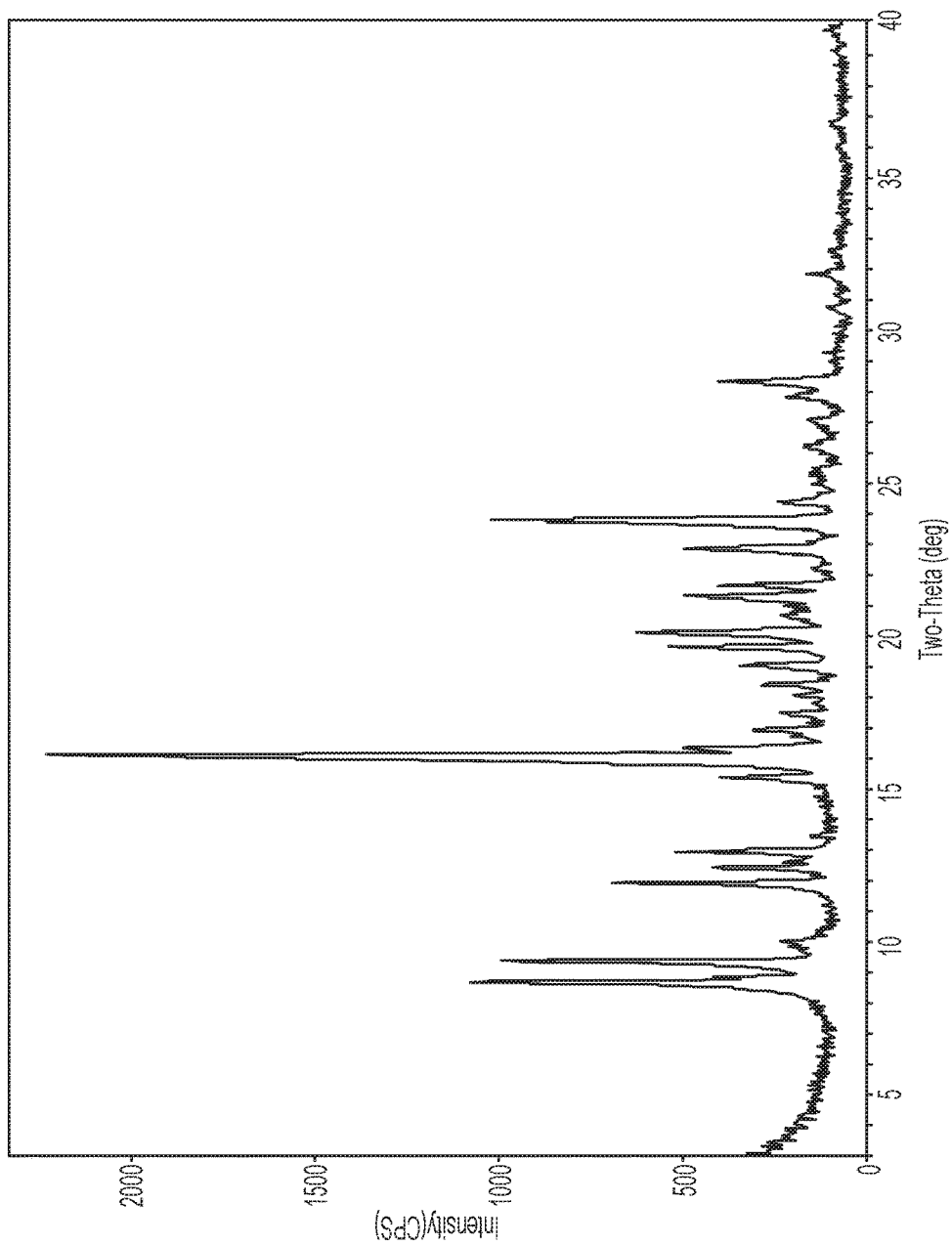
FIG. 15 shows a characteristic XRPD scan of Form E.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E which has an XRPD diffraction pattern substantially the same as FIG. 15 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E which is characterized by XRPD diffraction peaks (2θdegrees±0.2) substantially the same as Table 15 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E which is characterized by endotherms at about 149.7° C. and 253.1° C. is provided.

Figure 44:
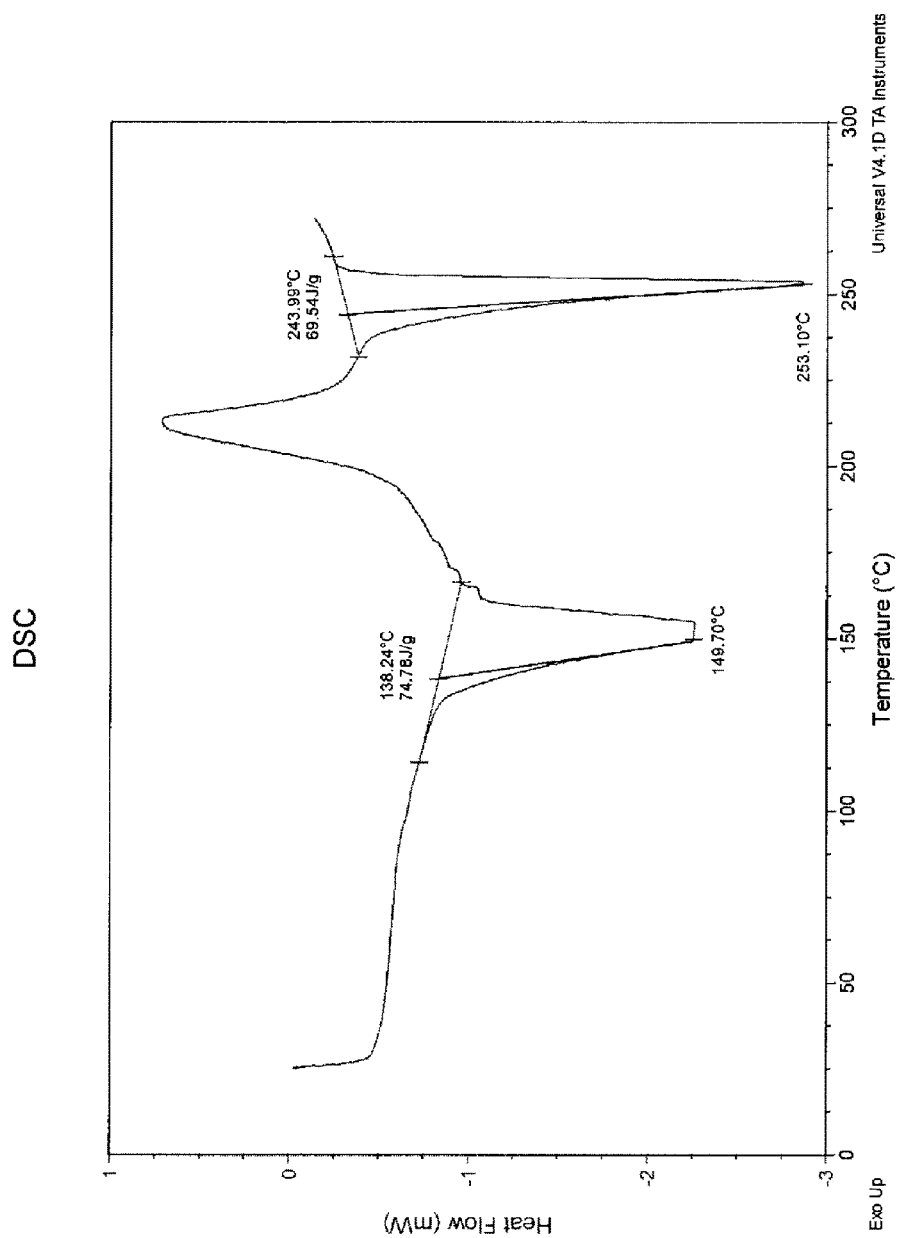
FIG. 44 shows a characteristic DSC scan of Form E.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E which is characterized by a DSC scan substantially the same as FIG. 44 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E comprising:

(a) mixing 1-(4-((4-([1,2,4]triazolo[1,5-a]pyridin-7-yloxy)-3-methyl-phenyl)amino)quinazolin-6-yl)-3-(1-hydroxy-2-methylpropan-2-yl)thiourea in THF under basic conditions;

(b) adding water to the mixture to form an oil of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine;

(c) recovering the product as N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E.

In certain embodiments, the basic conditions in Step (a) are provided by 2.5N NaOH.

Form F

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F is provided. Form F can be distinguished by the XRPD diffraction in FIG. 16 and/or peak assignments of the XRPD diffraction of FIG. 16 in Table 16.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F, characterized by at least one specific XRPD diffraction peak at about (2θdegrees±0.2) 16.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F, characterized by at least one specific XRPD diffraction peak at about (2θdegrees±0.2) 16.56 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F, characterized by XRPD diffraction peaks at about (2θdegrees±0.2) 14.9, 16.6, 16.9, 19.1 and 21.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F, characterized by XRPD diffraction peaks at about (2θdegrees±0.2) 14.899, 16.56, 16.92, 19.098 and 21.18 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F, characterized by XRPD diffraction peaks at about (2θdegrees±0.2) 14.9, 16.6, 16.9, 19.1, 21.2 and 22.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F, characterized by XRPD diffraction peaks at about (2θdegrees±0.2) 14.899, 16.56, 16.92, 19.098, 21.18 and 22.537 is provided.

Figure 16:
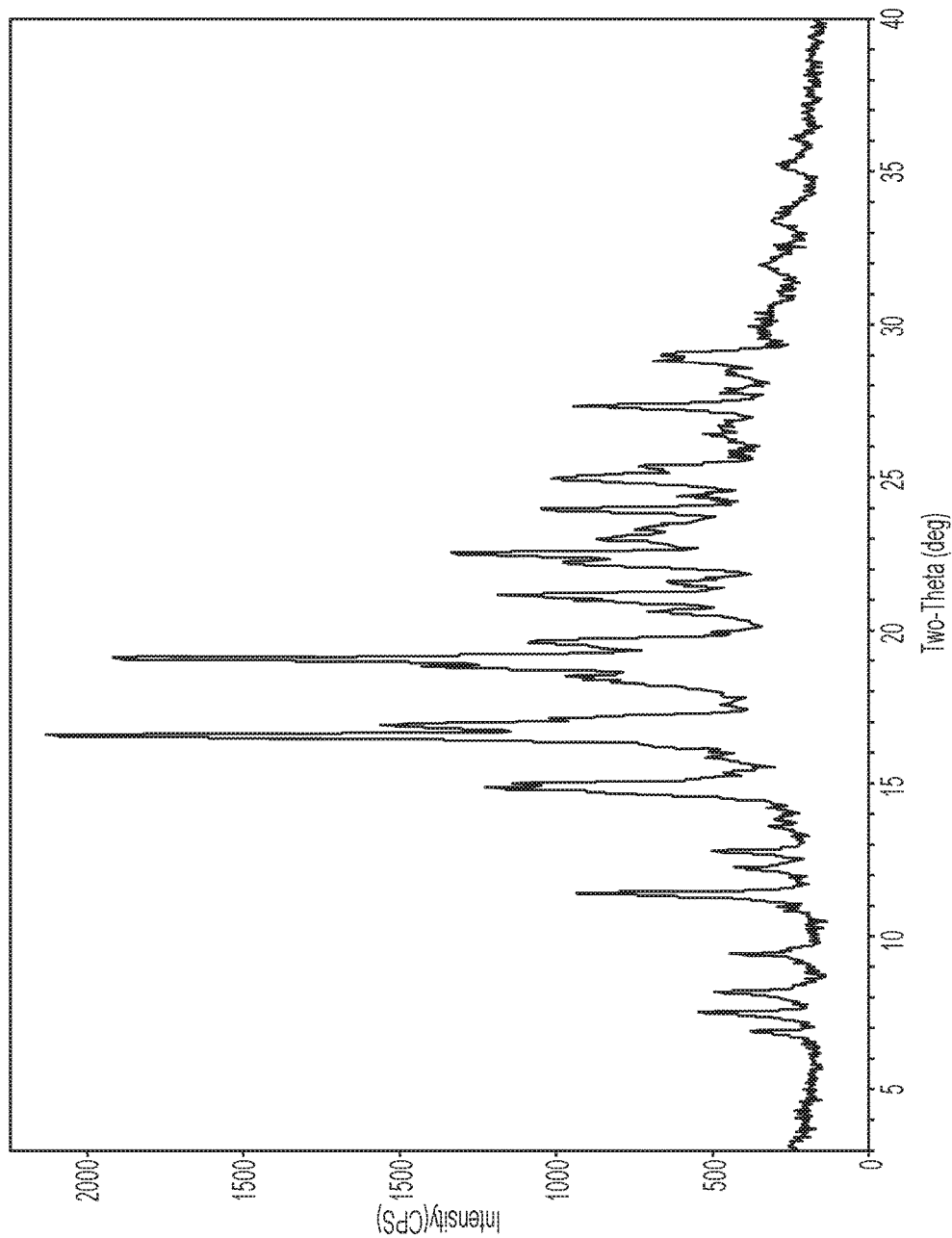
FIG. 16 shows a characteristic XRPD scan of Form F.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F which has an XRPD diffraction pattern substantially the same as FIG. 16 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F which is characterized by XRPD diffraction peaks (2θdegrees±0.2) substantially the same as Table 16 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F which is characterized by endotherms at about 122.7° C., 234.2° C. and 250.5° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F which is characterized by endotherms at about 122.7° C. and 250.5° C. is provided.

Figure 45:
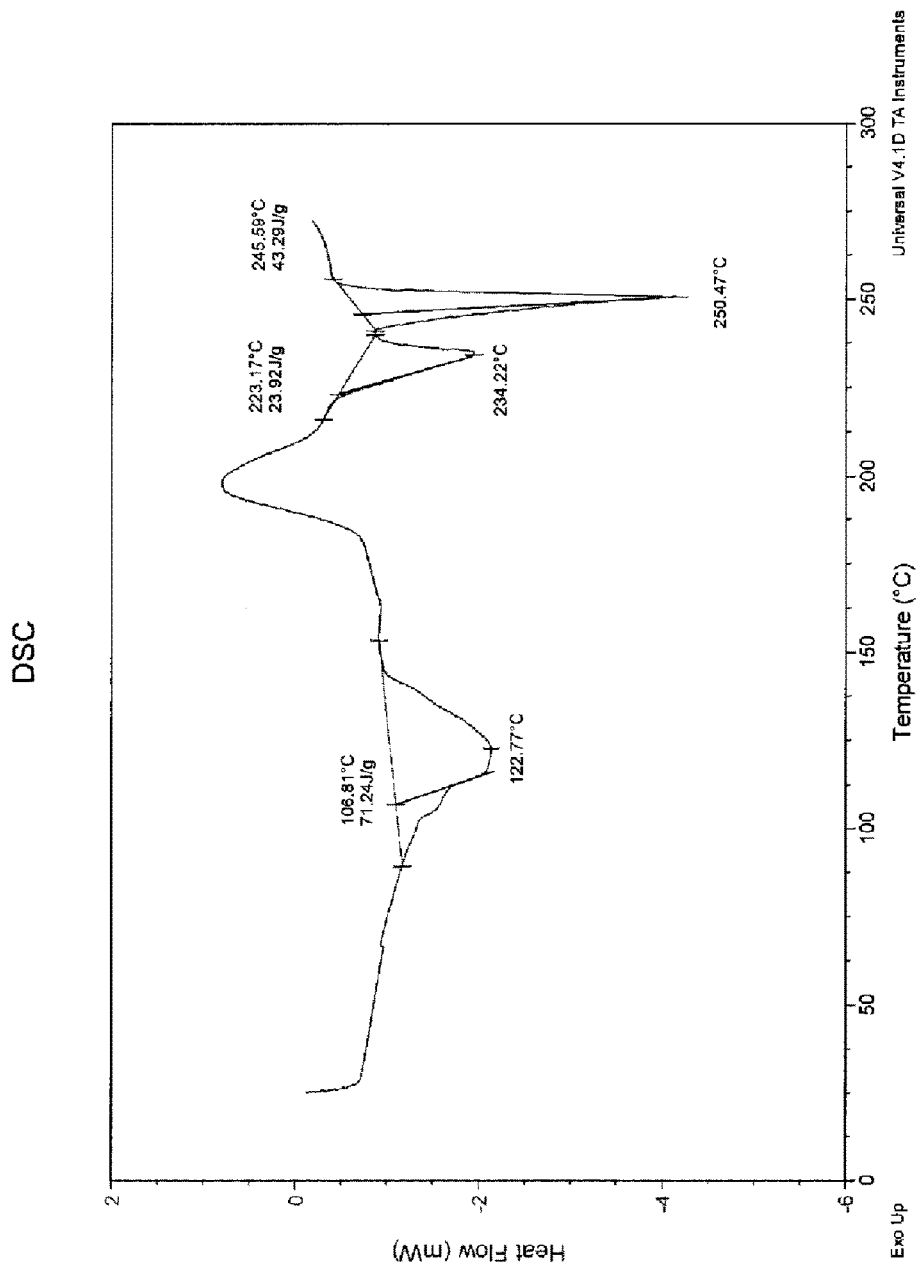
FIG. 45 shows a characteristic DSC scan of Form F.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F which is characterized by a DSC scan substantially the same as FIG. 45 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form F comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E and ethyl acetate; and (b) recrystallizing the solid to prepare Form F.

Form G

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G is provided. Form G forms isomorphic solvates. Form G can be distinguished by the representative XRPD diffraction in FIGS. 17 to 20 and/or representative peak assignments of the XRPD diffraction of FIGS. 17 to 20 in Tables 17 to 20.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.4) 7.8 and 23.1 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.3) 7.8 and 23.2 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peak at about (2θdegrees±0.2) 7.8 is provided.

In certain embodiments, a crystalline polymorph N4-(4-([1,2,4]triazolo[1,5-a]pyridin-7-yloxy)-3-methylphenyl)-

N6-(4,4-dimethyl-4,5-dihydrooxazol-2-yl)quinazoline-4,6-diamine Form G, characterized by XRPD diffraction peaks at about (2θdegrees±0.4) 7.8, 11.1 and 23.1 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.3) 7.8, 11.2 and 23.2 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.2) 7.8 and 11.2 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.5) 7.8, 8.2, 9.4, 11.1, 16.6, 23.1, 24.1 and 27.8 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.2) 7.8, 8.2, 9.4 and 16.6 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.3) 7.8, 8.1, 9.3, 11.2, 16.6, 23.2, 24.3 and 27.6 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.2) 7.8, 8.1, 9.3, 11.2 and 16.6 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.5) 5.6, 7.8, 8.2, 9.4, 11.1, 12.7, 15.6, 16.6, 20.0, 21.0, 23.1, 23.4, 24.1 and 27.8 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.2) 5.6, 7.8, 8.2, 9.4, 12.7 and 16.6 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.3) 5.6, 7.8, 8.1, 9.3, 11.2, 12.7, 15.7, 16.6, 20.0, 21.2, 23.2, 23.5, 24.3 and 27.6 is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G, characterized by XRPD diffraction peaks at about (2θdegrees±0.2) 5.6, 7.8, 8.1, 9.3, 11.2, 12.7, 16.6 and 21.2 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G comprising:

(a1) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran and 20:80 THF:water, or (a2) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and a solvent selected from isopropyl acetate and MIBK, and (b) recrystallizing the solid to prepare Form G; or (c) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A and tetrahydrofuran, (d) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and THF, and (e) recrystallizing the solid to prepare Form G.

In certain embodiments, the solution in Step (d) is created by heating the mixture of Step (c) to reflux.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a2).

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran is provided. Form G hemi-Tetrahydrofuran can be distinguished by the XRPD diffraction in FIG. 17 and/or peak assignments of the XRPD diffraction of FIG. 17 in Table 17.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran, characterized by at least one specific XRPD diffraction peak at about (2θdegrees±0.2) 23.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran, characterized by at least one specific XRPD diffraction peak at about (2θdegrees±0.2) 23.079 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran, characterized by XRPD diffraction peaks at about (2θdegrees±0.2) 7.7, 11.1, 12.3, 23.1 and 24.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran, characterized by XRPD diffraction peaks at about (2θdegrees±0.2) 7.719, 11.102, 12.281, 23.079 and 24.099 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran, characterized by XRPD diffraction peaks at about (2θdegrees±0.2) 7.7, 11.1, 12.3, 23.1, 24.1 and 27.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran, characterized by XRPD diffraction peaks at about (2θdegrees±0.2) 7.719, 11.102, 12.281, 23.079, 24.099 and 27.503 is provided.

Figure 17:
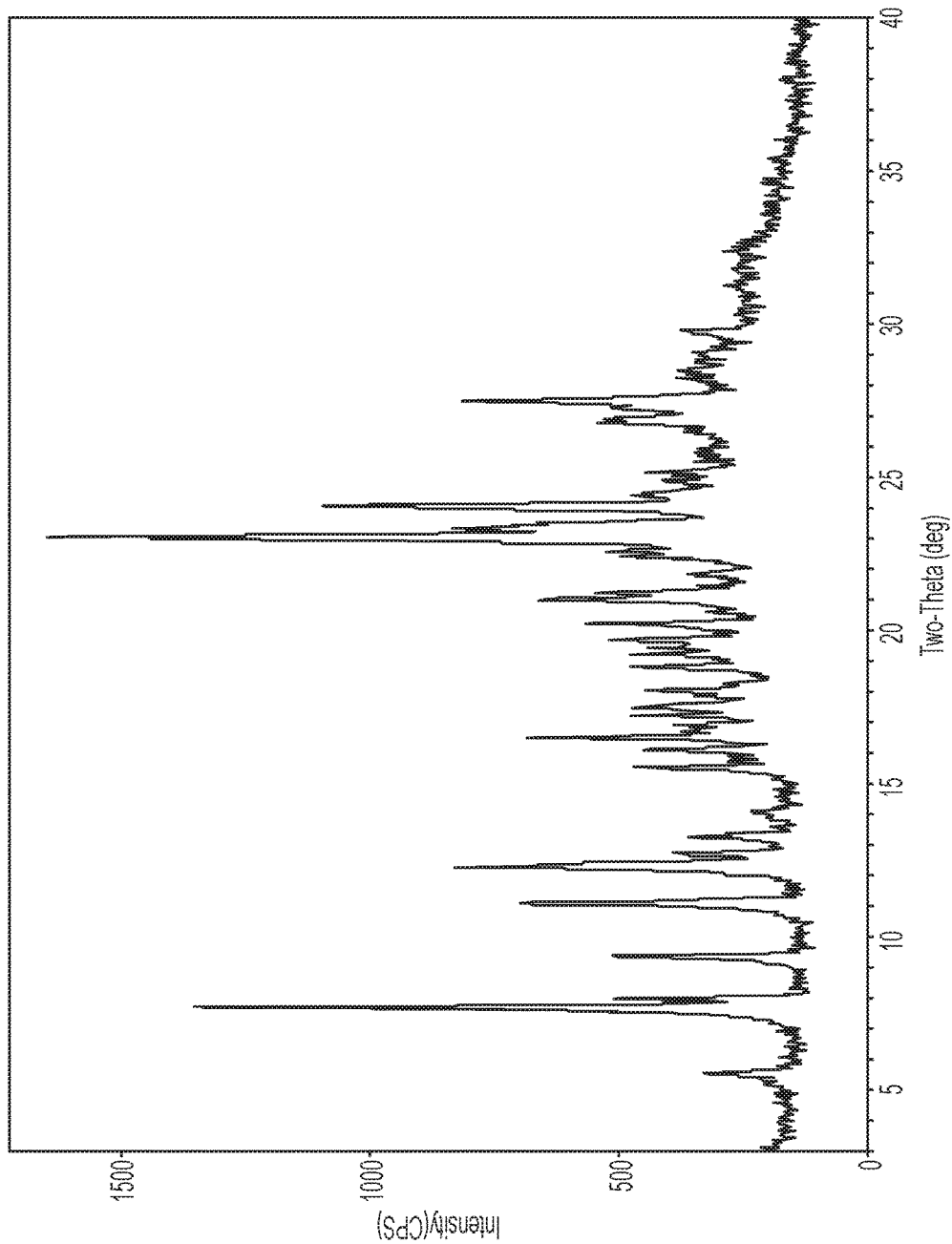
FIG. 17 shows a characteristic XRPD scan of Form G hemi-Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran which has an XRPD diffraction pattern substantially the same as FIG. 17 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran which is characterized by XRPD diffraction peaks (2θdegrees±0.2) substantially the same as Table 17 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran which is characterized by endotherms at about 106.1° C. and 232.3° C. is provided.

Figure 46:
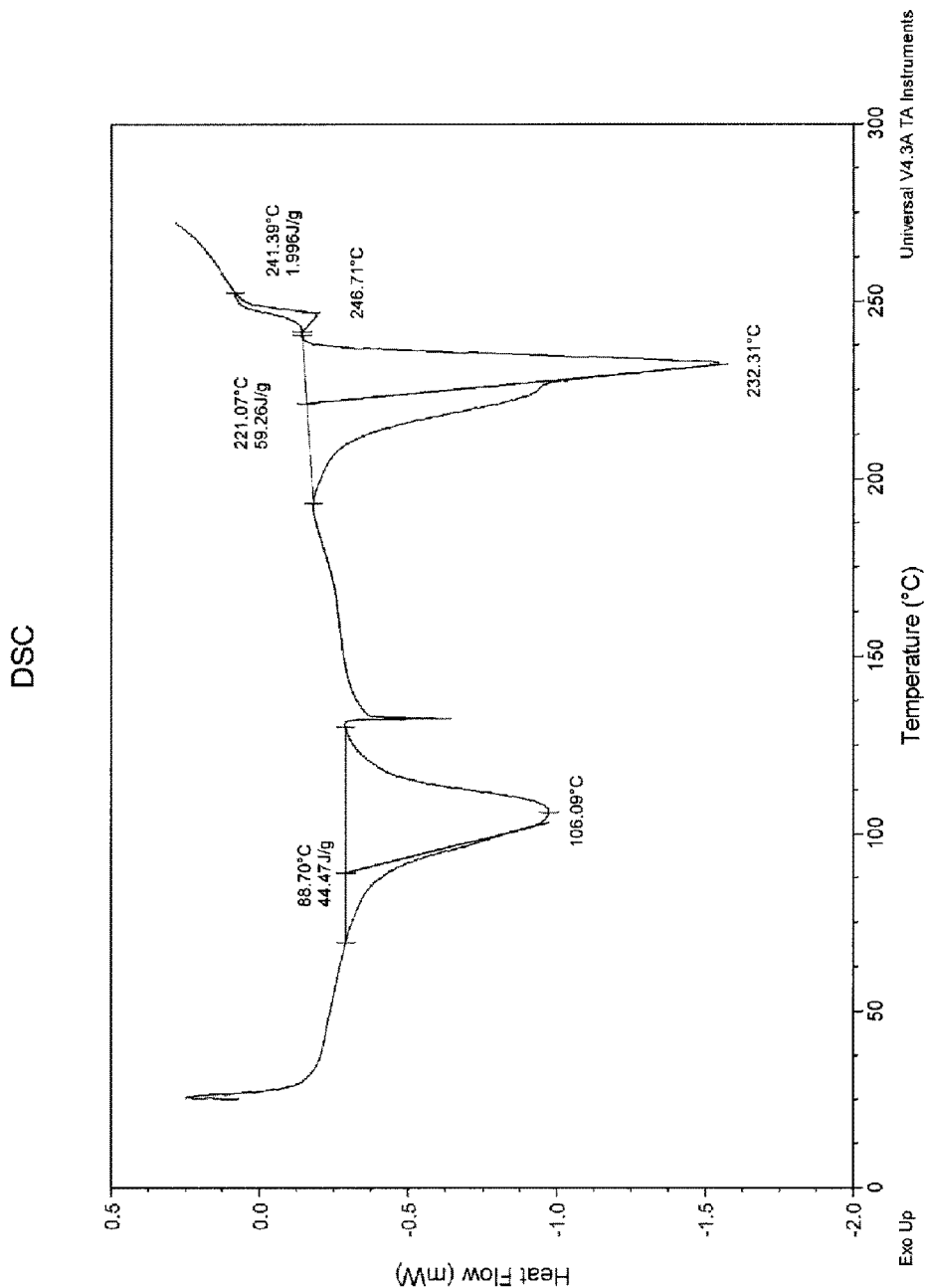
FIG. 46 shows a characteristic DSC scan of Form G hemi-Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran which is characterized by a DSC scan substantially the same as FIG. 46 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form G mono-Tetrahydrofuran and 20:80 THF:water; and (b) recrystallizing the solid to prepare Form G hemi-Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran is provided. Form G mono-Tetrahydrofuran can be distinguished by the XRPD diffraction in FIG. 18 and/or peak assignments of the XRPD diffraction of FIG. 18 in Table 18.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran, characterized by at least one specific XRPD diffraction peak at about (2θdegrees±0.2) 23.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran, characterized by at least one specific XRPD diffraction peak at about (2θdegrees±0.2) 23.022 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran, characterized by XRPD diffraction peaks at about (2θdegrees±0.2) 7.7, 11.1, 12.4, 23.0 and 24.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihy-drooxazol-2-yl)quinazoline-4,6-diamine Form G mono-Tetrahydrofuran, characterized by XRPD diffraction peaks at about (2θdegrees±0.2) 7.72, 11.137, 12.401, 23.022 and 24.042 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran, characterized by XRPD diffraction peaks at about (2θdegrees±0.2) 7.7, 8.0, 9.4, 11.1, 12.4, 16.6, 21.0, 23.0, 23.4, 24.0 and 27.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran, characterized by XRPD diffraction peaks at about (2θdegrees±0.2) 7.72, 8.003, 9.417, 11.137, 12.401, 16.599, 21.017, 23.022, 23.397, 24.042 and 27.482 is provided.

Figure 18:
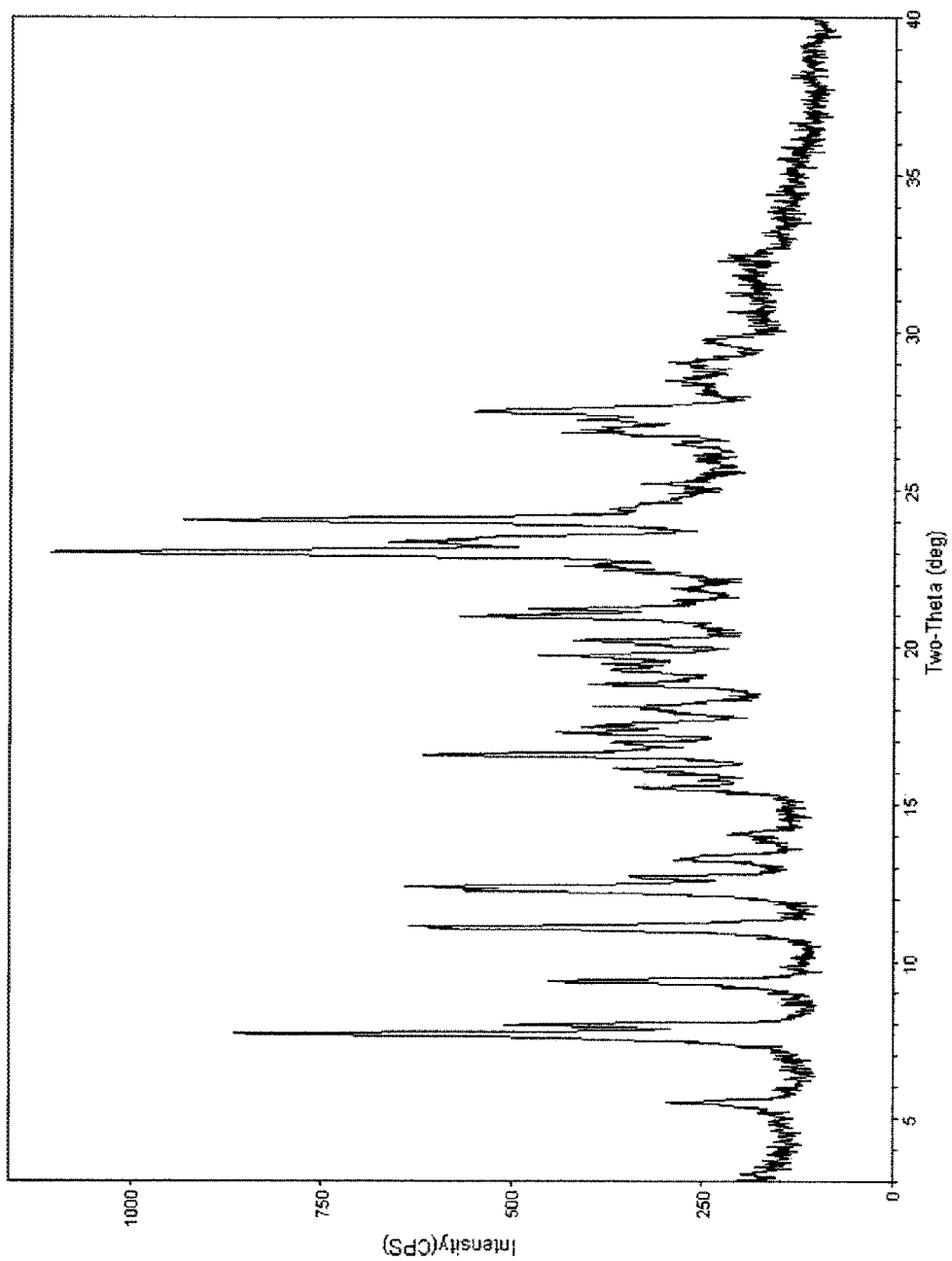
FIG. 18 shows a characteristic XRPD scan of Form G mono-Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran which has an XRPD diffraction pattern substantially the same as FIG. 18 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran which is characterized by XRPD diffraction peaks (2θdegrees±0.2) substantially the same as Table 18 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran which is characterized by endotherms at about 113.2° C. and 232.3° C. is provided.

Figure 47:
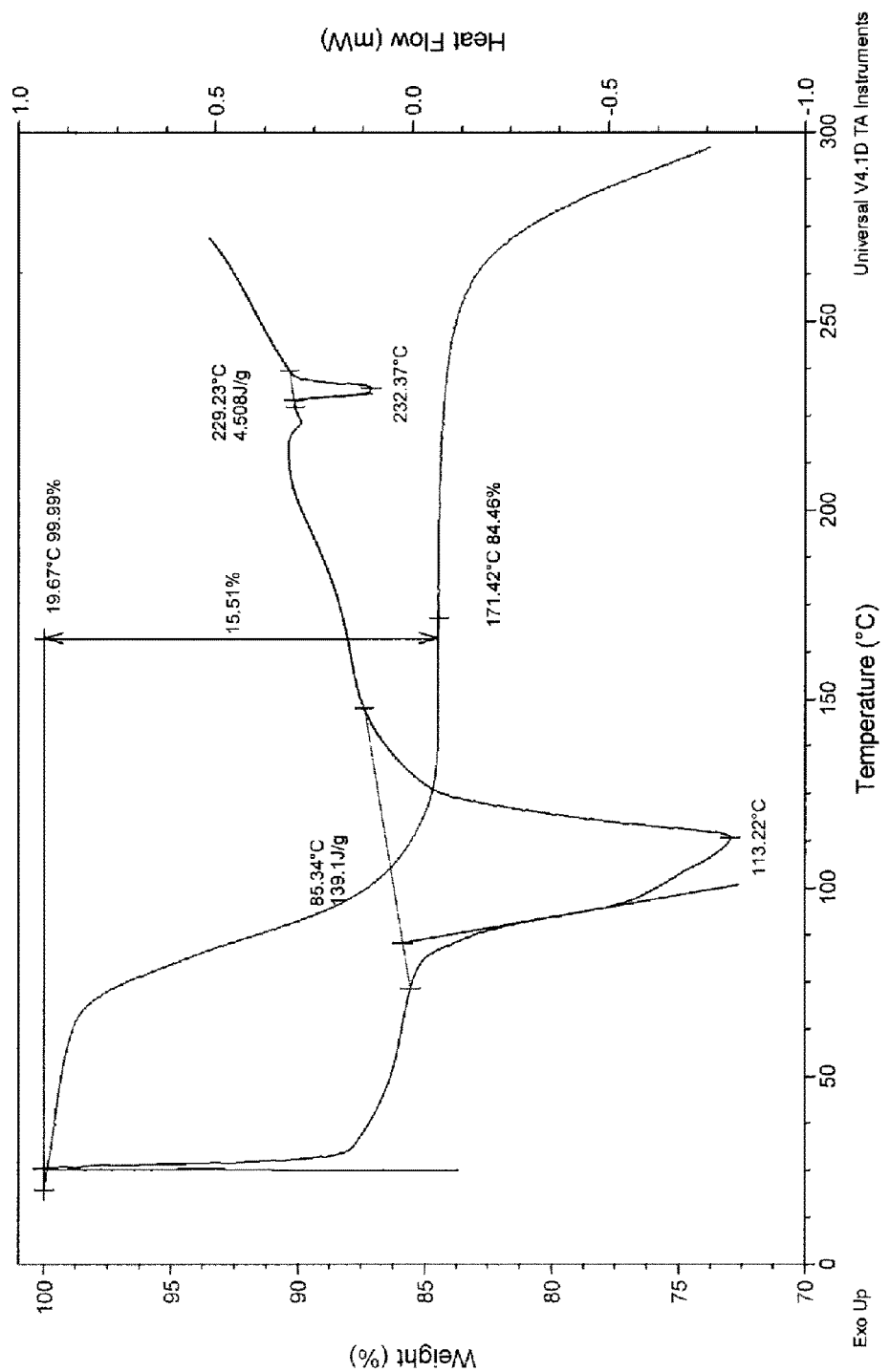
FIG. 47 shows a characteristic DSC scan with a thermal gravimetric analysis ("TGA") overlay of Form G mono-Tetrahydrofuran.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran which is characterized by a DSC scan substantially the same as FIG. 47 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran comprising:

(a) mixing N4-(4-([1,2,4]triazolo[1, 5-a]pyridin-7-yloxy)-3-methylphenyl)-N6-(4,4-dimethyl-4,5-dihydrooxazol-2-yl)quinazoline-4,6-diamine Form A and tetrahydrofuran;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and THF; and (c) recrystallizing the solid to prepare Form G mono-Tetrahydrofuran.

In certain embodiments, the solution in Step (b) is created by heating the mixture of Step (a) to reflux.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate is provided. Form G Isopropyl Acetate can be distinguished by the XRPD diffraction in FIG. 19 and/or peak assignments of the XRPD diffraction of FIG. 19 in Table 19.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by at least one specific XRPD diffraction peak at about (2θdegrees±0.2) 23.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by at least one specific XRPD diffraction peak at about (2θdegrees±0.2) 23.438 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by XRPD diffraction peaks at about (2θdegrees±0.2) 7.8, 8.3, 11.4, 13.2 and 23.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by XRPD diffraction peaks at about (2θdegrees±0.2) 7.803, 8.299, 11.398, 13.18 and 23.438 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by XRPD diffraction peaks at about (2θdegrees±0.2) 7.8, 8.3, 9.4, 11.4, 13.2, 16.6, 23.4 and 24.4 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by XRPD diffraction peaks at about (2θdegrees±0.2) 7.803, 8.299, 9.361, 11.398, 13.18, 16.64, 23.438 and 24.381 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by XRPD diffraction peaks at about (2θdegrees±0.2) 7.8, 8.3, 9.4, 11.4, 12.7, 13.2, 16.6, 18.1, 19.6, 20.0, 21.7, 23.4, 24.4 and 27.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate, characterized by XRPD diffraction peaks at about (2θdegrees±0.2) 7.803, 8.299, 9.361, 11.398, 12.7, 13.18, 16.64, 18.099, 19.639, 19.979, 21.738, 23.438, 24.381 and 27.821 is provided.

Figure 19:
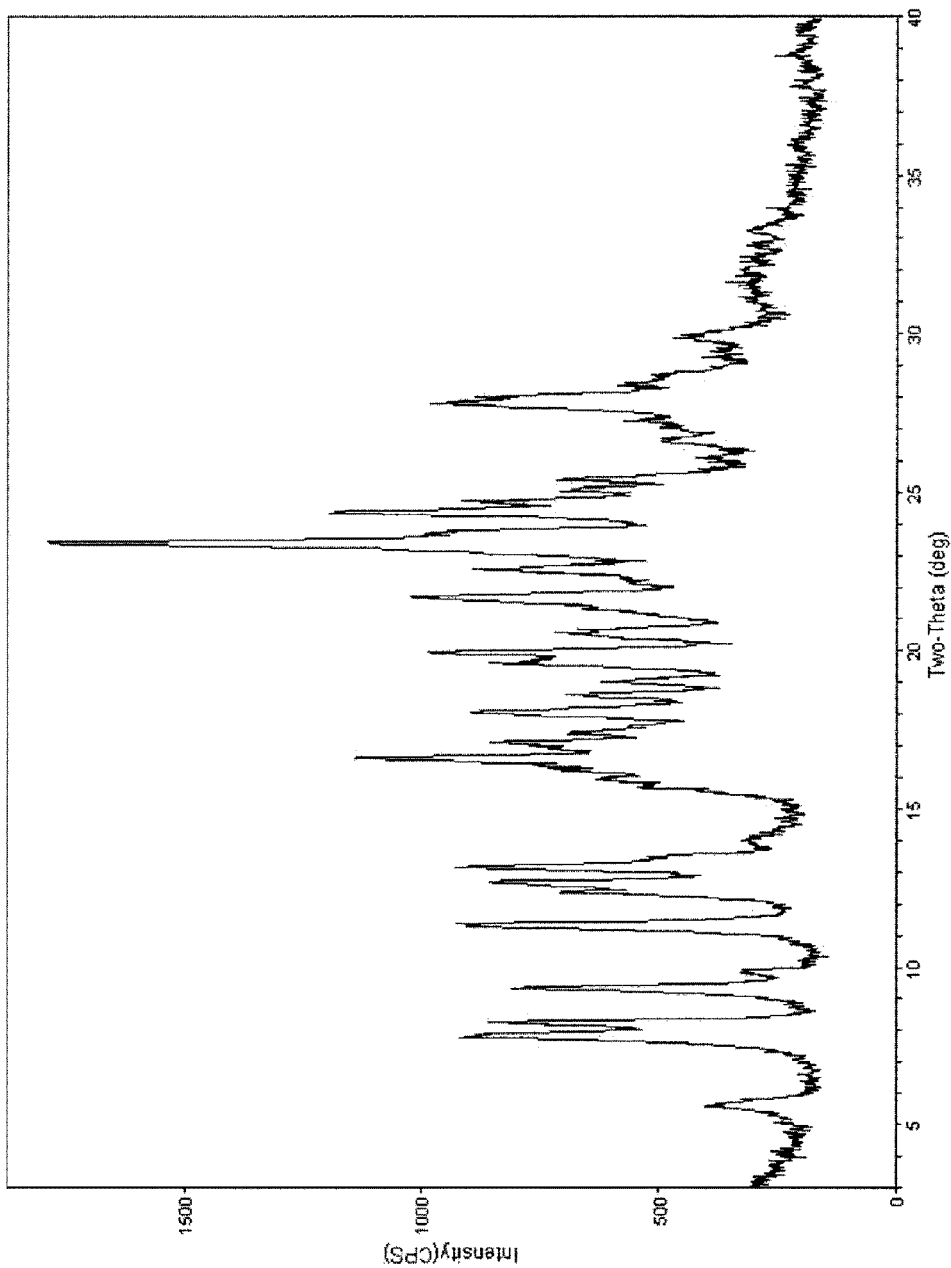
FIG. 19 shows a characteristic XRPD scan of Form G Isopropyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate which has an XRPD diffraction pattern substantially the same as FIG. 19 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate which is characterized by XRPD diffraction peaks (2θdegrees±0.2) substantially the same as Table 19 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate which is characterized by endotherms at about 123.3° C., 221.3° C. and 237.0° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate which is characterized by endotherms at about 123.3° C. and 237.0° C. is provided.

Figure 48:
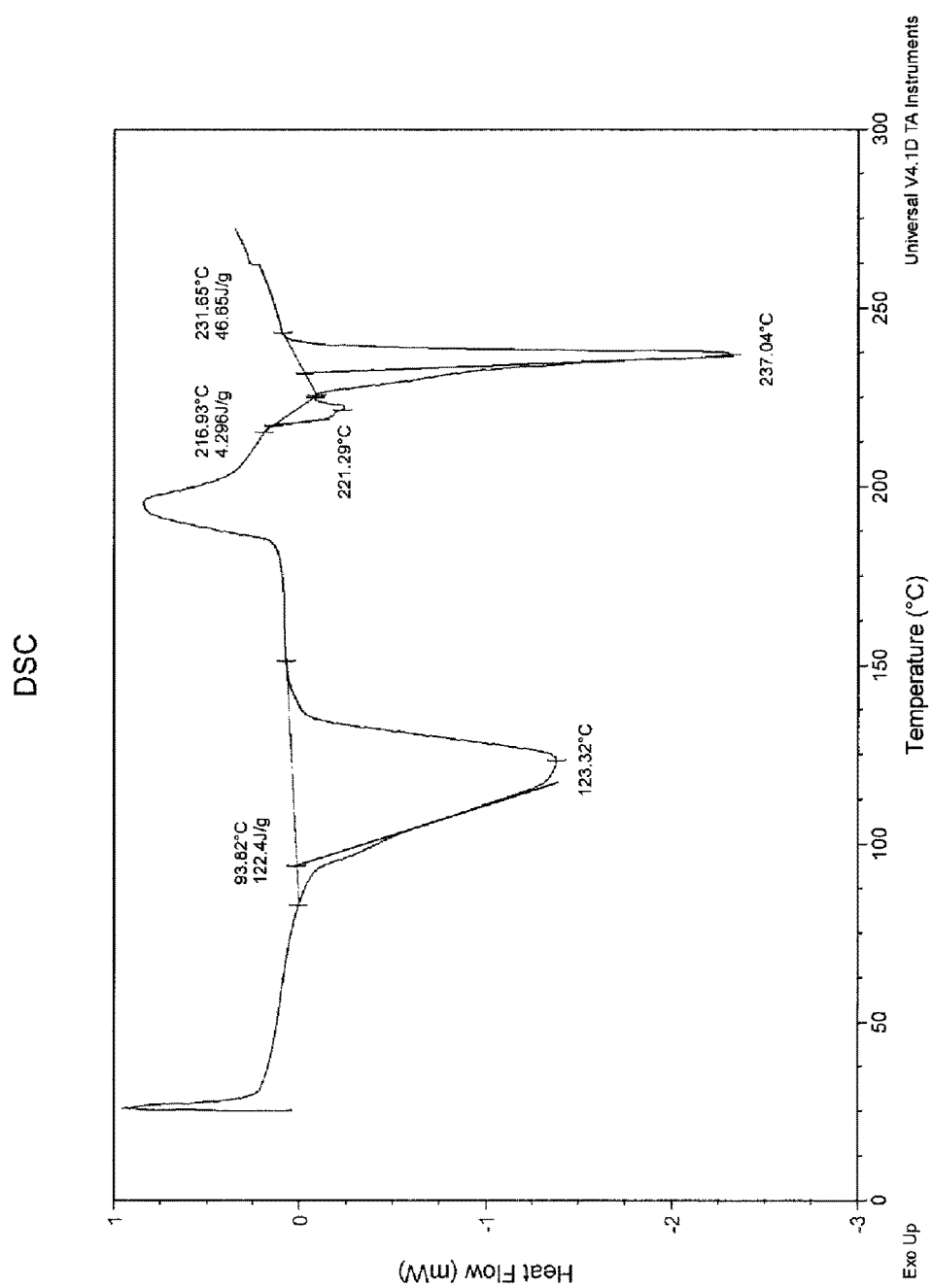
FIG. 48 shows a characteristic DSC scan of Form G Isopropyl Acetate.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate which is characterized by a DSC scan substantially the same as FIG. 48 is provided.

Certain embodiments provide a process for preparing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form G Isopropyl Acetate comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine and isopropyl acetate; and (b) recrystallizing the solid to prepare Form G Isopropyl Acetate.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone is provided. Form G Methyl Isobutyl Ketone can be distinguished by the XRPD diffraction in FIG. 20 and/or peak assignments of the XRPD diffraction of FIG. 20 in Table 20.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by at least one specific XRPD diffraction peak at about (2θdegrees±0.2) 23.3 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by at least one specific XRPD diffraction peak at about (2θdegrees±0.2) 23.28 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by XRPD diffraction peaks at about (2θdegrees±0.2) 7.8, 8.2, 11.2, 16.5 and 23.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by XRPD diffraction peaks at about (2θdegrees±0.2) 7.78, 8.217, 11.239, 16.503 and 23.28 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by XRPD diffraction peaks at about (2θdegrees±0.2) 7.8, 8.2, 9.3, 11.2, 13.1, 16.5, 19.9, 21.4, 23.2, 24.6 and 27.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by XRPD diffraction peaks at about (2θdegrees±0.2) 7.78, 8.217, 9.298, 11.239, 13.079, 16.503, 19.858, 21.442, 23.28, 24.562 and 27.759 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by XRPD diffraction peaks at about (2θdegrees±0.2) 7.8, 8.2, 9.3, 11.2, 12.3, 12.6, 13.1, 16.5, 19.9, 21.4, 23.2, 23.6, 24.6 and 27.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone, characterized by XRPD diffraction peaks at about (2θdegrees±0.2) 7.78, 8.217, 9.298, 11.239, 12.341, 12.575, 13.079, 16.503, 19.858, 21.442, 23.28, 23.619, 24.562 and 27.759 is provided.

Figure 20:
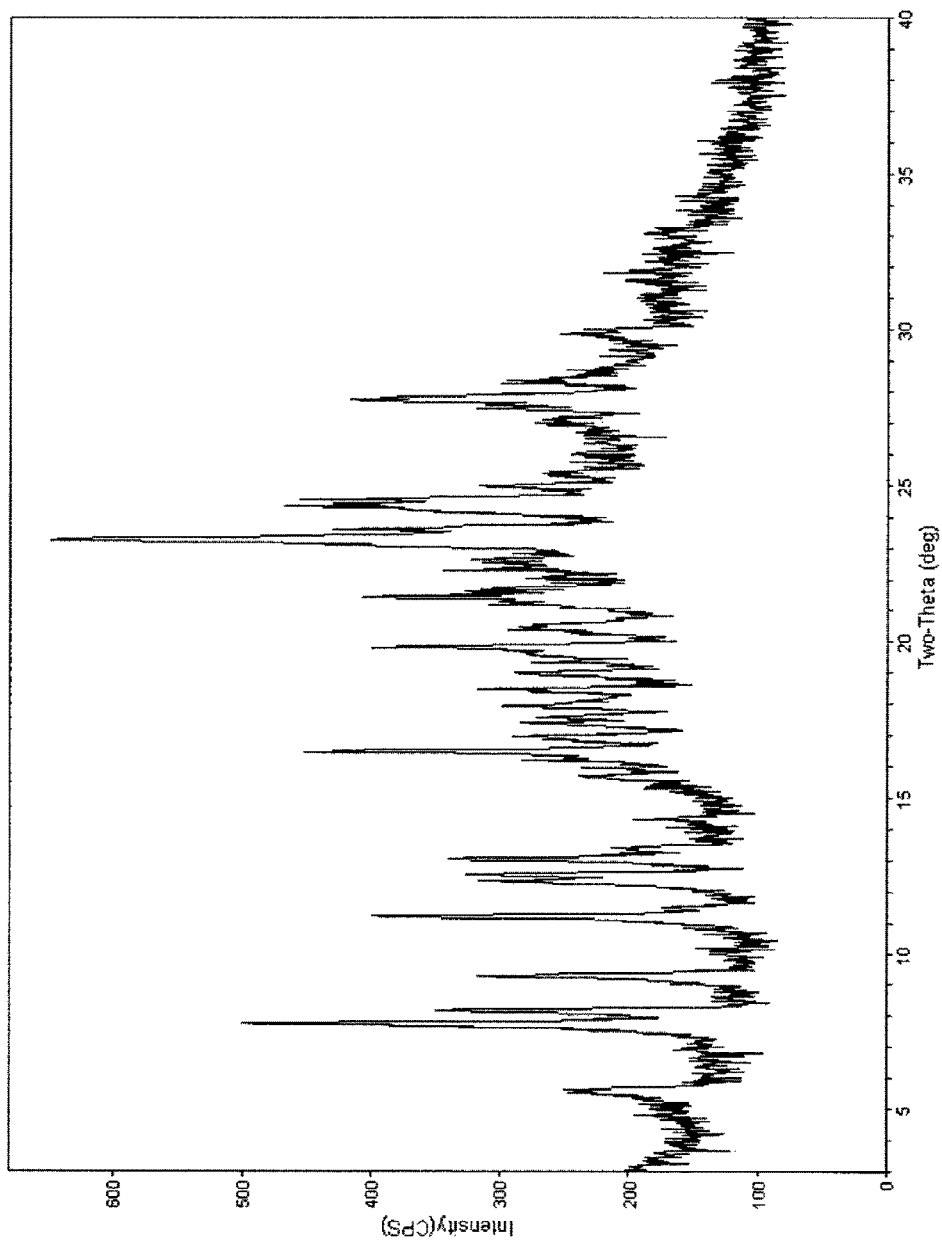
FIG. 20 shows a characteristic XRPD scan of Form G Methyl Isobutyl Ketone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone which has an XRPD diffraction pattern substantially the same as FIG. 20 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone which is characterized by XRPD diffraction peaks (2θdegrees±0.2) substantially the same as Table 20 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone which is characterized by endotherms at about 102.2° C., 234.8° C. and 251.4° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone which is characterized by endotherms at about 234.8° C. and 251.4° C. is provided.

Figure 49:
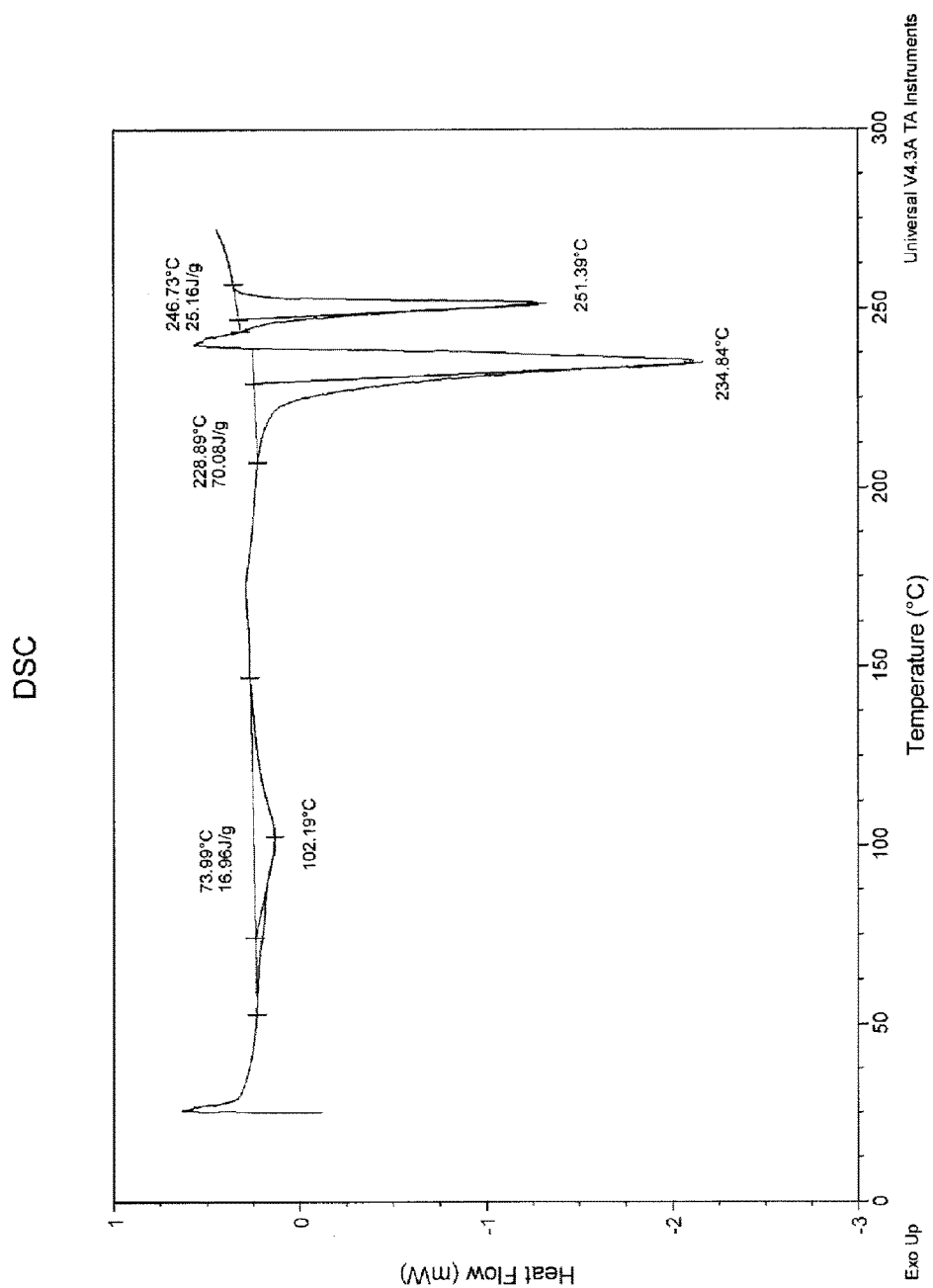
FIG. 49 shows a characteristic DSC scan of Form G Methyl Isobutyl Ketone.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone which is characterized by a DSC scan substantially the same as FIG. 49 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone comprising:
(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and MIBK; and
(b) recrystallizing the solid to prepare Form G Methyl Isobutyl Ketone.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

Form H

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H is provided. In certain embodiments, a substantially pure crystalline polymorph N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form H is provided. Form H can be distinguished by the XRPD diffraction in FIG. 21 and/or peak assignments of the XRPD diffraction of FIG. 21 in Table 21.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H, characterized by at least one specific XRPD diffraction peak at about (2θdegrees±0.2) 11.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H, characterized by at least one specific XRPD diffraction peak at about (2θdegrees±0.2) 11.18 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H, characterized by XRPD diffraction peaks at about (2θdegrees±0.2) 11.2, 16.1, 19.6, 22.0 and 25.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H, characterized by XRPD diffraction peaks at about (2θdegrees±0.2) 11.18, 16.08, 19.58, 22.04 and 25.501 is provided.

Figure 21:
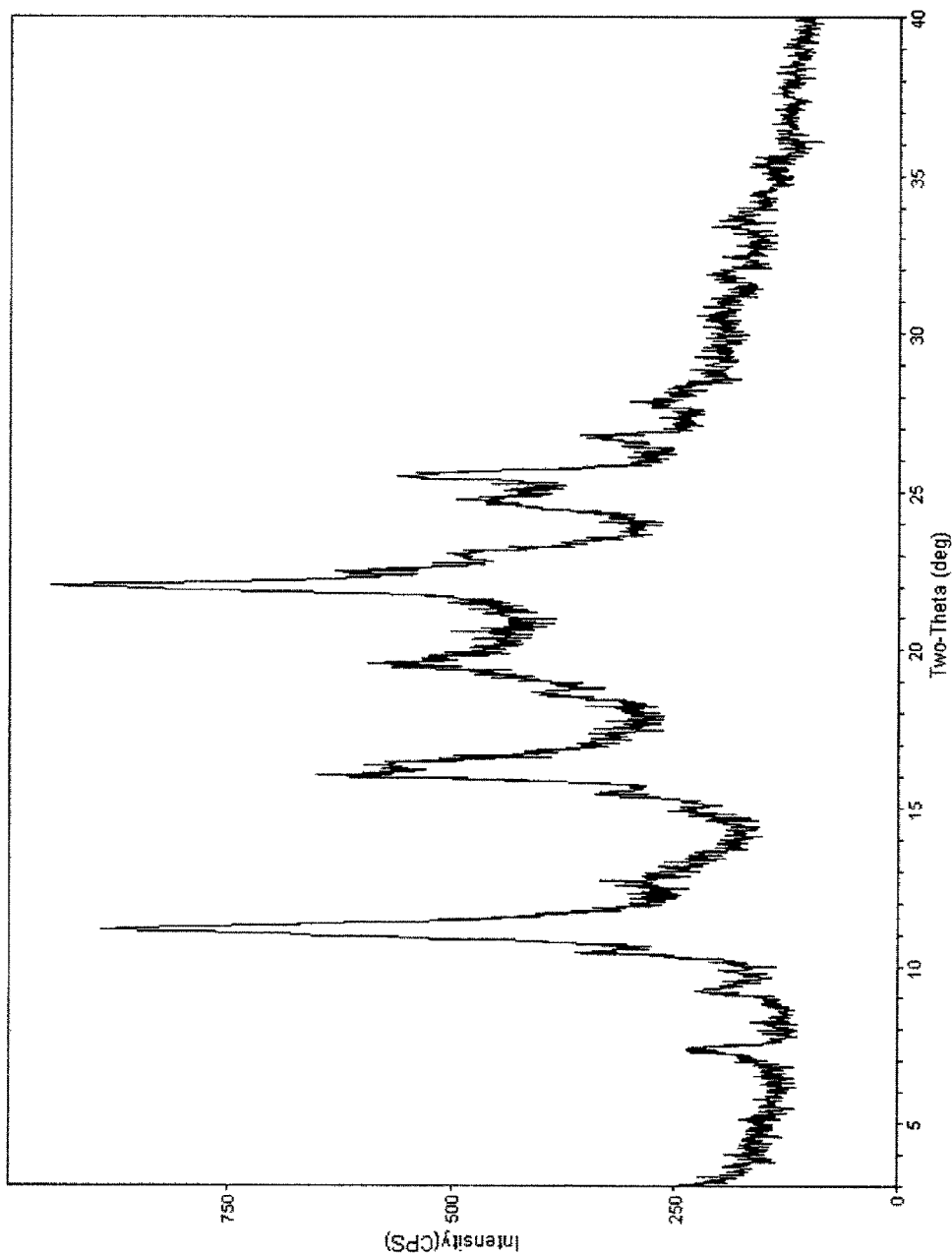
FIG. 21 shows a characteristic XRPD scan of Form H.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H which has an XRPD diffraction pattern substantially the same as FIG. 21 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H which is characterized by XRPD diffraction peaks (2θdegrees±0.2) substantially the same as Table 21 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H which is characterized by an endotherm at about 231.6° C. is provided.

Figure 50:
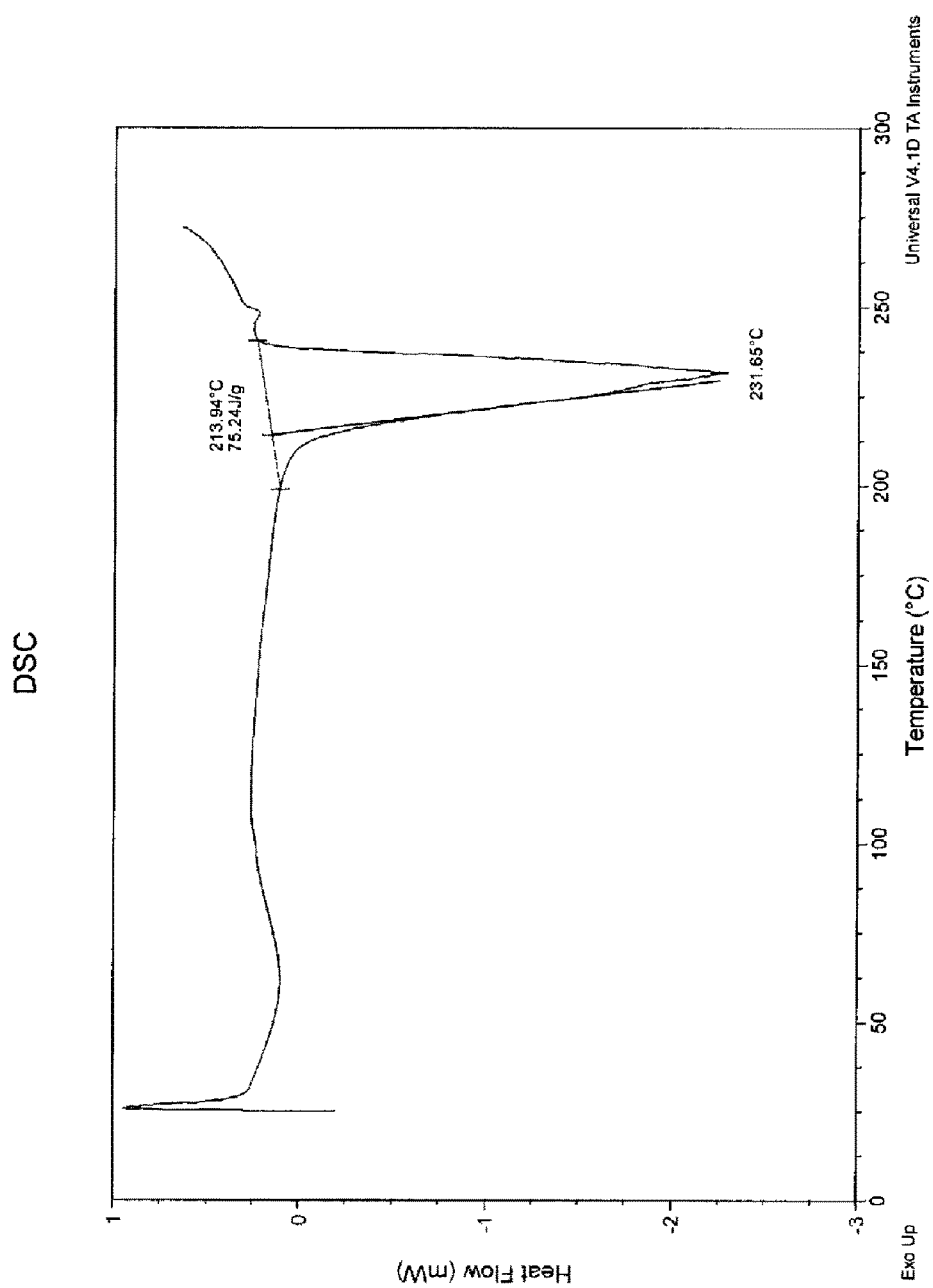
FIG. 50 shows a characteristic DSC scan of Form H.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H which is characterized by a DSC scan substantially the same as FIG. 50 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form H comprising:
(a) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and MTBE; and
(b) recrystallizing the solid to prepare Form H.

Form I

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I is provided. Form I can be distinguished by the XRPD diffraction in FIG. 22 and/or peak assignments of the XRPD diffraction of FIG. 22 in Table 22.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I, characterized by at least one specific XRPD diffraction peak at about (2θdegrees±0.2) 7.2 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I, characterized by XRPD diffraction peaks at about (2θdegrees±0.2) 7.2, 16.6, 18.3, 22.3 and 23.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I, characterized by XRPD diffraction peaks at about (2θdegrees±0.2) 7.2, 16.559, 18.303, 22.282 and 23.101 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I, characterized by XRPD diffraction peaks at about (2θdegrees±0.2) 7.2, 12.1, 16.3, 16.6, 18.3, 19.3, 19.5, 20.6, 22.3 and 23.1 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I, characterized by XRPD diffraction peaks at about (2θdegrees±0.2) 7.2, 12.117, 16.319, 16.559, 18.303, 19.32, 19.54, 20.641, 22.282 and 23.101 is provided.

Figure 22:
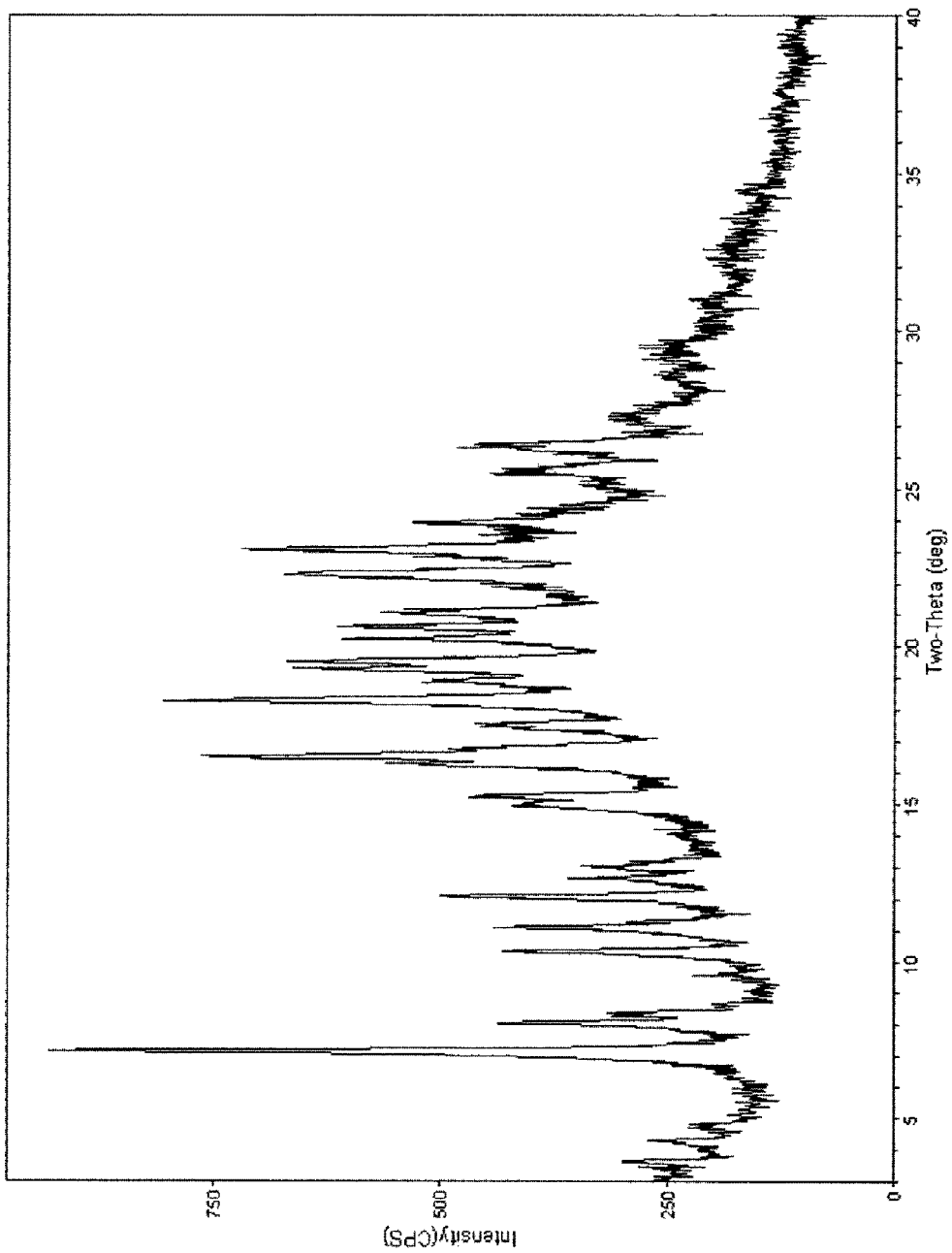
FIG. 22 shows a characteristic XRPD scan of Form I.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I which has an XRPD diffraction pattern substantially the same as FIG. 22 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I which is characterized by XRPD diffraction peaks (2θdegrees±0.2) substantially the same as Table 22 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I which is characterized by endotherms at about 132.6° C. and 236.3° C. and an exotherm at about 183.3° C. is provided.

Figure 51:
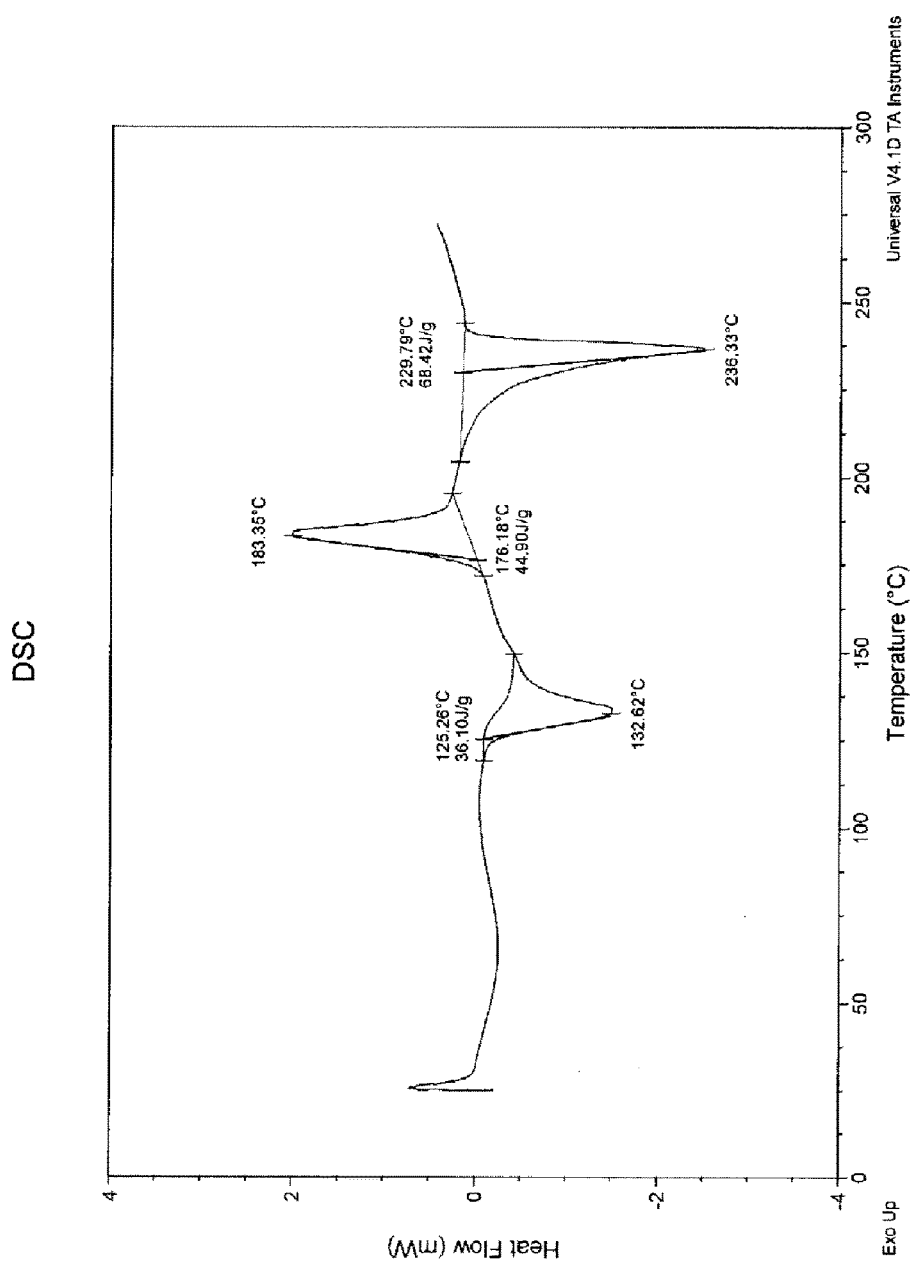
FIG. 51 shows a characteristic DSC scan of Form I.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I which is characterized by a DSC scan substantially the same as FIG. 51 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form I comprising:

(a) mixing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and xylene; and (b) recrystallizing the solid to prepare Form I.

Form J

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J is provided. Form J can be distinguished by the XRPD diffraction in FIG. 23 and/or peak assignments of the XRPD diffraction of FIG. 23 in Table 23.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J, characterized by at least one specific XRPD diffraction peak at about (2θdegrees±0.2) 17.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J, characterized by at least one specific XRPD diffraction peak at about (2θdegrees±0.2) 16.963 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J, characterized by XRPD diffraction peaks at about (2θdegrees±0.2) 4.5, 9.0, 17.0, 18.0 and 18.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J, characterized by XRPD diffraction peaks at about (2θdegrees±0.2) 4.479, 8.982, 16.963, 18.078 and 18.797 is provided.

Figure 23:
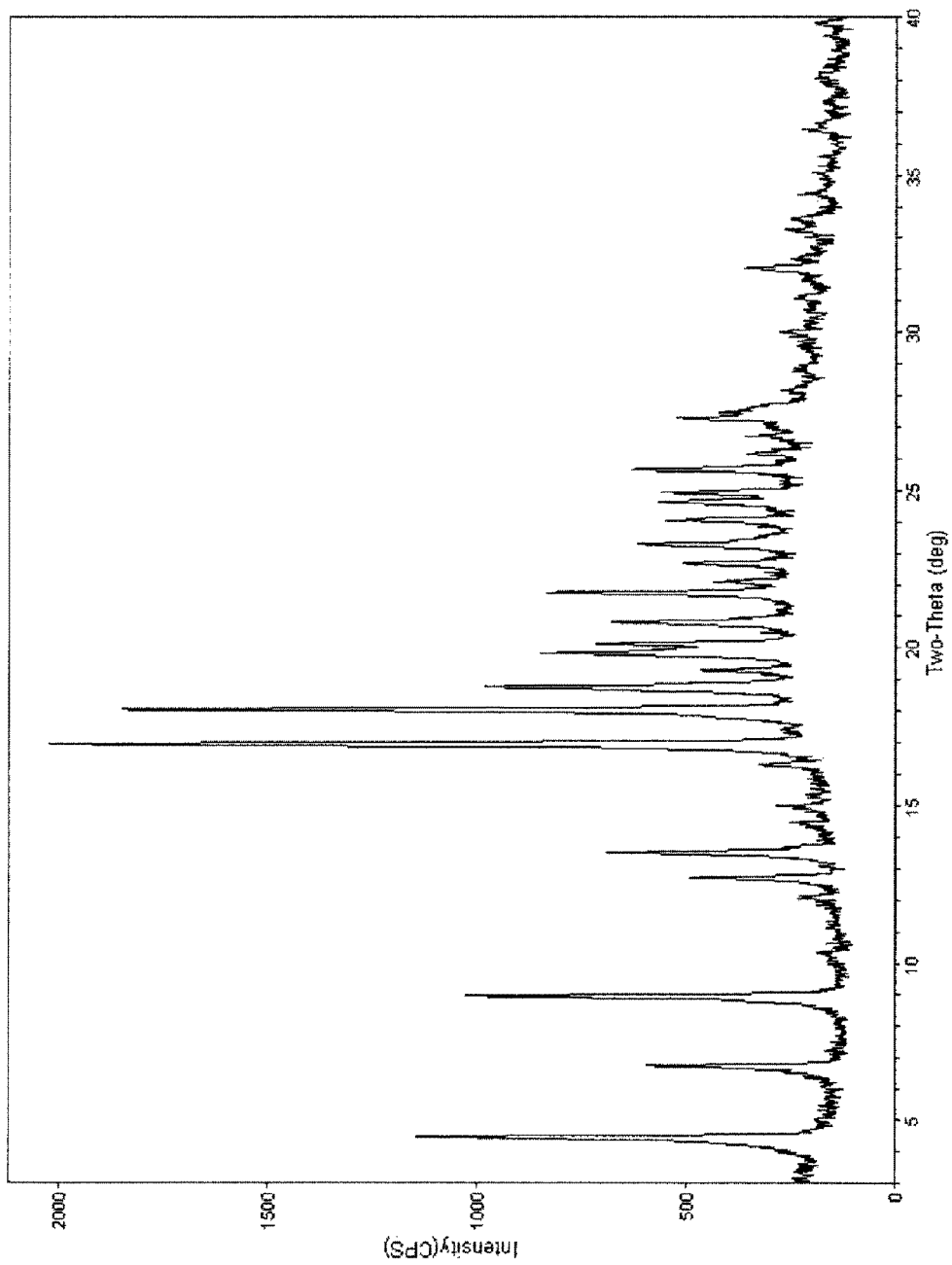
FIG. 23 shows a characteristic XRPD scan of Form J.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J which has an XRPD diffraction pattern substantially the same as FIG. 23 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J which is characterized by XRPD diffraction peaks (2θdegrees±0.2) substantially the same as Table 23 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form J comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and 2-methoxyethanol; and (b) recrystallizing the solid to prepare Form J.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

Form K

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6- diamine Form K is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K is provided. Form K can be distinguished by the XRPD diffraction in FIG. 24 and/or peak assignments of the XRPD diffraction of FIG. 24 in Table 24.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K, characterized by at least one specific XRPD diffraction peak at about (2θdegrees±0.2) 22.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K, characterized by at least one specific XRPD diffraction peak at about (2θdegrees±0.2) 22.78 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K, characterized by XRPD diffraction peaks at about (2θdegrees±0.2) 15.8, 17.6, 22.8, 23.0 and 25.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K, characterized by XRPD diffraction peaks at about (2θdegrees±0.2) 15.797, 17.62, 22.78, 23 and 25.701 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K, characterized by XRPD diffraction peaks at about (2θdegrees±0.2) 13.9, 15.8, 17.6, 19.0, 22.8, 23.0 and 25.7 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K, characterized by XRPD diffraction peaks at about (2θdegrees±0.2) 13.923, 15.797, 17.62, 18.999, 22.78, 23 and 25.701 is provided.

Figure 24:
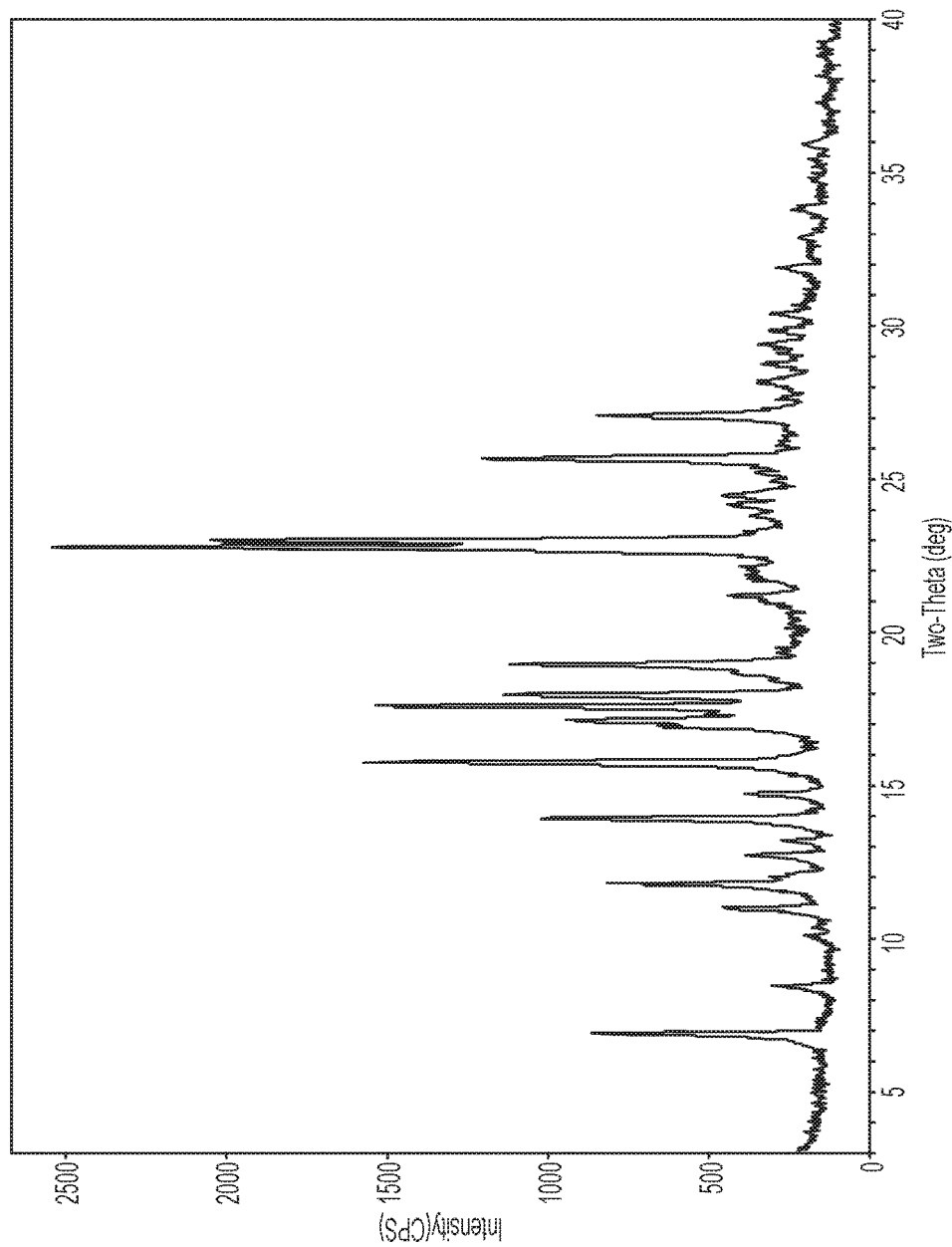
FIG. 24 shows a characteristic XRPD scan of Form K.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K which has an XRPD diffraction pattern substantially the same as FIG. 24 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K which is characterized by XRPD diffraction peaks (2θdegrees±0.2) substantially the same as Table 24 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K which is characterized by endotherms at about 119.3° C., 241.2° C. and 253.4° C. and an exotherm at about 171.6° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K which is characterized by endotherms at about 241.2° C. and 253.4° C. and an exotherm at about 171.6° C. is provided.

Figure 52:
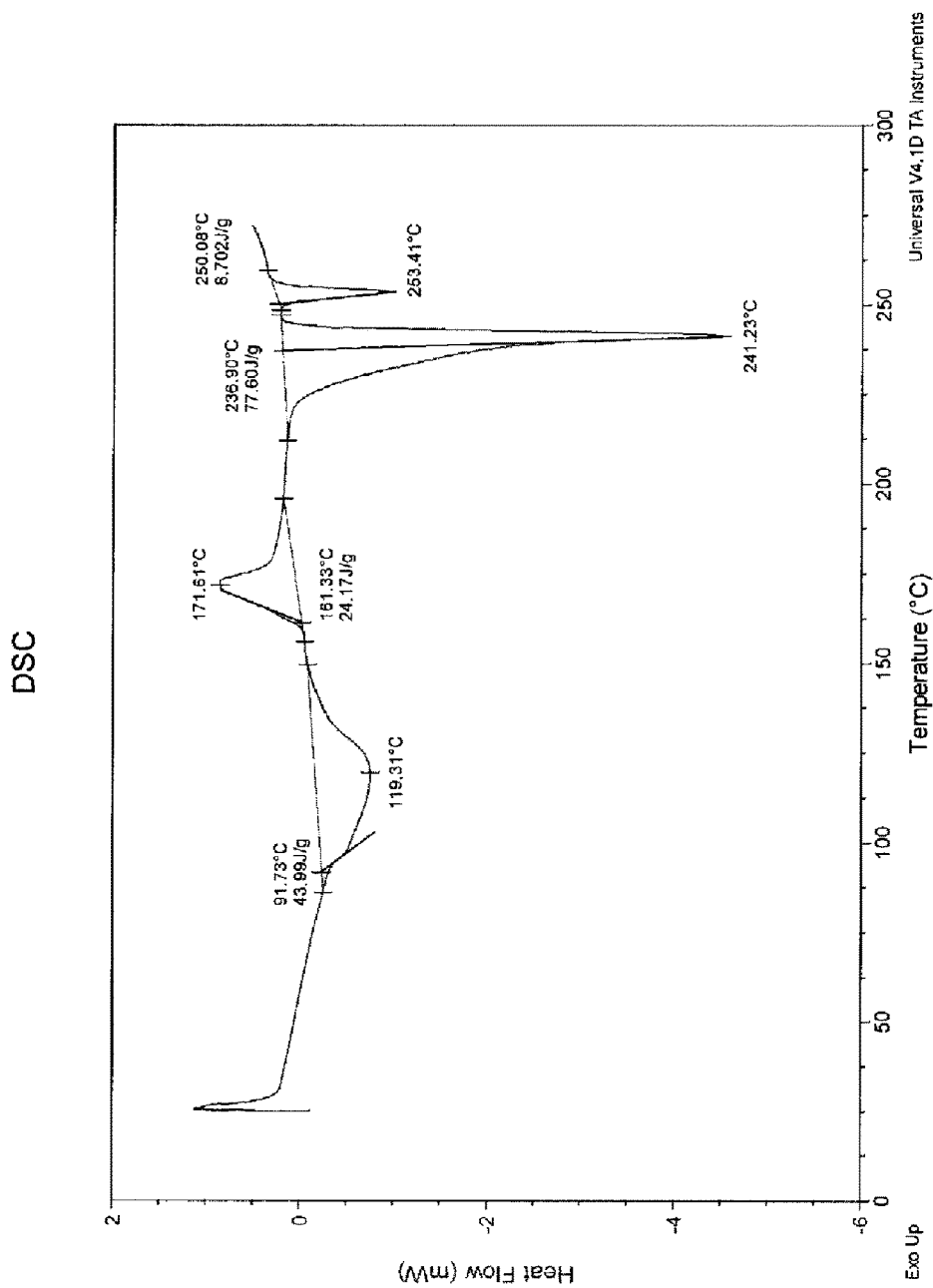
FIG. 52 shows a characteristic DSC scan of Form K.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K which is characterized by a DSC scan substantially the same as FIG. 52 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form K comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and DME; and (b) recrystallizing the solid to prepare Form K.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

Form L

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L is provided. Form L can be distinguished by the XRPD diffraction in FIG. 25 and/or peak assignments of the XRPD diffraction of FIG. 25 in Table 25.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L, characterized by at least one specific XRPD diffraction peak at about (2θdegrees±0.2) 17.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L, characterized by at least one specific XRPD diffraction peak at about (2θdegrees±0.2) 16.98 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L, characterized by XRPD diffraction peaks at about (2θdegrees±0.2) 14.9, 17.0, 19.0, 21.1 and 22.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L, characterized by XRPD diffraction peaks at about (2θdegrees±0.2) 14.899, 16.98, 18.958, 21.062 and 22.457 is provided.

Figure 25:
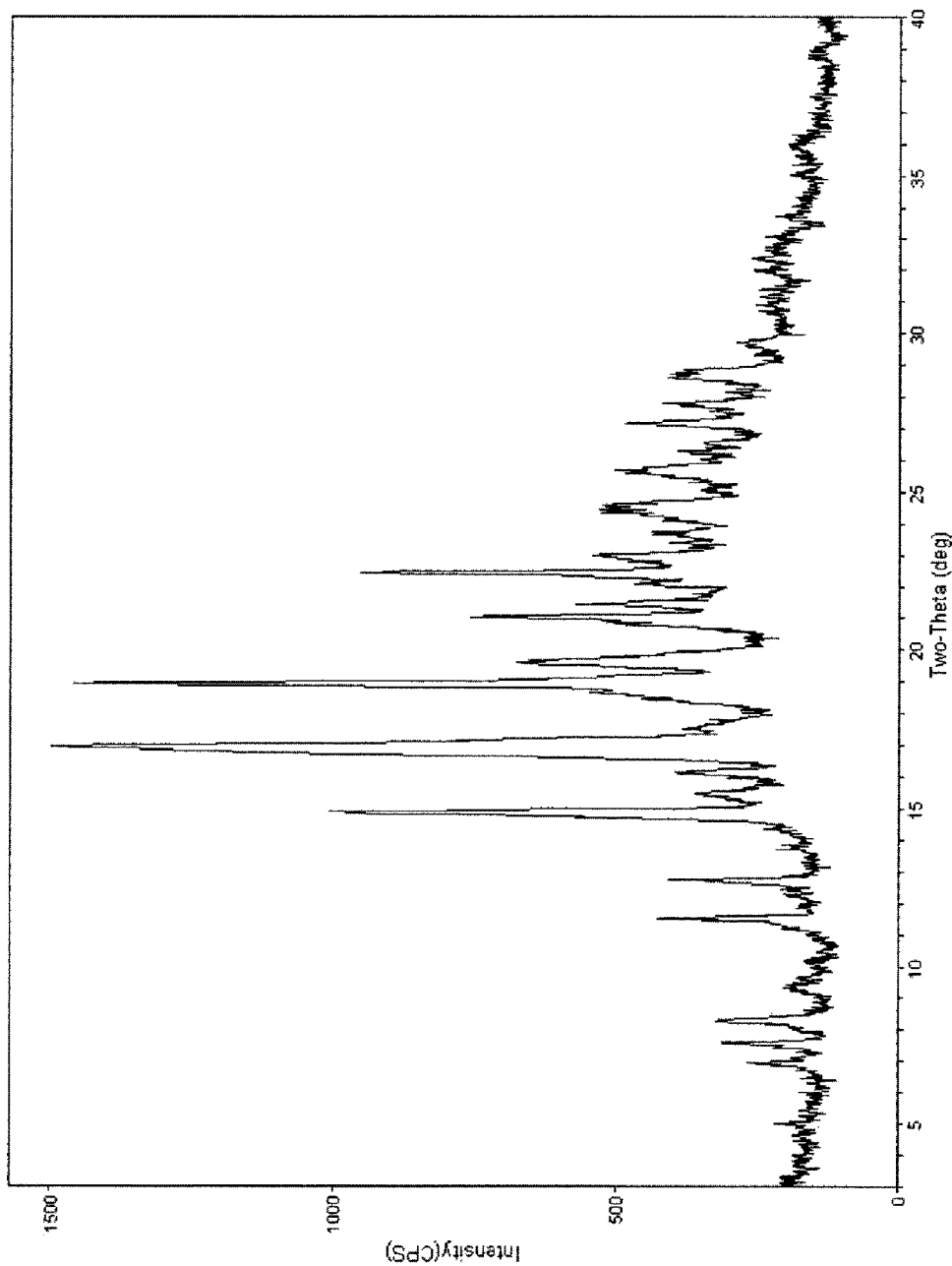
FIG. 25 shows a characteristic XRPD scan of Form L.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L which has an XRPD diffraction pattern substantially the same as FIG. 25 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L which is characterized by XRPD diffraction peaks (2θdegrees±0.2) substantially the same as Table 25 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L which is characterized by endotherms at about 120.4° C. and 251.6° C. and an exotherm at about 202.3° C. is provided.

In certain embodiments, a crystalline polymorph N4-(4-([1,2,4]triazolo[1,5-a]pyridin-7-yloxy)-3-methylphenyl)-

Figure 53:
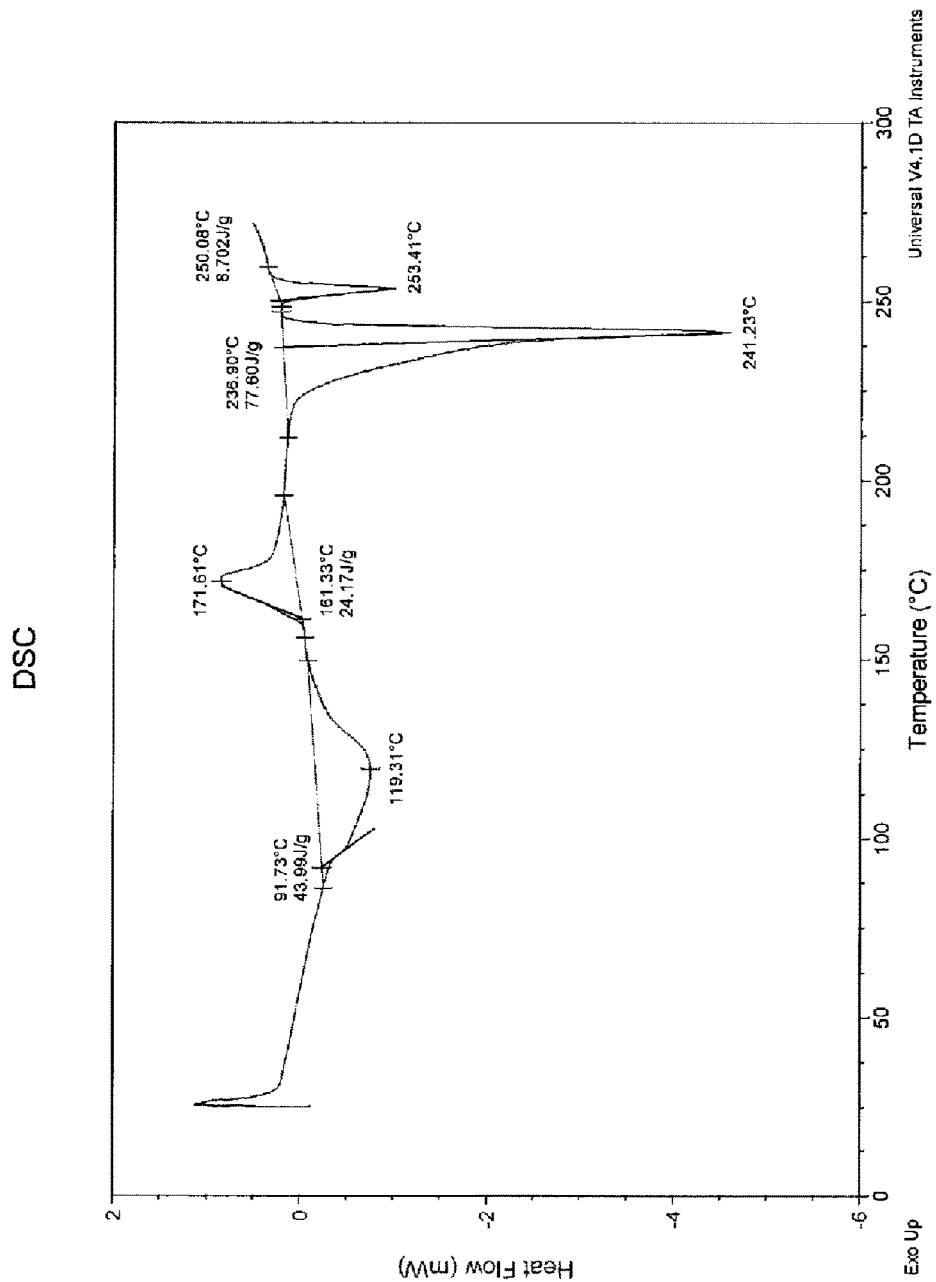
FIG. 53 shows a characteristic DSC scan of Form L.

N6-(4,4-dimethyl-4,5-dihydrooxazol-2-yl)quinazoline-4,6-diamine Form L which is characterized by a DSC scan substantially the same as FIG. 53 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form L comprising:

(a) mixing either N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E or amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and MeOAc; and (b) recrystallizing the solid to prepare Form L.

In certain embodiments, N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form E is used in Step (a).

Form M

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M is provided. Form M can be distinguished by the XRPD diffraction in FIG. 26 and/or peak assignments of the XRPD diffraction of FIG. 26 in Table 26.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M, characterized by at least one specific XRPD diffraction peak at about (2θdegrees±0.2) 9.0 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M, characterized by at least one specific XRPD diffraction peak at about (2θdegrees±0.2) 8.982 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M, characterized by XRPD diffraction peaks at about (2θdegrees±0.2) 9.0, 15.1, 20.7, 23.1 and 26.8 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M, characterized by XRPD diffraction peaks at about (2θdegrees±0.2) 8.982, 15.136, 20.738, 23.083 and 26.76 is provided.

Figure 26:
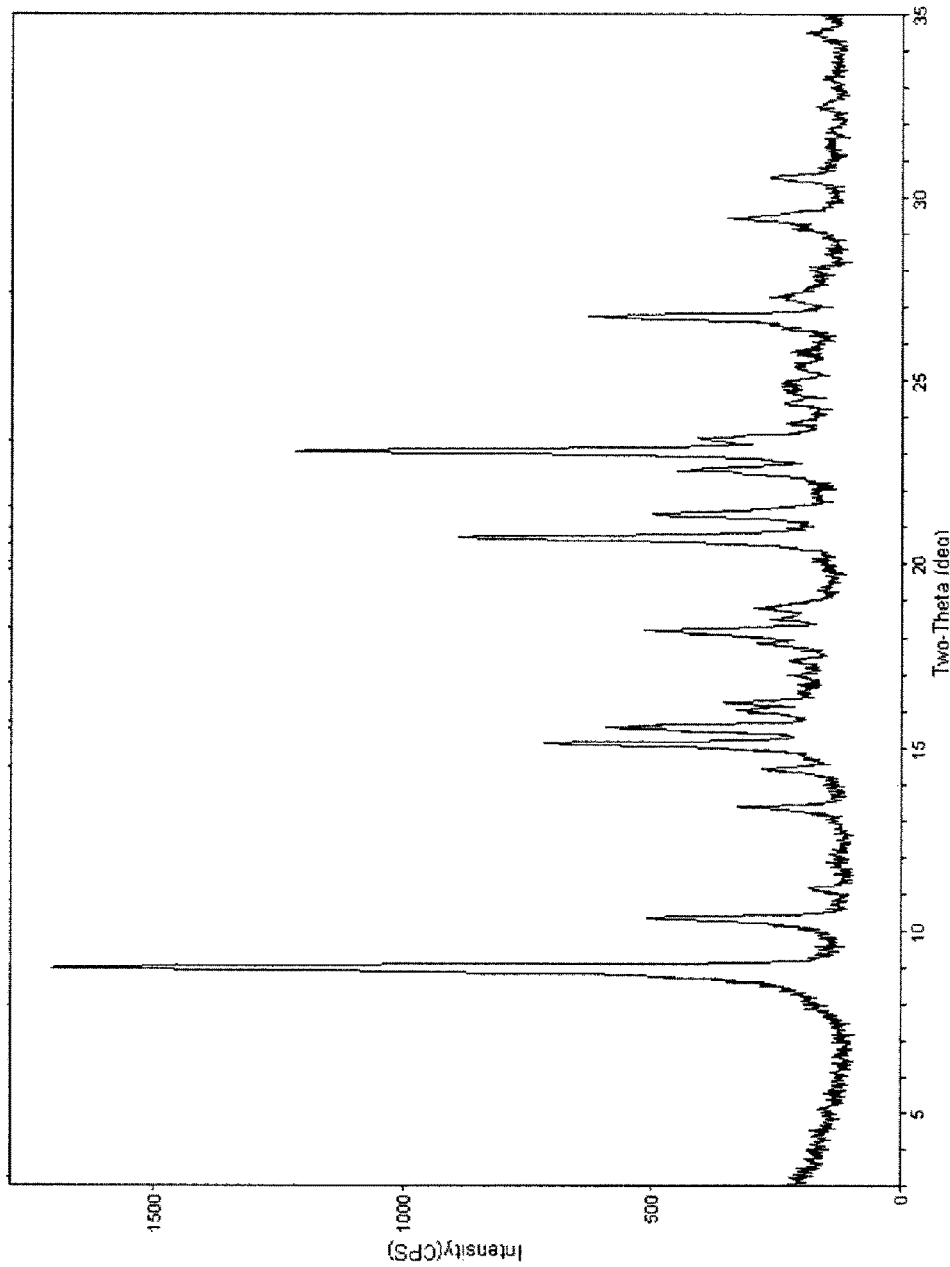
FIG. 26 shows a characteristic XRPD scan of Form M.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M which has an XRPD diffraction pattern substantially the same as FIG. 26 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M which is characterized by XRPD diffraction peaks (2θdegrees±0.2) substantially the same as Table 26 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M which is characterized by endotherms at about 124.2° C., 229.0° C., 246.0° C. and 256.0° C. and an exotherm at about 198.4° C. is provided. In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M which is characterized by endotherms at about 124.2° C. and 246.0° C. and an exotherm at about 198.4° C. is provided.

Figure 54:
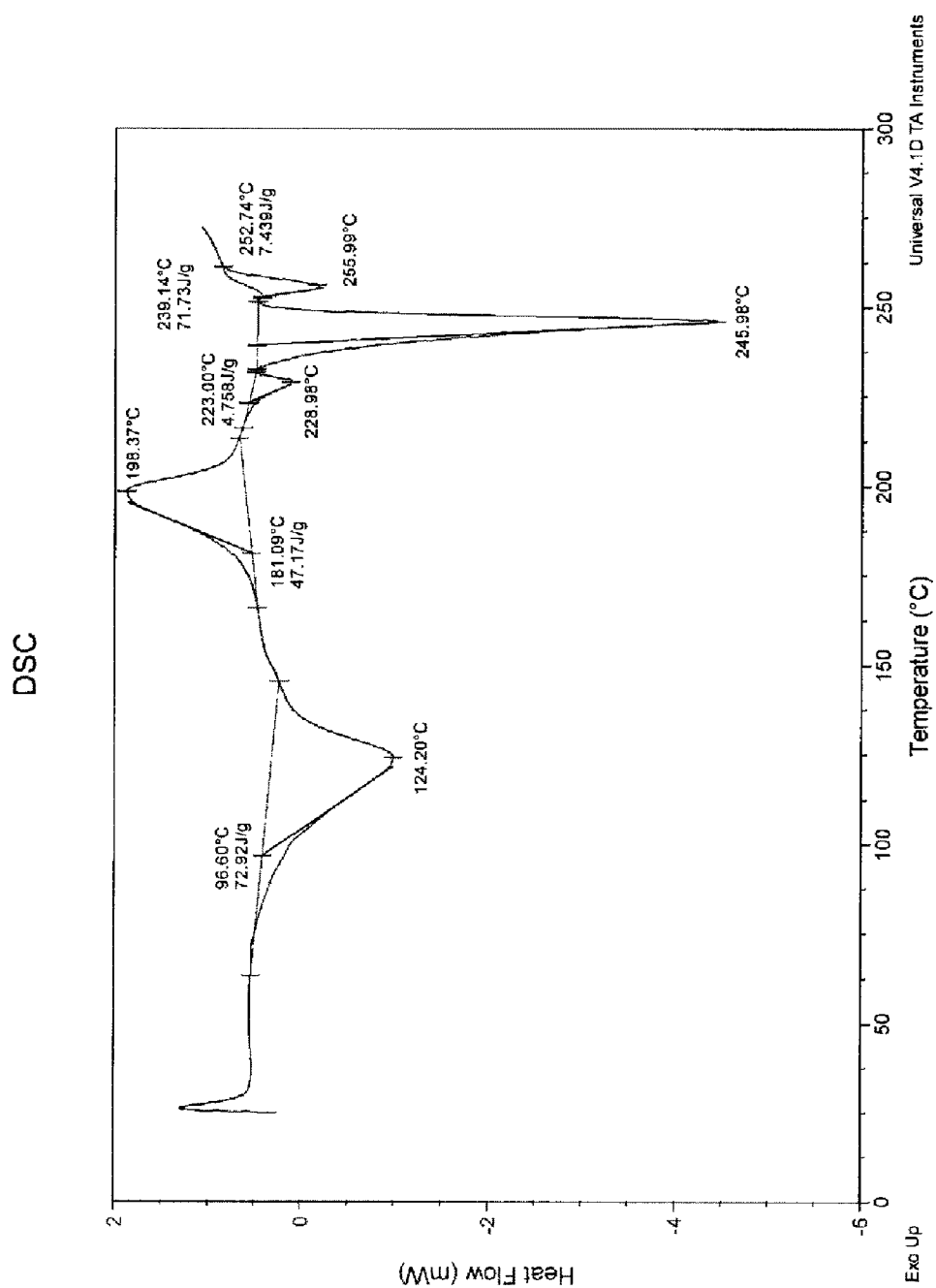
FIG. 54 shows a characteristic DSC scan of Form M.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M which is characterized by a DSC scan substantially the same as FIG. 54 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form M comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B Ethanol and 1:1 THF:water; and (b) recrystallizing the solid to prepare Form M.

Form N

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N is provided. Form N can be distinguished by the XRPD diffraction in FIG. 27 and/or peak assignments of the XRPD diffraction of FIG. 27 in Table 27.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N, characterized by at least one specific XRPD diffraction peak at about (2θdegrees±0.2) 22.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N, characterized by at least one specific XRPD diffraction peak at about (2θdegrees±0.2) 22.92 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N, characterized by XRPD diffraction peaks at about (2θdegrees±0.2) 15.9, 17.8, 19.2, 22.9 and 25.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N, characterized by XRPD diffraction peaks at about (2θdegrees±0.2) 15.88, 17.759, 19.202, 22.92 and 25.881 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N, characterized by XRPD diffraction peaks at about (2θdegrees±0.2) 14.0, 15.9, 17.8, 18.1, 19.2, 22.9 and 25.9 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N, characterized by XRPD diffraction peaks at about (2θdegrees±0.2) 14.02, 15.88, 17.759, 18.08, 19.202, 22.92 and 25.881 is provided.

Figure 27:
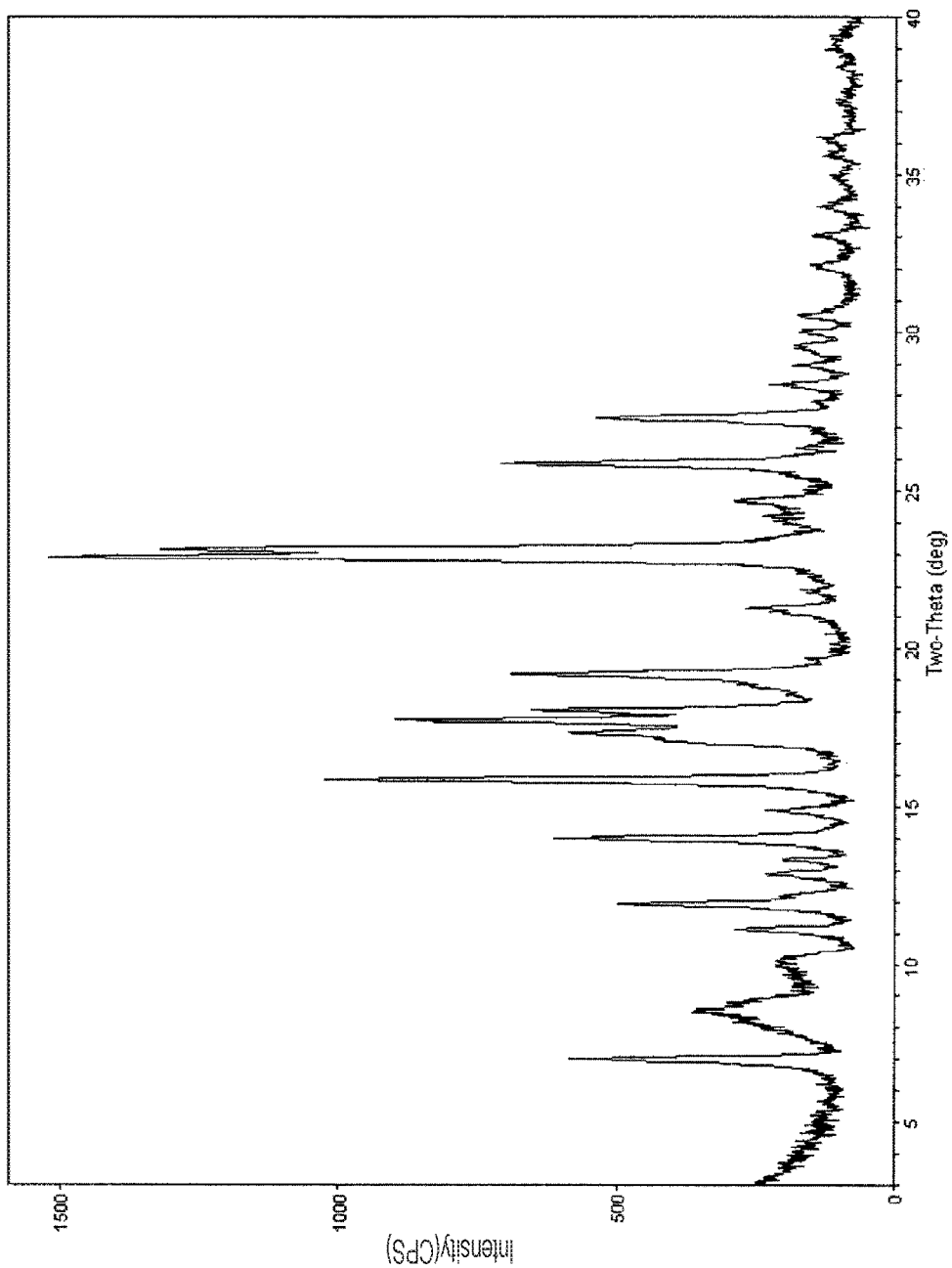
FIG. 27 shows a characteristic XRPD scan of Form N.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6- diamine Form N which has an XRPD diffraction pattern substantially the same as FIG. 27 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N which is characterized by XRPD diffraction peaks (2θdegrees±0.2) substantially the same as Table 27 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N which is characterized by endotherms at about 111.0° C. and 242.4° C. and an exotherm at about 146.1° C. is provided.

Figure 55:
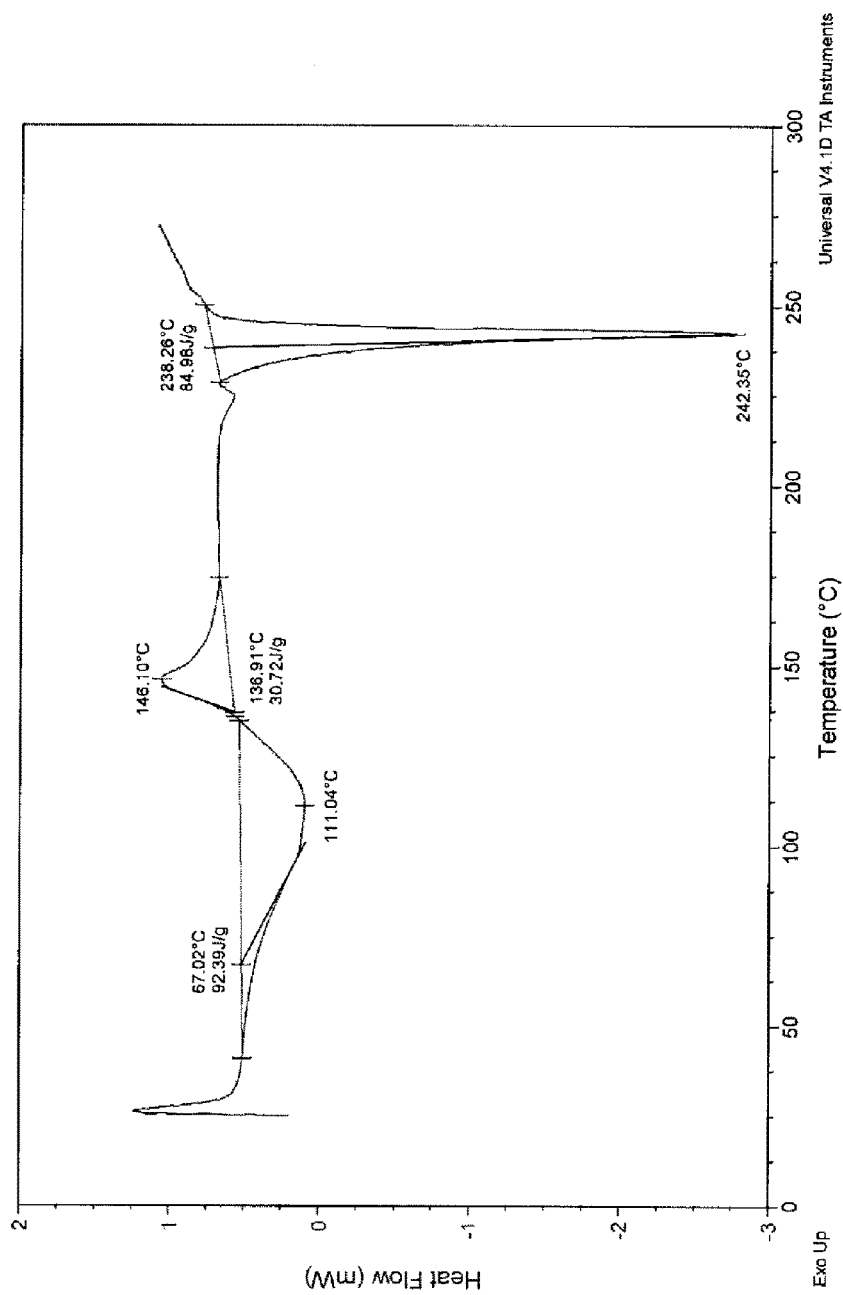
FIG. 55 shows a characteristic DSC scan of Form N.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N which is characterized by a DSC scan substantially the same as FIG. 55 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form N comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B Ethanol and a solution of 1% sodium carboxymethyl cellulose, 0.1% Tween® in water; and (b) recrystallizing the solid to prepare Form N.

Form O

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O is provided. Form O can be distinguished by the XRPD diffraction in FIG. 28 and/or peak assignments of the XRPD diffraction of FIG. 28 in Table 28.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form 0, characterized by at least one specific XRPD diffraction peak at about (2θdegrees±0.2) 11.2 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form 0, characterized by at least one specific XRPD diffraction peak at about (2θdegrees±0.2) 11.238 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form 0, characterized by XRPD diffraction peaks at about (2θdegrees±0.2) 11.2, 16.5, 20.0, 22.2 and 25.6 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form 0, characterized by XRPD diffraction peaks at about (2θdegrees±0.2) 11.238, 16.52, 19.98, 22.179 and 25.638 is provided.

Figure 28:
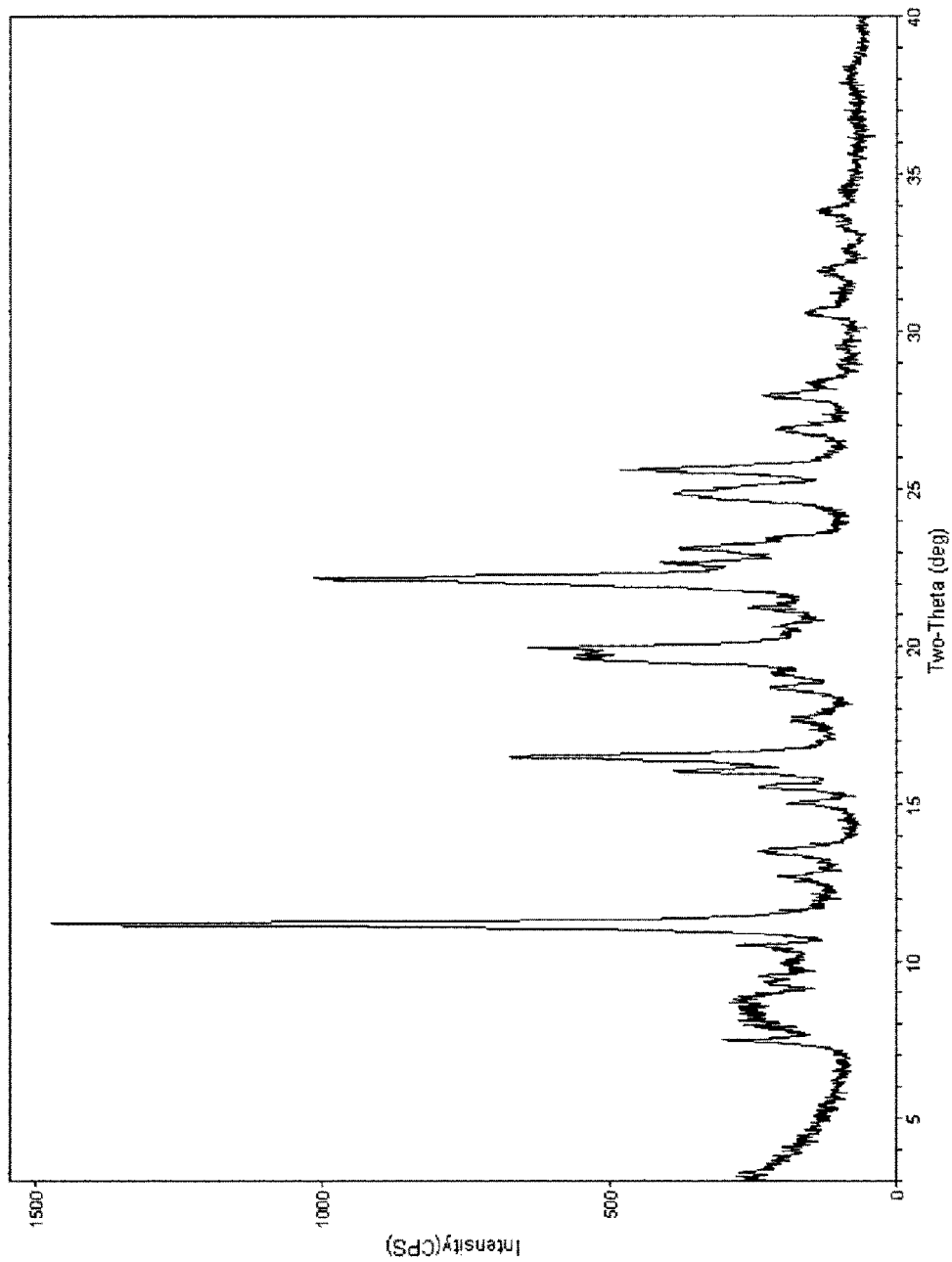
FIG. 28 shows a characteristic XRPD scan of Form O.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O which has an XRPD diffraction pattern substantially the same as FIG. 28 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O which is characterized by XRPD diffraction peaks (2θdegrees±0.2) substantially the same as Table 28 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O which is characterized by an endotherm at about 245.4° C. is provided.

Figure 56:
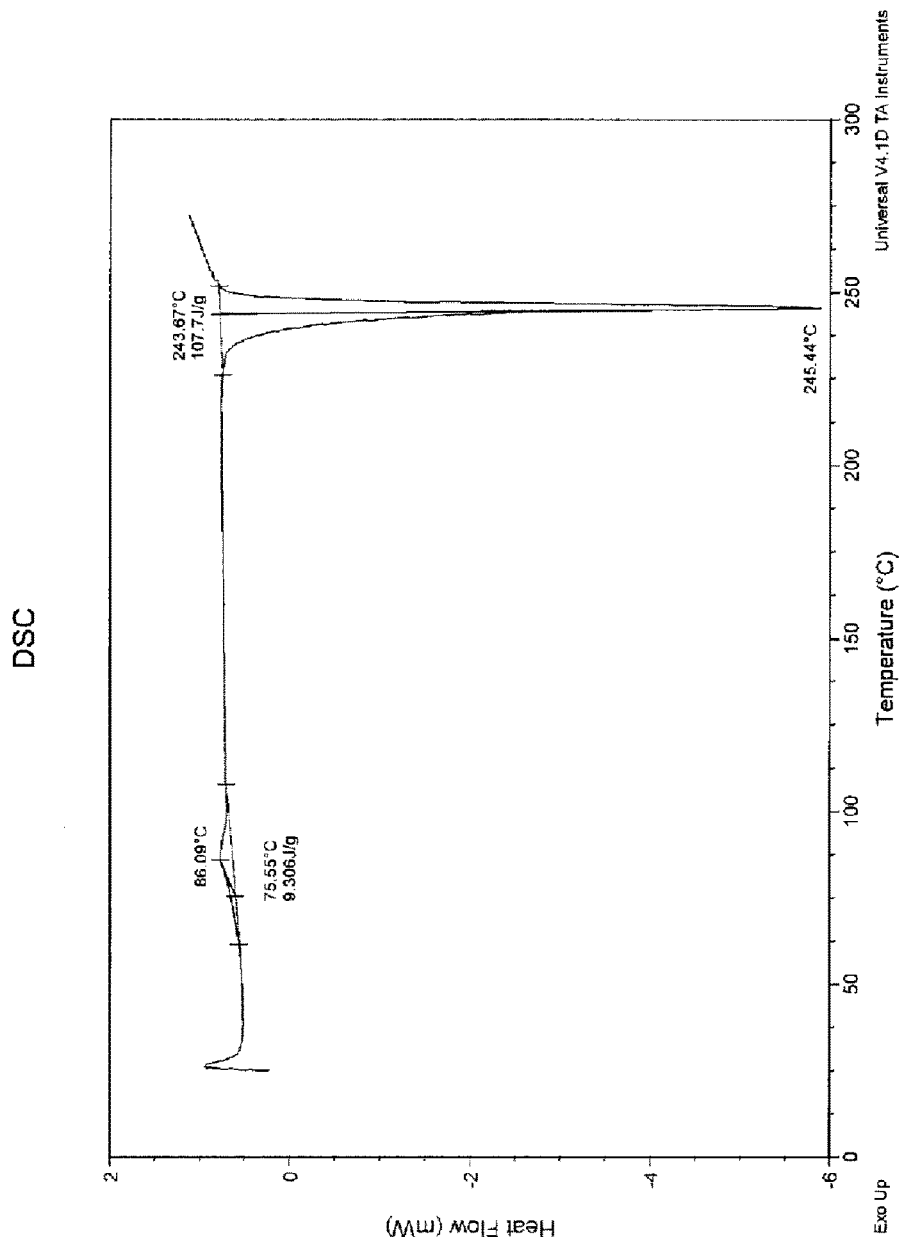
FIG. 56 shows a characteristic DSC scan of Form O.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O which is characterized by a DSC scan substantially the same as FIG. 56 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form O comprising:

(a) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran with THF;

(b) creating a solution with the N4-(4-([1,2,4]triazolo[1,5-a]pyridin-7-yl oxy)-3-methylphenyl)-N6-(4,4-dimethyl-4,5-dihydrooxazol-2-yl)quinazoline-4,6-diamine and THF; and (c) recrystallizing the solid to prepare Form 0.

In certain embodiments, the solution in Step (b) is created by heating the mixture of Step (a) to about 50° C.

Form P

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P is provided. In certain embodiments, a substantially pure crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P is provided. Form P can be distinguished by the XRPD diffraction in FIG. 29 and/or peak assignments of the XRPD diffraction of FIG. 29 in Table 29.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P, characterized by at least one specific XRPD diffraction peak at about (2θdegrees±0.2) 23.5 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P, characterized by XRPD diffraction peaks at about (2θdegrees±0.2) 9.9, 13.7, 15.7, 17.7 and 23.5 is provided. In a further embodiment, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P, characterized by XRPD diffraction peaks at about (2θdegrees±0.2) 9.901, 13.74, 15.662, 17.661 and 23.5 is provided.

Figure 29:
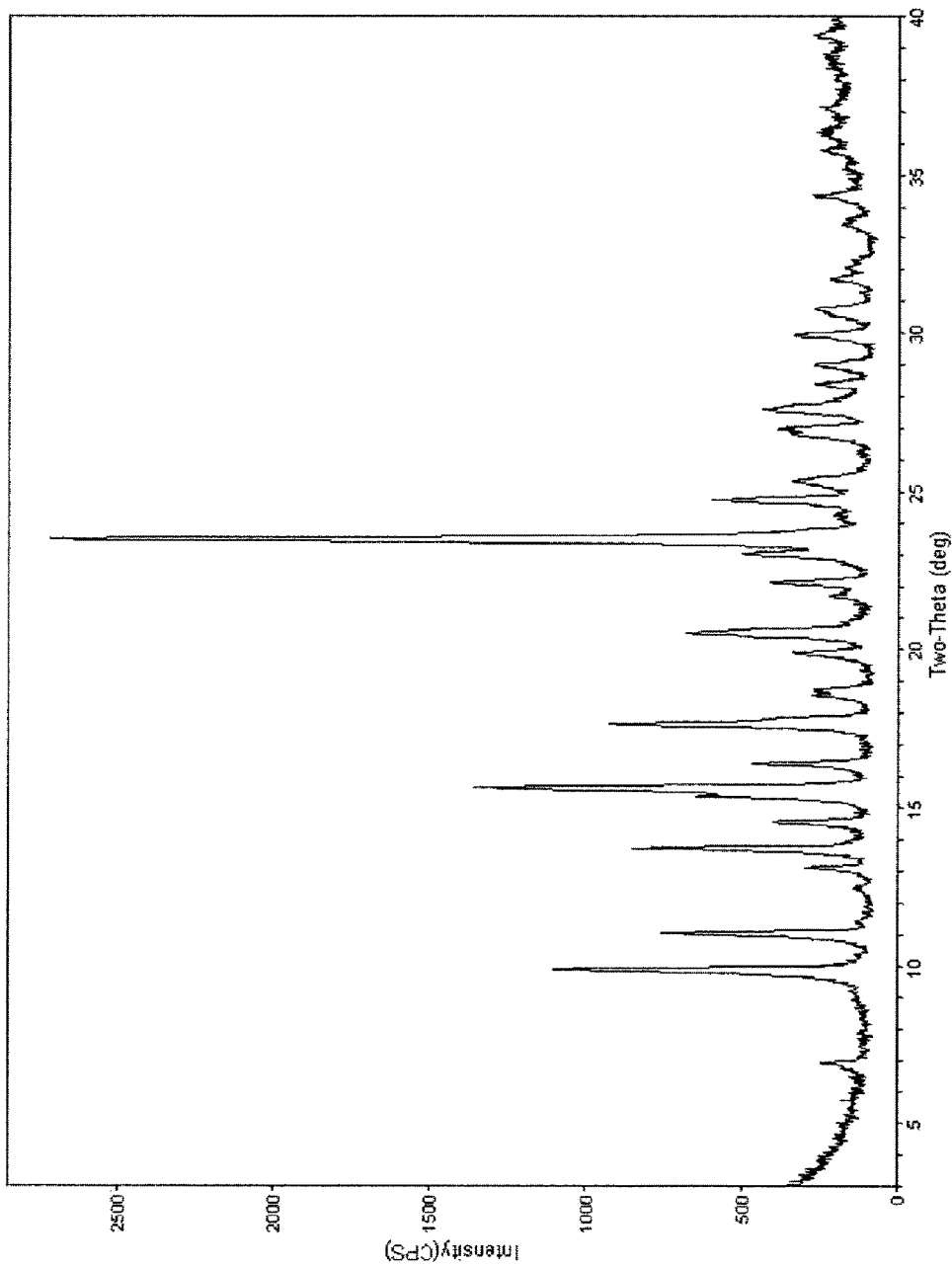
FIG. 29 shows a characteristic XRPD scan of Form P.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P which has an XRPD diffraction pattern substantially the same as FIG. 29 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6- diamine Form P which is characterized by XRPD diffraction peaks (2θdegrees±0.2) substantially the same as Table 29 is provided.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P which is characterized by endotherms at about 159.2° C., 246.7° C. and 262.2° C. is provided.

Figure 57:
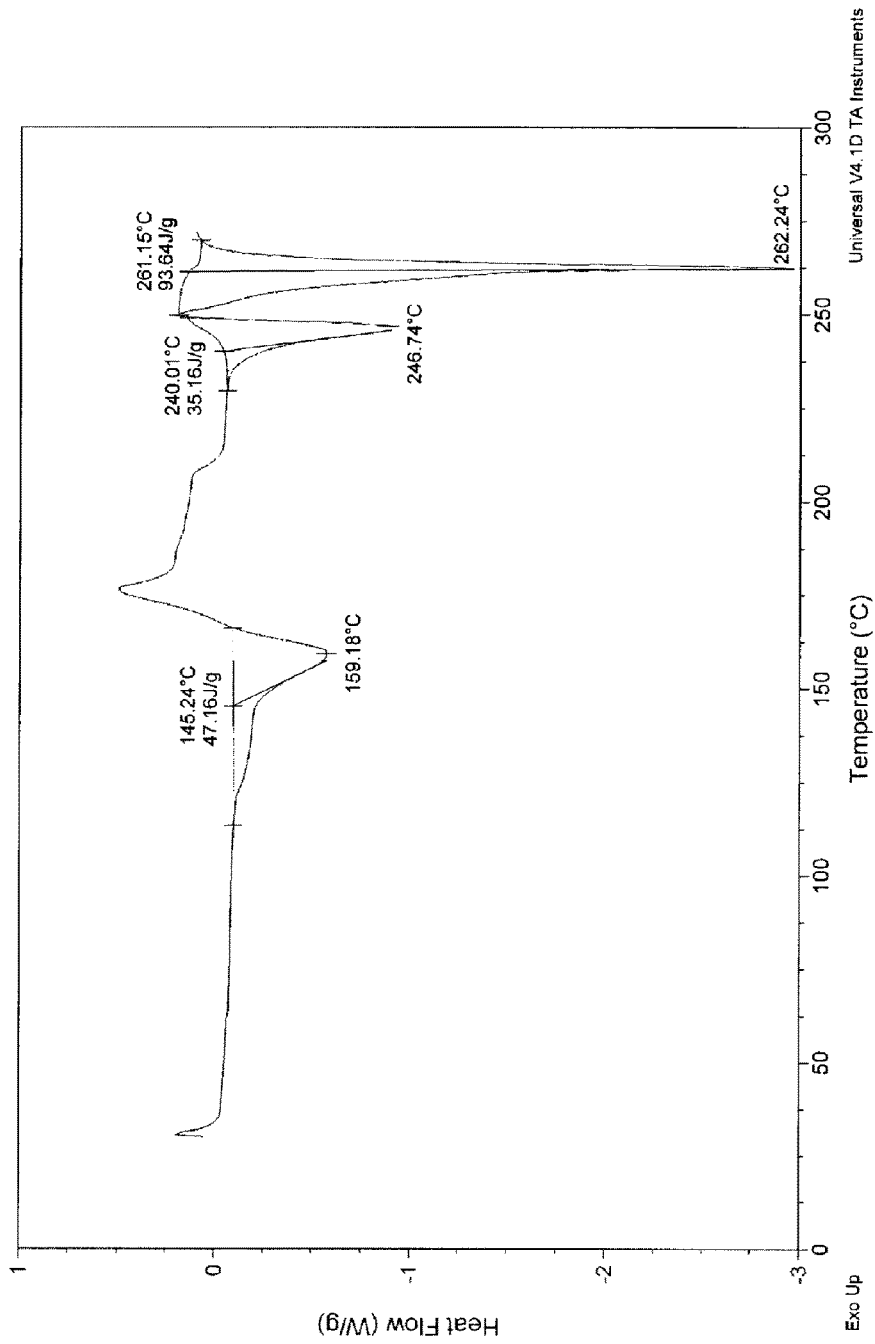
FIG. 57 shows a characteristic DSC scan of Form P.

In certain embodiments, a crystalline polymorph N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P which is characterized by a DSC scan substantially the same as FIG. 57 is provided.

Certain embodiments provide a process for preparing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form P comprising:

(a) mixing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Tetrahydrofuran with water; and (b) recrystallizing the solid to prepare Form P.

Amorphous

In certain embodiments, amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is provided. In certain embodiments, substantially pure amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is provided. Amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine is identified in the XRPD of FIG. 30.

Figure 30:
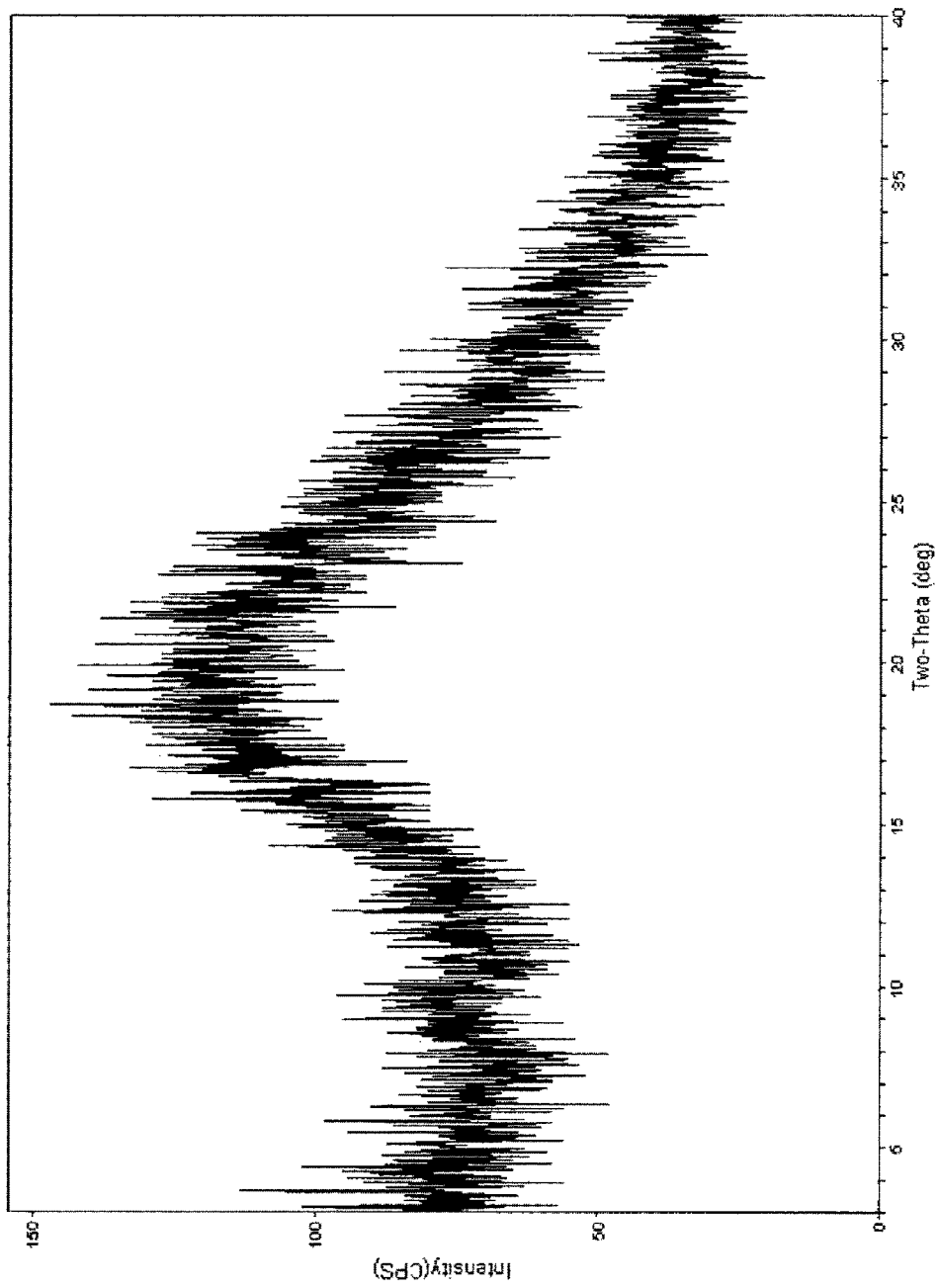
FIG. 30 shows a characteristic XRPD scan of amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine.

In certain embodiments, amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine which has an XRPD diffraction pattern substantially the same as FIG. 30 is provided.

Figure 58:
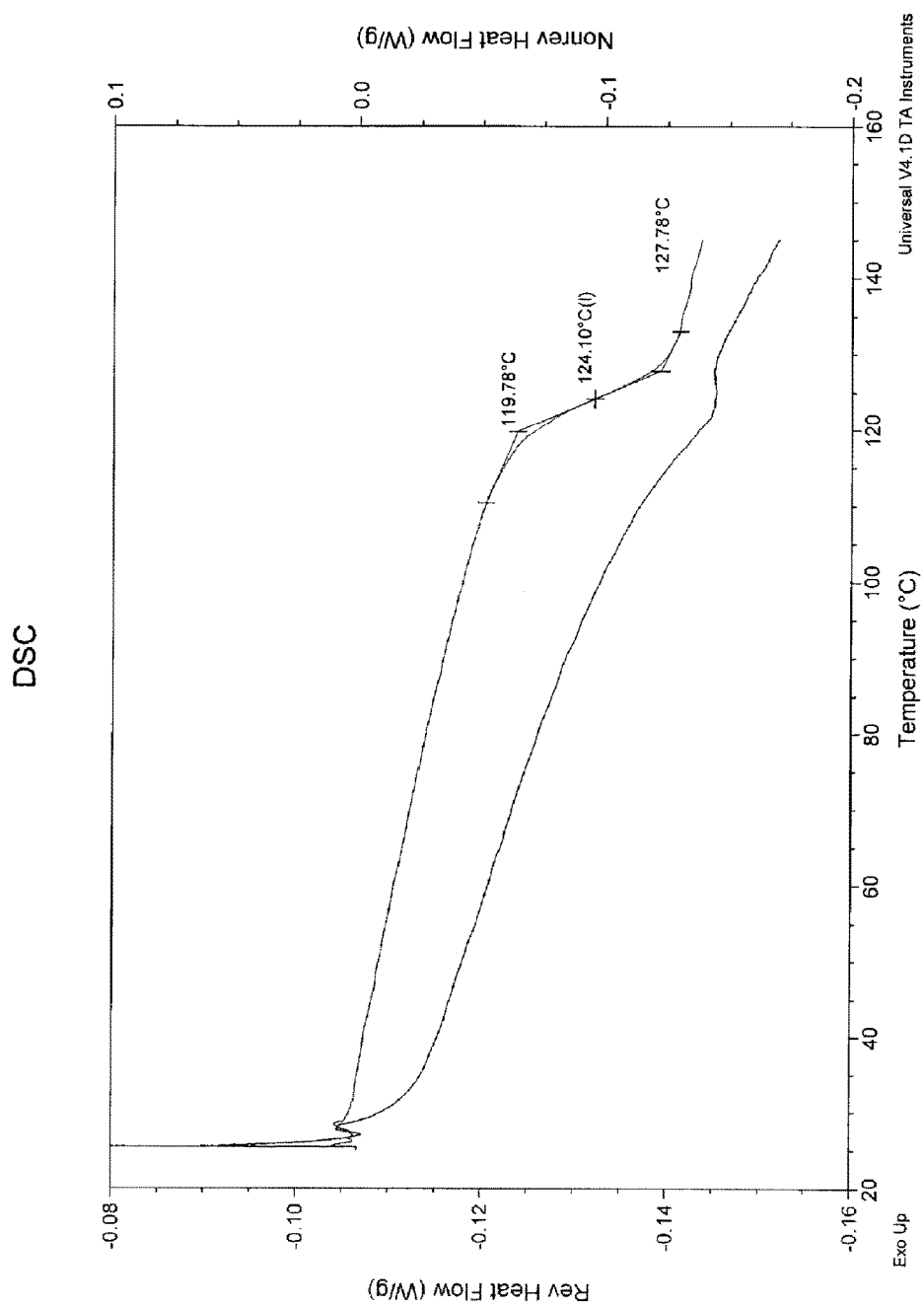
FIG. 58 shows a characteristic mDSC scan of amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine.

In certain embodiments, amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine which is characterized by an mDSC scan substantially the same as FIG. 58 is provided.

Certain embodiments provide a process for preparing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine comprising:

(a) mixing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B Ethanol with 3:7 water:THF;

(b) sonicating the solution of Step (a);

(c) freezing and lyophilizing the solution to prepare amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine.

The invention also includes isotopically-labeled N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine, which is identical, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen and oxygen, such as $^2H$, $^3H$, $^{13}C$, $^{14}C$, $^{15}N$, $^{18}O$ and $^{17}O$, respectively. The polymorphs described herein, which contain the aforementioned isotopes and/or other isotopes of other atoms are within the scope of this invention. Certain isotopically-labeled compounds of the present invention, for example those into which radioactive isotopes, such as $^3H$ and $^{14}C$ are incorporated, are useful in drug and/or substrate tissue distribution assays. Tritiated, i.e., $^3H$ and carbon-14, i.e., $^{14}C$, isotopes are particularly widely used as a result of their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be utilized in some particular circumstances. Isotopically labeled salts of the present invention can generally be prepared by carrying out procedures disclosed in WO 03/077914 by substituting a readily available isotopically labeled reagent for a non-isotopically labeled reagent during the preparation, or if desired, using an isotopically labeled sulfuric acid in the preparation of the salt.

Synthesis of Compounds

Compounds described herein may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

The synthesis of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is described in WO 2007/059257. Generally, N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine may be prepared by coupling (E)-N'-(2-cyano-4-(3-(1-hydroxy-2-methylpropan-2-yl)thioureido)phenyl)-N,N-dimethylformimidamide with 4-([1,2,4]triazolo[1,5-a]pyridin-7-yloxy)-3-methylaniline in isopropyl acetate:acetic acid (65:35 v/v) at 45° C. to yield 1-(4-((4-([1,2,4]triazolo[1,5-a]pyridin-7-yloxy)-3-methylphenyl)amino)quinazolin-6-yl)-3-(1-hydroxy-2-methylpropan-2-yl)thiourea. The 1-(4-((4-([1,2,4]triazolo[1,5-a]pyridin-7-yloxy)-3-methylphenyl)amino)quinazolin-6-yl)-3-(1-hydroxy-2-methylpropan-2-yl)thiourea may then be agitated in tetrahydrofuran under basic conditions (2.5N NaOH), followed by the addition of p-toluenesulfonyl chloride. Water may then be charged to yield N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine as a mixture of polymorphs (generally a mixture containing one or more of Form C, Form G hemi-THF, Form G mono-THF, Form M or Form P). The final crystallizations or isolations will determine the polymorphic form, which are further detailed in the Examples section.

For a more detailed description of the individual reaction steps, see the Examples section below. Those skilled in the art will appreciate that other synthetic routes may be used to synthesize the compounds.

Administration and Pharmaceutical Formulations

The compounds described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), ocular, vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

One embodiment includes a pharmaceutical composition comprising a polymorph or amorphous compound described herein. A further embodiment provides a pharmaceutical composition comprising a polymorph or amorphous compound described herein, together with a pharmaceutically acceptable carrier or excipient.

The amount of the active compound administered will be dependent on the subject being treated, the severity of the disorder or condition, the rate of administration, the disposition of the compound and the discretion of the prescribing physician. However, an effective dosage is in the range of about 0.01 to about 100 mg per kg body weight per day, preferably about 1 to about 35 mg/kg/day, in single or divided doses. For a 70 kg human, this would amount to about 0.7 to 7000 mg/day, preferably about 70 to about 2500 mg/day. In some instances, dosage levels below the lower limit of the aforesaid range may be more than adequate, while in other cases still larger doses may be employed without causing any harmful side effect, provided that such larger doses are first divided into several small doses for administration throughout the day. A unit dosage form such as a tablet or capsule will usually contain, for example 1-1000 mg of active ingredient, and preferably 5-420 mg of active ingredient. Preferably a daily dose in the range of 0.03-6 mg/kg is employed.

Methods of Treatment with Compounds of the Invention

Also provided are methods of treating or preventing disease or condition by administering the pharmaceutical compositions described herein. In one embodiment, a human patient is treated with a pharmaceutical composition described herein in an amount to detectably inhibit ErbB2 activity.

In another embodiment, a method of treating a hyperproliferative disease in a mammal comprising administering a pharmaceutical composition described herein, to the mammal is provided.

In another embodiment, a method of treating or preventing cancer in a mammal in need of such treatment, wherein the method comprises administering to said mammal a pharmaceutical composition described herein. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. Another embodiment provides the use of a pharmaceutical composition described herein, in the manufacture of a medicament for the treatment of cancer.

In another embodiment, the cancer is ErbB2 positive.

In another embodiment, the cancer is selected from breast, gastric, biliary, colorectal, brain, lung, NSCLC, pancreatic, head and neck, ovarian and uterine cancer.

In another embodiment, the cancer is selected from breast, gastric, biliary, colorectal, lung, NSCLC, pancreatic, head and neck, ovarian and uterine cancer.

In another embodiment, the cancer is selected from breast, gastric, colorectal, lung and ovarian cancer.

In another embodiment, the cancer is selected from breast, ovarian, gastric and uterine cancer.

In another embodiment, the cancer is selected from breast, gastric, colorectal, NSCLC and ovarian cancer.

In another embodiment, the cancer is selected from breast, lung, pancreatic, colorectal and head and neck cancers.

In another embodiment, the cancer is breast cancer.
In another embodiment, the cancer is gastric cancer.
In another embodiment, the cancer is biliary cancer.
In another embodiment, the cancer is colorectal.
In another embodiment, the cancer is lung cancer.
In another embodiment, the cancer is NSCLC.
In another embodiment, the cancer is pancreatic cancer.
In another embodiment, the cancer is head and neck cancer.
In another embodiment, the cancer is ovarian cancer.
In another embodiment, the cancer is uterine cancer.
In another embodiment, the cancer is brain cancer.

In another embodiment, a method of treating or preventing a disease or disorder modulated by ErbB2, comprising administering to a mammal in need of such treatment an effective amount of a pharmaceutical composition described herein. Examples of such diseases and disorders include, but are not limited to, cancer.

Another embodiment provides a compound described herein in the treatment of disease. In a further embodiment, the disease is a hyperproliferative disease. In a further embodiment, the hyperproliferative disease is cancer.

Another embodiment provides the use of a pharmaceutical composition described herein, in the manufacture of a medicament for the treatment of cancer.

Combination Therapy

The polymorphs and pharmaceutical compositions described herein may be employed alone or in combination with other therapeutic agents for treatment. The compounds described herein may be used in combination with one or more additional drugs, for example an anti-hyperproliferative (or anti-cancer) agent that works through action on a different target protein. The second compound of the pharmaceutical combination formulation or dosing regimen preferably has complementary activities to the compound described herein, such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

For illustrative purposes, the following Examples are included. However, it is to be understood that these Examples do not limit the invention and are only meant to suggest a method of practicing the invention. Persons skilled in the art will recognize that the chemical reactions described herein may be readily adapted to prepare the compounds or polymorphs described herein, and alternative methods for preparing the compounds or polymorphs are deemed to be within the scope of this invention. For example, the synthesis of the compounds or polymorphs may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing the compounds or polymorphs described herein. Persons skilled in the art will also recognize that the polymorphs and compositions described may be readily adapted to prepare other polymorphs and compositions, and alternative methods for preparing the polymorphs and compositions, as well as alternative compositions are deemed to be within the scope of this invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

The XRPD analysis was conducted using a Rigaku X-Ray powder diffractometer (model Ultima III) operating with a Cu radiation source at 40 kW, 40 mA. Round standard aluminum sample holders with round zero background, and/or quartz plates were used for sample preparation. The scanning parameters were from a range of about 3-40 degree 2θ (±0.2 degrees) and a continuous scan at a rate of about 2 degrees 2θ/minute. 2θ calibration was performed using a Si standard.

Peak assignment analysis was performed using Materials Data Inc. Jade 7 (Version V5.1.2600) program, which uses a peak search algorithm that is based on the Savitzky-Golay 2nd derivatives combined with the counting statistics of intensity data. The peak search on each crystal form was performed using the following parameters: Parabolic Filter, Peak Threshold=3.0, Intensity Cutoff=0.1%, Background=3/1.0 and Peak Location=Summit. The Tables below include the analysis and are provided with the following approximate data: 2θ measured in degrees±0.2 degrees; d measured in angstroms±0.2 angstroms; and relative intensity using peak height to measure height % (H %) in counts per second.

Thermal transition values were measured by differential scanning calorimetry ("DSC") using a TA Instruments Q1000 DSC on approximately 2-10 mg samples in hermetically sealed aluminum pans with a pin-hole in the lid under an inert nitrogen atmosphere. A heating rate of 10° C./min was used over the 25-275° C. temperature range, and a second, empty aluminum pan was used as a reference.

Glass transition values were measured by modulated differential scanning calorimetry ("mDSC") using a TA Instruments Q1000 DSC on approximately 2-10 mg samples in hermetically sealed aluminum pans with a pin-hole in the lid under an inert nitrogen atmosphere. A heating rate of 2° C./min with a modulation amplitude of +/−1.3° C. over a period of 60 seconds was used. Samples were analyzed over a 25-150° C. temperature range, and a second, empty aluminum pan was used as a reference.

Example 1

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form A Amorphous N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine (20 mg) was added to a vial containing 1:1 EtOH:water (0.5 mL) and stirred for 48 hours at 50° C. The solution was cooled and filtered to yield Form A (Hydrate).

The XRPD scan is shown in FIG. 1 and the peak assignments are in Table 1:

TABLE 1

| 2θ | d (Å) | Relative Intensity |
|---|---|---|
| 6.86 | 12.8745 | 34.5 |
| 9.158 | 9.6484 | 13.3 |
| 9.442 | 9.3588 | 18.5 |
| 9.723 | 9.0893 | 23.1 |
| 10.623 | 8.3213 | 29.6 |
| 10.943 | 8.0784 | 21.9 |
| 11.416 | 7.7451 | 13 |
| 12.78 | 6.921 | 49.4 |
| 13.637 | 6.4881 | 35.1 |
| 14.959 | 5.9175 | 6.7 |
| 15.219 | 5.8169 | 27.4 |
| 16.3 | 5.4336 | 48.8 |
| 16.94 | 5.2296 | 66.1 |
| 17.464 | 5.074 | 27.1 |
| 17.92 | 4.946 | 11.9 |
| 18.139 | 4.8867 | 12.3 |
| 18.339 | 4.8338 | 13.7 |
| 18.745 | 4.73 | 7.8 |
| 19.138 | 4.6337 | 87.5 |
| 19.44 | 4.5624 | 36.3 |
| 20.278 | 4.3758 | 100 |
| 20.885 | 4.2499 | 22 |
| 21.16 | 4.1952 | 51.3 |
| 21.863 | 4.062 | 69.2 |
| 22.098 | 4.0194 | 16.5 |
| 22.604 | 3.9305 | 8.2 |
| 23.139 | 3.8408 | 78.8 |
| 23.98 | 3.708 | 32.7 |

TABLE 1-continued

| 2θ | d (Å) | Relative Intensity |
|---|---|---|
| 24.519 | 3.6276 | 44.2 |
| 25.202 | 3.5308 | 72.1 |
| 25.901 | 3.4371 | 24.4 |
| 26.181 | 3.401 | 20.2 |
| 26.86 | 3.3166 | 13.2 |
| 27.298 | 3.2643 | 31.9 |
| 27.733 | 3.2141 | 15.6 |
| 28.305 | 3.1504 | 7.4 |
| 28.864 | 3.0907 | 7.7 |
| 29.339 | 3.0417 | 16.6 |
| 29.66 | 3.0095 | 5.6 |
| 30.237 | 2.9534 | 5.3 |
| 30.642 | 2.9153 | 6.1 |
| 31.22 | 2.8626 | 11.9 |
| 32.042 | 2.791 | 5.7 |
| 32.459 | 2.7561 | 6.1 |
| 33.061 | 2.7073 | 15.9 |
| 33.318 | 2.687 | 4 |
| 33.802 | 2.6496 | 4.4 |
| 34.46 | 2.6005 | 8.9 |
| 35.679 | 2.5144 | 5.4 |
| 37.223 | 2.4136 | 3.8 |
| 38.178 | 2.3554 | 3.5 |
| 38.49 | 2.337 | 3.9 |

6.86, 9.723, 10.623, 12.78, 13.637, 15.219, 16.3, 16.94, 17.464, 19.138, 19.44, 20.278, 21.16, 21.863, 23.139, 23.98, 24.519, 25.202, 25.901, 27.298

Example 2

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Methanol Isomorphic Solvate N4-(4-([1,2,4]Triazolo[1,5-c]pyridin-7-yloxy)-3-methylphenyl)-N6-(4,4-dimethyl-4,5-dihydrooxazol-2-yl)quinazoline-4,6-diamine Form E (666.5 mg) was added to a 20 mL scint vial, and MeOH was added (3.0 mL). The suspension was stirred with a magnetic stirrer at room temperature overnight. The suspension was filtered and washed with MeOH (2.0 mL). The solids were dried at 45° C. under vacuum for about 5 hours and then dissolved at reflux in MeOH (50 mL). The solution was allowed to cool and placed in a refrigerator at about 5° C. for 5 days. The resulting solids were collected by filtration after reducing the solvent volume using a rotovap to yield Form B Methanol.

The XRPD scan is shown in FIG. 2 and the peak assignments are in Table 2:

TABLE 2

| 2θ | d (Å) | Relative Intensity |
|---|---|---|
| 6.881 | 12.836 | 6.9 |
| 8.46 | 10.4428 | 68.3 |
| 8.838 | 9.997 | 32.9 |
| 9.98 | 8.8555 | 100 |
| 10.297 | 8.5837 | 29.3 |
| 11.448 | 7.7236 | 10.1 |
| 12.917 | 6.8483 | 9.8 |
| 13.438 | 6.5839 | 72.7 |
| 14.124 | 6.2653 | 9.6 |
| 15.802 | 5.6037 | 39.5 |
| 16.243 | 5.4526 | 22.9 |
| 16.981 | 5.2171 | 60.7 |
| 17.4 | 5.0925 | 23.8 |

TABLE 2-continued

| 2θ | d (Å) | Relative Intensity |
|---|---|---|
| 18.042 | 4.9128 | 53 |
| 18.48 | 4.7971 | 25.6 |
| 19.72 | 4.4982 | 39.9 |
| 20.799 | 4.2672 | 53.5 |
| 21.143 | 4.1987 | 37.6 |
| 21.622 | 4.1067 | 44.3 |
| 23.161 | 3.8371 | 49.4 |
| 23.579 | 3.7701 | 18.1 |
| 24.72 | 3.5986 | 59.5 |
| 25.519 | 3.4877 | 84.4 |
| 27.736 | 3.2137 | 6.2 |
| 28.278 | 3.1533 | 9.8 |
| 30.063 | 2.9701 | 20.2 |
| 32.469 | 2.7553 | 6.4 |
| 33.173 | 2.6984 | 7.6 |
| 33.926 | 2.6402 | 6.9 |
| 34.484 | 2.5988 | 7.9 |

8.46, 8.838, 9.98, 10.297, 13.438, 15.802, 16.243, 16.981, 17.4, 18.042, 18.48, 19.72, 20.799, 21.143, 21.622, 23.161, 23.579, 24.72, 25.519, 30.063

Example 3

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Ethanol Isomorphic Solvate Absolute ethanol (8.5 L) (10-16 mL/g) was added to a vial containing a mixture of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine polymorphs (553 g; prepared as described above in Synthesis of Compounds section) and then heated to 70° C. The suspension was cooled to room temperature and agitated for over 12 hours. The suspension was filtered and washed twice with absolute ethanol (2×670 mL). The solids were dried in a vacuum oven at between 55° C. and 60° C. at 40 torr with a nitrogen bleed to yield Form B Ethanol (74.3% yield).

The XRPD scan is shown in FIG. 3 and the peak assignments are in Table 3:

TABLE 3

| 2θ | d (Å) | Relative Intensity |
|---|---|---|
| 8.358 | 10.5709 | 20.9 |
| 8.752 | 10.095 | 4.6 |
| 9.859 | 8.9643 | 56.6 |
| 10.217 | 8.6507 | 7.9 |
| 10.748 | 8.2247 | 3.1 |
| 11.394 | 7.7598 | 5.5 |
| 13.3 | 6.6515 | 50 |
| 13.886 | 6.3722 | 5.1 |
| 15.642 | 5.6607 | 25.4 |
| 15.94 | 5.5555 | 6.5 |
| 16.862 | 5.2539 | 38.4 |
| 17.298 | 5.1224 | 19.2 |
| 17.94 | 4.9404 | 39.8 |
| 18.195 | 4.8718 | 26.1 |
| 18.384 | 4.822 | 12.7 |
| 19.342 | 4.5853 | 5.8 |
| 19.602 | 4.5252 | 38.8 |
| 20.718 | 4.2838 | 51.5 |
| 21.04 | 4.219 | 29.1 |
| 21.502 | 4.1293 | 46.3 |
| 22.402 | 3.9654 | 9 |
| 22.801 | 3.897 | 8 |

TABLE 3-continued

| 2θ | d (Å) | Relative Intensity |
|---|---|---|
| 23.08 | 3.8505 | 38.5 |
| 23.444 | 3.7915 | 15.1 |
| 24.019 | 3.702 | 3.5 |
| 24.278 | 3.6631 | 4.3 |
| 24.621 | 3.6128 | 71.9 |
| 25.419 | 3.5013 | 100 |
| 25.785 | 3.4523 | 6 |
| 26.202 | 3.3983 | 12.3 |
| 28.275 | 3.1537 | 5 |
| 28.978 | 3.0788 | 4.7 |
| 29.94 | 2.982 | 15.1 |
| 30.764 | 2.904 | 4.8 |
| 31.196 | 2.8648 | 2.1 |
| 32.057 | 2.7897 | 4.2 |
| 32.959 | 2.7154 | 5.3 |
| 33.635 | 2.6624 | 4.6 |
| 34.102 | 2.627 | 5.8 |
| 35.006 | 2.5612 | 5.4 |
| 35.621 | 2.5184 | 5.1 |
| 37.3 | 2.4088 | 2.5 |
| 38.258 | 2.3506 | 7.6 |
| 38.935 | 2.3113 | 2.9 |
| 39.578 | 2.2752 | 4.3 |

8.358, 9.859, 13.3, 15.642, 16.862, 17.298, 17.94, 18.195, 18.384, 19.602, 20.718, 21.04, 21.502, 22.402, 23.08

Example 4

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Isopropyl Alcohol Isomorphic Solvate IPA (50 mL) was added to a flask containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A (5.0 g) and was heated to reflux. Additional IPA (20 mL) was added and continued to heat at reflux. The solution was left stirring and allowed to cool to room temperature and then stored in a refrigerator overnight. The suspension was filtered and dried at room temperature to yield Form B Isopropyl Alcohol.

The XRPD scan is shown in FIG. 4 and the peak assignments are in Table 4:

TABLE 4

| 2θ | d (Å) | Relative Intensity |
|---|---|---|
| 8.283 | 10.6656 | 41.6 |
| 8.661 | 10.2012 | 7.5 |
| 9.78 | 9.0365 | 95.7 |
| 10.273 | 8.6041 | 15.8 |
| 11.34 | 7.7963 | 11.1 |
| 13.201 | 6.7013 | 65.7 |
| 13.879 | 6.3757 | 8.2 |
| 15.498 | 5.7128 | 24.3 |
| 15.9 | 5.5694 | 6.1 |
| 16.88 | 5.2482 | 100 |
| 17.24 | 5.1394 | 15.1 |
| 17.899 | 4.9515 | 88 |
| 18.378 | 4.8237 | 25.8 |
| 19.259 | 4.6049 | 34.5 |
| 19.542 | 4.5389 | 25.2 |
| 20.6 | 4.3081 | 97.5 |
| 21.202 | 4.1872 | 48.1 |
| 21.48 | 4.1336 | 33.8 |
| 22.2 | 4.0011 | 7.8 |

TABLE 4-continued

| 2θ | d (Å) | Relative Intensity |
|---|---|---|
| 22.981 | 3.8669 | 48 |
| 23.38 | 3.8017 | 10.8 |
| 24.198 | 3.675 | 45.9 |
| 24.582 | 3.6185 | 48.2 |
| 25.082 | 3.5475 | 67.8 |
| 25.362 | 3.5089 | 66.2 |
| 25.802 | 3.4501 | 7.3 |
| 26.239 | 3.3937 | 9.2 |
| 27.981 | 3.1862 | 4.9 |
| 29.879 | 2.988 | 21.5 |
| 31.884 | 2.8045 | 4.3 |
| 32.977 | 2.714 | 8.3 |
| 34.024 | 2.6329 | 6.6 |
| 34.985 | 2.5627 | 6 |
| 35.618 | 2.5186 | 6.9 |
| 36.354 | 2.4693 | 5.5 |
| 36.866 | 2.4361 | 3.9 |
| 38.082 | 2.3611 | 5.5 |

8.283, 9.78, 10.273, 11.34, 13.201, 15.498, 16.88, 17.24, 17.899, 18.378, 19.259, 19.542, 20.6, 21.202, 21.48, 24.198, 24.582, 25.082, 25.362, 29.879,

Example 5

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Acetonitrile Isomorphic Solvate ACN (4 mL) was added to a 20 mL scint vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (647.9 mg), and the suspension was stirred magnetically at room temperature overnight. The suspension was filtered and washed with ACN (2 mL). The solids were dried at 45° C. under vacuum for about 5 hours to yield Form B Acetonitrile.

The XRPD scan is shown in FIG. 5 and the peak assignments are in Table 5:

TABLE 5

| 2θ | d (Å) | Relative Intensity |
|---|---|---|
| 8.46 | 10.4428 | 43.2 |
| 8.818 | 10.0203 | 15.3 |
| 9.98 | 8.8559 | 95.3 |
| 10.899 | 8.1114 | 8.3 |
| 13.46 | 6.5729 | 55.5 |
| 14.163 | 6.2484 | 9.6 |
| 15.82 | 5.5973 | 18.1 |
| 16.921 | 5.2357 | 56.3 |
| 17.442 | 5.0805 | 31.3 |
| 18.12 | 4.8916 | 46.4 |
| 18.438 | 4.808 | 28.4 |
| 19.426 | 4.5657 | 5.8 |
| 19.842 | 4.471 | 35 |
| 20.821 | 4.2629 | 30.4 |
| 21.239 | 4.1798 | 35.2 |
| 21.741 | 4.0844 | 50.1 |
| 22.64 | 3.9243 | 11.3 |
| 23.319 | 3.8116 | 38.5 |
| 24.899 | 3.5731 | 61.5 |
| 25.661 | 3.4687 | 100 |
| 26.464 | 3.3653 | 18.7 |
| 28.283 | 3.1528 | 6.3 |
| 30.16 | 2.9607 | 16.6 |
| 31.946 | 2.7992 | 3.8 |

TABLE 5-continued

| 2θ | d (Å) | Relative Intensity |
|---|---|---|
| 32.438 | 2.7579 | 4.8 |
| 33.042 | 2.7088 | 7.2 |
| 33.944 | 2.6389 | 9 |
| 34.539 | 2.5947 | 6.8 |

8.46, 8.818, 9.98, 13.46, 14.163, 15.82, 16.921, 17.442, 18.12, 18.438, 19.842, 20.821, 21.239, 21.741, 22.64, 23.319, 24.899, 25.661, 26.464, 30.16

Example 6

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Acetone Isomorphic Solvate Acetone (1 mL) was added to a 20 mL scint vial containing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (113.0 mg), and the suspension was stirred with a magnetic stirrer at room temperature for about 2 hours. N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form E (503.5 mg) and acetone (2 mL) were added, and the suspension was magnetically stirred at room temperature overnight. The suspension was filtered and washed with acetone (2 mL). The solids were dried at 45° C. under vacuum for about 5 hours. The solids were slurried at reflux in acetone (100 mL), allowed to cool and stored in a refrigerator at about 5° C. for over 5 days. The solvent was removed by rotovap, and the solids were collected by filtration to yield Form B Acetone.

The XRPD scan is shown in FIG. 6 and the peak assignments are in Table 6:

TABLE 6

| 2θ | d (Å) | Relative Intensity |
|---|---|---|
| 5.785 | 15.2648 | 7.3 |
| 8.378 | 10.5448 | 45.5 |
| 8.678 | 10.1814 | 11.3 |
| 9.936 | 8.8948 | 100 |
| 10.342 | 8.547 | 10.7 |
| 10.778 | 8.202 | 3.7 |
| 11.481 | 7.7015 | 15.6 |
| 13.041 | 6.7832 | 40.3 |
| 13.378 | 6.613 | 27.8 |
| 14.12 | 6.267 | 8.3 |
| 15.461 | 5.7265 | 12.4 |
| 16.119 | 5.4942 | 5.3 |
| 17.02 | 5.2052 | 70.8 |
| 17.98 | 4.9295 | 49.9 |
| 18.478 | 4.7977 | 27.5 |
| 19.068 | 4.6506 | 3.9 |
| 19.758 | 4.4897 | 37.6 |
| 20.302 | 4.3706 | 31.7 |
| 20.759 | 4.2754 | 27.2 |
| 21.041 | 4.2188 | 33 |
| 21.821 | 4.0698 | 32.2 |
| 22.481 | 3.9518 | 18 |
| 23.14 | 3.8406 | 18.6 |
| 23.498 | 3.783 | 35.8 |
| 24.679 | 3.6045 | 60.2 |
| 25.52 | 3.4875 | 85.2 |
| 26.312 | 3.3843 | 5 |

TABLE 6-continued

| 2θ | d (Å) | Relative Intensity |
|---|---|---|
| 26.641 | 3.3434 | 6.1 |
| 28.119 | 3.1709 | 7.7 |
| 28.985 | 3.0781 | 3.8 |
| 30.061 | 2.9703 | 15.2 |
| 32.099 | 2.7862 | 4 |
| 33.016 | 2.7109 | 3.9 |
| 33.757 | 2.653 | 3.9 |

8.378, 9.936, 11.481, 13.041, 13.378, 15.461, 17.02, 17.98, 18.478, 19.758, 20.302, 20.759, 21.041, 21.821, 22.481, 23.14, 23.498, 24.679, 25.52, 30.061

Example 7

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Dichloromethane Isomorphic Solvate DCM (1 mL) was added to a 20 mL scint vial containing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (181.7 mg), and the suspension was stirred with a magnetic stirrer at room temperature for about 2 hours. N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form E (506.3 mg) and DCM (2 mL) were added, and the suspension was magnetically stirred at room temperature overnight. The suspension was filtered and washed with DCM (2 mL). The solids were dried at 45° C. under vacuum for about 5 hours. The solids were slurried at reflux in DCM (5 mL), allowed to cool and stored in a refrigerator at about 5° C. for over 5 days. The solids were collected by filtration to yield Form B Dichloromethane.

The XRPD scan is shown in FIG. 7 and the peak assignments are in Table 7:

TABLE 7

| 2θ | d (Å) | Relative Intensity |
|---|---|---|
| 7.96 | 11.0985 | 28 |
| 8.439 | 10.4697 | 55.9 |
| 8.817 | 10.0216 | 12.6 |
| 9.517 | 9.2861 | 19 |
| 9.977 | 8.8582 | 84.5 |
| 10.265 | 8.6109 | 29.3 |
| 11.47 | 7.7085 | 18.5 |
| 12.579 | 7.0311 | 21.8 |
| 13.381 | 6.6116 | 88.6 |
| 15.796 | 5.6059 | 32.4 |
| 16.918 | 5.2364 | 100 |
| 17.438 | 5.0814 | 37.3 |
| 18.041 | 4.9128 | 57.4 |
| 18.34 | 4.8335 | 45.8 |
| 19.336 | 4.5867 | 18.1 |
| 19.899 | 4.4582 | 48 |
| 20.738 | 4.2797 | 81.9 |
| 21.161 | 4.1951 | 38.9 |
| 21.802 | 4.0732 | 44.8 |
| 23.46 | 3.789 | 48.8 |
| 24.779 | 3.5902 | 72.2 |
| 25.641 | 3.4715 | 75.3 |
| 26.441 | 3.3681 | 16.4 |
| 28.27 | 3.1543 | 16.5 |

TABLE 7-continued

| 2θ | d (Å) | Relative Intensity |
|---|---|---|
| 30.319 | 2.9456 | 16.3 |
| 34.536 | 2.5949 | 11.3 |

7.96, 8.439, 9.517, 9.977, 10.265, 11.47, 12.579, 13.381, 15.796, 16.918, 17.438, 18.041, 18.34, 19.899, 20.738, 21.161, 21.802, 23.46, 24.779, 25.641

Example 8

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Tetrahydrofuran Isomorphic Solvate THF (4 mL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran (300 mg), and the contents were agitated at room temperature. The contents were filtered and washed with THF (3×0.8 mL). The solids were dried in a vacuum oven at 45° C. with a nitrogen bleed to yield Form B Tetrahydrofuran (91.8% yield).

The XRPD scan is shown in FIG. 8 and the peak assignments are in Table 8:

TABLE 8

| 2θ | d (Å) | Relative Intensity |
|---|---|---|
| 8.262 | 10.6932 | 33 |
| 8.679 | 10.1799 | 15.5 |
| 9.819 | 9.0002 | 84.9 |
| 10.718 | 8.2473 | 7.1 |
| 13.38 | 6.6123 | 61.1 |
| 13.96 | 6.3388 | 12.5 |
| 15.72 | 5.6327 | 22.4 |
| 16.7 | 5.3042 | 65.3 |
| 17.179 | 5.1575 | 26.2 |
| 17.92 | 4.9459 | 70.9 |
| 19.541 | 4.5392 | 30.8 |
| 20.58 | 4.3121 | 21.6 |
| 21.4 | 4.1489 | 58.7 |
| 22.92 | 3.877 | 40.7 |
| 24.66 | 3.6072 | 64 |
| 25.44 | 3.4984 | 100 |
| 26.079 | 3.414 | 20.6 |
| 28.28 | 3.1532 | 4.1 |
| 29.84 | 2.9918 | 13.8 |
| 32.237 | 2.7746 | 3.9 |
| 32.781 | 2.7298 | 5.2 |
| 33.7 | 2.6574 | 7.7 |
| 35.262 | 2.5432 | 7.2 |
| 37.296 | 2.4091 | 2.6 |
| 38.335 | 2.3461 | 3.8 |
| 39.4 | 2.2851 | 2.2 |

8.262, 8.679, 9.819, 10.718, 13.38, 13.96, 15.72, 16.7, 17.179, 17.92, 19.541, 20.58, 21.4, 22.92, 24.66, 25.44, 26.079, 29.84, 33.7, 35.262

Example 9

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Anhydrous N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Ethanol (1.10 g) was placed in a watch glass, which was then placed in an oven at 100° C. with nitrogen flowing through it. The solid was removed after 5 days and placed in a 25 mL round bottom flask and heated to 200° C. under high vacuum for 1 hour. The sample was again placed in the oven at 200° C. under high vacuum for 3 hours. The solids were collected in a 20 mL scint vial to yield Form B Anhydrous.

The XRPD scan is shown in FIG. 9 and the peak assignments are in Table 9:

TABLE 9

| 2θ | d (Å) | Relative Intensity |
|---|---|---|
| 8.44 | 10.4679 | 37.8 |
| 8.855 | 9.9777 | 18.7 |
| 9.938 | 8.8932 | 100 |
| 10.902 | 8.1086 | 9 |
| 12.642 | 6.9962 | 2.4 |
| 13.641 | 6.4863 | 54.2 |
| 14.28 | 6.1975 | 12.4 |
| 16.016 | 5.5294 | 25.5 |
| 16.841 | 5.2602 | 43.8 |
| 17.099 | 5.1813 | 37.1 |
| 17.439 | 5.0813 | 27 |
| 18.1 | 4.8971 | 54.1 |
| 18.42 | 4.8127 | 22.9 |
| 19.697 | 4.5035 | 25.8 |
| 20.222 | 4.3877 | 5.8 |
| 20.704 | 4.2867 | 11.1 |
| 21.22 | 4.1835 | 42.8 |
| 21.498 | 4.1301 | 45.6 |
| 22.56 | 3.9381 | 4.1 |
| 23 | 3.8636 | 24.7 |
| 23.538 | 3.7766 | 14.6 |
| 24.901 | 3.5729 | 35.1 |
| 25.541 | 3.4848 | 60.4 |
| 26.159 | 3.4038 | 13.6 |
| 28.078 | 3.1754 | 1.7 |
| 28.558 | 3.1231 | 2.9 |
| 29.213 | 3.0545 | 2.4 |
| 29.879 | 2.9879 | 9.4 |
| 30.242 | 2.9529 | 3.5 |
| 31.379 | 2.8485 | 2.6 |
| 31.845 | 2.8079 | 2.3 |
| 32.416 | 2.7597 | 2.9 |
| 32.944 | 2.7166 | 3.3 |
| 33.943 | 2.6389 | 4.1 |
| 34.657 | 2.5862 | 1.7 |
| 35.463 | 2.5292 | 5.5 |
| 37.385 | 2.4035 | 1.9 |
| 38.582 | 2.3316 | 2.7 |
| 39.558 | 2.2764 | 1.3 |

8.44, 8.855, 9.938, 13.641, 14.28, 16.016, 16.841, 17.099, 17.439, 18.1, 18.42, 19.697, 20.704, 21.22, 21.498, 23, 23.538, 24.901, 25.541, 26.159

Example 10

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form C 2-Methoxyethanol (200 mL) was added to a 500 mL Erlenmeyer flask containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A (15.11 g), and the solution was heated to 50° C. with stirring. The flask was cooled to room temperature, and the volume was reduced to about 50 mL by rotovap. The flask was allowed to stand for 2 hours. EtOH (200 mL) was added, and the contents of the flask were stirred, filtered and washed with EtOH (3×15 mL). The solid was dried at 50° C. under vacuum overnight to yield Form C (Anhydrous).

The XRPD scan is shown in FIG. 10 and the peak assignments are in Table 10:

TABLE 10

| 2θ | d (Å) | Relative Intensity |
|---|---|---|
| 5.04 | 17.52 | 100 |
| 7.159 | 12.3378 | 69.6 |
| 10.159 | 8.7004 | 68.2 |
| 11.376 | 7.772 | 16.2 |
| 11.902 | 7.4299 | 29.8 |
| 12.16 | 7.2724 | 9.2 |
| 12.977 | 6.8163 | 17.9 |
| 14.435 | 6.1313 | 76.8 |
| 15.301 | 5.786 | 99.8 |
| 15.717 | 5.6338 | 66.7 |
| 16.121 | 5.4936 | 29.8 |
| 16.719 | 5.2985 | 43.3 |
| 17.501 | 5.0632 | 76.3 |
| 18.059 | 4.908 | 36.8 |
| 18.437 | 4.8084 | 88.4 |
| 18.902 | 4.6911 | 90.7 |
| 19.638 | 4.5168 | 74.1 |
| 20.479 | 4.3333 | 30.7 |
| 21.08 | 4.2111 | 42.2 |
| 21.437 | 4.1418 | 42.3 |
| 21.74 | 4.0848 | 27.8 |
| 22.34 | 3.9763 | 52.8 |
| 22.878 | 3.884 | 24.6 |
| 23.779 | 3.7389 | 32 |
| 24.181 | 3.6776 | 64.8 |
| 24.58 | 3.6188 | 33.1 |
| 25.262 | 3.5226 | 11 |
| 25.679 | 3.4663 | 11 |
| 26.096 | 3.4119 | 29.8 |
| 26.809 | 3.3228 | 5.8 |
| 27.18 | 3.2783 | 19.1 |
| 27.675 | 3.2208 | 8.4 |
| 27.88 | 3.1975 | 8.6 |
| 28.417 | 3.1383 | 16 |
| 28.599 | 3.1187 | 16.3 |
| 30.021 | 2.9742 | 7.6 |
| 31.113 | 2.8722 | 5.5 |
| 31.863 | 2.8063 | 6.6 |
| 32.674 | 2.7385 | 5.9 |
| 33.339 | 2.6853 | 17.7 |
| 34.234 | 2.6171 | 6 |
| 34.878 | 2.5703 | 8.6 |
| 37.442 | 2.4 | 8.9 |

5.04, 7.159, 10.159, 11.902, 14.435, 15.301, 15.717, 16.121, 16.719, 17.501, 18.059, 18.437, 18.902, 19.638, 20.479, 21.08, 21.437, 22.34, 23.779, 24.181, 24.58, 26.096

Example 11

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form D Ethyl Acetate Isomorphic Solvate EtOAc (2.0 mL) was added to a 4 mL vial containing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (394 mg), and the contents were stirred overnight at room temperature. The solids were dried under a stream of nitrogen to yield Form D Ethyl Acetate.

The XRPD scan is shown in FIG. 11 and the peak assignments are in Table 11:

TABLE 11

| 2θ | d (Å) | Relative Intensity |
|---|---|---|
| 5.596 | 15.7789 | 13.5 |
| 6.741 | 13.1015 | 11 |
| 7.959 | 11.0998 | 100 |
| 9.139 | 9.669 | 3.4 |
| 9.798 | 9.0196 | 38.7 |
| 11.321 | 7.8099 | 35.5 |
| 12.66 | 6.9863 | 61.3 |
| 13.917 | 6.3581 | 33.9 |
| 16.099 | 5.501 | 54.8 |
| 17.118 | 5.1757 | 48.3 |
| 18.017 | 4.9194 | 33.9 |
| 18.937 | 4.6825 | 6.4 |
| 19.761 | 4.489 | 47.4 |
| 21.379 | 4.1529 | 28.2 |
| 22.139 | 4.012 | 23.9 |
| 22.557 | 3.9386 | 7.6 |
| 22.93 | 3.8753 | 5.9 |
| 23.599 | 3.7669 | 38.3 |
| 24.241 | 3.6686 | 18.7 |
| 25.34 | 3.512 | 13.7 |
| 25.66 | 3.4689 | 15.5 |
| 27.52 | 3.2385 | 33.6 |
| 28.142 | 3.1684 | 5.4 |
| 28.724 | 3.1054 | 4.6 |
| 29.023 | 3.0742 | 4.7 |
| 29.359 | 3.0397 | 4.4 |
| 30.045 | 2.9719 | 2.7 |
| 31.56 | 2.8326 | 4.8 |
| 32.093 | 2.7867 | 3.8 |
| 32.701 | 2.7363 | 2.7 |
| 33.243 | 2.6929 | 3.5 |
| 37.161 | 2.4175 | 2.7 |

5.596, 6.741, 7.959, 9.798, 11.321, 12.66, 13.917, 16.099, 17.118, 18.017, 18.937, 19.761, 21.379, 22.139, 22.557, 23.599, 24.241, 25.34, 25.66, 27.52

Example 12

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form D Dioxane Isomorphic Solvate Dioxane (600 μL) was added to a vial containing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (90 mg), and the contents were allowed to stir overnight. The solids were filtered and dried at room temperature to yield Form D Dioxane.

The XRPD scan is shown in FIG. 12 and the peak assignments are in Table 12:

TABLE 12

| 2θ | d (Å) | Relative Intensity |
|---|---|---|
| 7.822 | 11.294 | 99.1 |
| 9.34 | 9.4615 | 30.3 |
| 9.759 | 9.0562 | 33.4 |
| 11.139 | 7.9369 | 98.7 |
| 12.5 | 7.0753 | 86.2 |
| 13.378 | 6.6132 | 16.1 |
| 13.763 | 6.429 | 32.4 |
| 15.841 | 5.5899 | 17 |
| 16.461 | 5.3808 | 32.6 |

TABLE 12-continued

| 2θ | d (Å) | Relative Intensity |
|---|---|---|
| 17.135 | 5.1708 | 43.3 |
| 17.703 | 5.0059 | 35 |
| 19.54 | 4.5394 | 100 |
| 21.062 | 4.2146 | 84.1 |
| 21.901 | 4.0551 | 28 |
| 23.139 | 3.8409 | 89.2 |
| 24.022 | 3.7016 | 53 |
| 25.202 | 3.5309 | 33.4 |
| 27.179 | 3.2784 | 62.6 |
| 28.859 | 3.0912 | 18.6 |
| 37.578 | 2.3916 | 9.4 |
| 39.493 | 2.2799 | 9.1 |

7.822, 9.34, 9.759, 11.139, 12.5, 13.378, 13.763, 15.841, 16.461, 17.135, 17.703, 19.54, 21.062, 21.901, 23.139, 24.022, 25.202, 27.179, 28.859, 37.578

Example 13

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form D Acetone Isomorphic Solvate Acetone (300 μL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (100 mg), and the contents were allowed to stir overnight. The solids were filtered and dried at room temperature to yield Form D Acetone.

The XRPD scan is shown in FIG. 13 and the peak assignments are in Table 13:

TABLE 13

| 2θ | d (Å) | Relative Intensity |
|---|---|---|
| 5.656 | 15.6134 | 10.8 |
| 7.999 | 11.0445 | 100 |
| 8.603 | 10.2695 | 2.9 |
| 9.856 | 8.9671 | 43.6 |
| 11.359 | 7.7837 | 33.7 |
| 12.681 | 6.9748 | 48.3 |
| 13.923 | 6.3555 | 55.6 |
| 16.101 | 5.5003 | 59.5 |
| 17.14 | 5.169 | 83.3 |
| 17.625 | 5.0278 | 6.4 |
| 18 | 4.9241 | 36.7 |
| 18.941 | 4.6815 | 13.8 |
| 19.761 | 4.489 | 56.4 |
| 20.581 | 4.3121 | 7.2 |
| 21.378 | 4.153 | 63 |
| 22.103 | 4.0185 | 38.1 |
| 22.541 | 3.9413 | 13.9 |
| 22.9 | 3.8804 | 16 |
| 23.561 | 3.7729 | 71.5 |
| 24.259 | 3.6659 | 42.6 |
| 25.063 | 3.5501 | 5.8 |
| 25.339 | 3.5121 | 21.6 |
| 25.622 | 3.474 | 29.3 |
| 26.981 | 3.3019 | 11.2 |
| 27.482 | 3.2429 | 82.1 |
| 28.122 | 3.1705 | 15.5 |
| 28.723 | 3.1056 | 13.1 |
| 29.002 | 3.0763 | 10.1 |
| 29.339 | 3.0417 | 11.7 |
| 29.848 | 2.991 | 4.3 |
| 30.2 | 2.9569 | 4.1 |
| 31 | 2.8824 | 3.8 |
| 31.539 | 2.8344 | 5.1 |

TABLE 13-continued

| 2θ | d (Å) | Relative Intensity |
|---|---|---|
| 32.041 | 2.7911 | 10.8 |
| 32.662 | 2.7395 | 9.3 |
| 33.218 | 2.6949 | 7.6 |
| 33.611 | 2.6642 | 3.6 |
| 35.201 | 2.5474 | 4.1 |
| 35.675 | 2.5147 | 3.1 |
| 37.117 | 2.4203 | 8 |
| 39.058 | 2.3043 | 6 |

7.999, 9.856, 11.359, 12.681, 13.923, 16.101, 17.14, 18, 18.941, 19.761, 21.378, 22.103, 22.541, 22.9, 23.561, 24.259, 25.339, 25.622, 27.482, 28.122

Example 14

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form D Propyl Acetate Isomorphic Solvate Propyl acetate (400 μL) was added to a vial containing N4-(4-[1,2,4]triazolo[1,5-a]pyridin-7-yloxy)-3-methylphenyl)-N6-(4,4-dimethyl-4,5-dihydrooxazol-2-yl)quinazoline-4,6-diamine Form E (50 mg), and the contents were allowed to stir overnight. The solids were filtered and dried at room temperature to yield Form D Propyl Acetate.

The XRPD scan is shown in FIG. 14 and the peak assignments are in Table 14:

TABLE 14

| 2θ | d (Å) | Relative Intensity |
|---|---|---|
| 5.074 | 17.4026 | 6.3 |
| 5.623 | 15.7043 | 8.4 |
| 7.189 | 12.2862 | 5.2 |
| 7.999 | 11.0438 | 100 |
| 9.839 | 8.9821 | 43.1 |
| 10.158 | 8.7009 | 7.5 |
| 11.362 | 7.7816 | 32.3 |
| 12.719 | 6.9541 | 68.2 |
| 13.903 | 6.3648 | 39.7 |
| 14.381 | 6.1539 | 6.4 |
| 15.701 | 5.6395 | 10.3 |
| 16.121 | 5.4937 | 68.2 |
| 17.16 | 5.1633 | 84.4 |
| 17.574 | 5.0423 | 8.5 |
| 18.021 | 4.9183 | 38.5 |
| 18.419 | 4.813 | 9.8 |
| 18.96 | 4.677 | 19.2 |
| 19.782 | 4.4844 | 68.7 |
| 20.65 | 4.2977 | 7.7 |
| 21.42 | 4.1449 | 38.6 |
| 22.201 | 4.0008 | 33.5 |
| 22.596 | 3.9318 | 16.5 |
| 22.92 | 3.8771 | 15.1 |
| 23.62 | 3.7637 | 61.7 |
| 24.28 | 3.6629 | 45.7 |
| 25.379 | 3.5066 | 26.7 |
| 25.681 | 3.466 | 26.4 |
| 27.579 | 3.2317 | 54.1 |
| 28.825 | 3.0948 | 9.1 |
| 29.137 | 3.0623 | 10.8 |
| 29.365 | 3.0391 | 6.1 |
| 31.503 | 2.8376 | 8.4 |
| 32.019 | 2.793 | 5.2 |
| 32.699 | 2.7364 | 6 |
| 33.283 | 2.6898 | 7.8 |

TABLE 14-continued

| 2θ | d (Å) | Relative Intensity |
|---|---|---|
| 37.179 | 2.4164 | 4.6 |
| 39.104 | 2.3017 | 5 |

7.999, 9.839, 11.362, 12.719, 13.903, 16.121, 17.16, 18.021, 18.96, 19.782, 21.42, 22.201, 22.596, 22.92, 23.62, 24.28, 25.379, 25.681, 27.579, 29.137

Example 15

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form E N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine was synthesized from 1-(4-((4-([1,2,4]triazolo[1,5-c]pyridin-7-yloxy)-3-methylphenyl)amino)quinazolin-6-yl)-3-(1-hydroxy-2-methylpropan-2-yl)thiourea (322 g) in THF (3 L) at 0° C. Water (10 L) was added, and the solution was allowed to stir for 1 hour, at which point the material oiled out. The organcis were then extracted into ethyl acetate (3×5000 mL), combined and washed with water (2×5000 mL) and brine (2×5000 mL). The organics were dried by rotoevaporation, and the material was concentrated to an oil. The oil was observed to solidify at room temperature to yield Form E.

The XRPD scan is shown in FIG. 15 and the peak assignments are in Table 15:

TABLE 15

| 2θ | d (Å) | Relative Intensity |
|---|---|---|
| 8.659 | 10.204 | 44.5 |
| 9.353 | 9.4482 | 38.4 |
| 10 | 8.8382 | 4.8 |
| 11.904 | 7.4284 | 27.3 |
| 12.416 | 7.123 | 14.8 |
| 12.923 | 6.8451 | 19.3 |
| 15.36 | 5.7638 | 11 |
| 16.06 | 5.5143 | 100 |
| 16.338 | 5.421 | 16.6 |
| 16.709 | 5.3015 | 2.9 |
| 16.918 | 5.2363 | 8 |
| 17.457 | 5.0759 | 4.9 |
| 18.03 | 4.9158 | 3.8 |
| 18.4 | 4.8179 | 8.1 |
| 19.021 | 4.6621 | 11.2 |
| 19.619 | 4.5212 | 19.4 |
| 20.08 | 4.4186 | 23.4 |
| 20.656 | 4.2965 | 3.8 |
| 21.296 | 4.1689 | 18.1 |
| 21.62 | 4.107 | 12.6 |
| 22.179 | 4.0047 | 1.8 |
| 22.821 | 3.8935 | 18.4 |
| 23.739 | 3.745 | 43.6 |
| 24.358 | 3.6512 | 6.7 |
| 24.94 | 3.5674 | 2.7 |
| 25.295 | 3.518 | 3 |
| 25.459 | 3.4958 | 2.5 |
| 26.106 | 3.4107 | 3.5 |
| 27.035 | 3.2955 | 3.6 |
| 27.8 | 3.2065 | 6.8 |
| 28.297 | 3.1513 | 15.4 |
| 29.237 | 3.0521 | 2.3 |
| 30.716 | 2.9084 | 2.7 |
| 31.799 | 2.8118 | 4.9 |
| 32.507 | 2.7522 | 1.7 |

TABLE 15-continued

| 2θ | d (Å) | Relative Intensity |
|---|---|---|
| 36.658 | 2.4495 | 1.9 |
| 39.055 | 2.3045 | 1.5 |

8.659, 9.353, 11.904, 12.416, 12.923, 15.36, 16.06, 16.338, 16.918, 18.4, 19.021, 19.619, 20.08, 21.296, 21.62, 22.821, 23.739, 24.358, 27.8, 28.297

Example 16

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form F Ethyl acetate (5 mL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (1 g), and the contents were stirred for 48 hours. The solid was filtered and dried overnight in a vacuum oven at room temperature to yield Form F (Ethyl Acetate solvate).

The XRPD scan is shown in FIG. 16 and the peak assignments are in Table 16:

TABLE 16

| 2θ | d (Å) | Relative Intensity |
|---|---|---|
| 6.981 | 12.6512 | 8.2 |
| 7.58 | 11.6541 | 15 |
| 8.24 | 10.7212 | 14.5 |
| 9.483 | 9.3191 | 12.6 |
| 11.04 | 8.008 | 4.5 |
| 11.498 | 7.6901 | 32.5 |
| 12.321 | 7.178 | 9.5 |
| 12.859 | 6.8787 | 12.4 |
| 13.633 | 6.49 | 2.5 |
| 13.897 | 6.3675 | 2.7 |
| 14.899 | 5.9413 | 41.3 |
| 15.906 | 5.5673 | 4.1 |
| 16.56 | 5.3487 | 100 |
| 16.92 | 5.2357 | 50.2 |
| 18.502 | 4.7916 | 14.9 |
| 19.098 | 4.6433 | 87.8 |
| 19.62 | 4.5209 | 32.4 |
| 20.663 | 4.2952 | 12.9 |
| 21.18 | 4.1914 | 35.4 |
| 21.633 | 4.1046 | 8 |
| 22.24 | 3.994 | 22.1 |
| 22.537 | 3.942 | 35.1 |
| 23.004 | 3.8631 | 16.3 |
| 23.361 | 3.8047 | 9.3 |
| 23.996 | 3.7056 | 24.8 |
| 24.423 | 3.6417 | 6.6 |
| 24.942 | 3.567 | 26 |
| 25.379 | 3.5067 | 13.8 |
| 26.418 | 3.371 | 6.7 |
| 26.738 | 3.3314 | 4.4 |
| 27.34 | 3.2594 | 25.3 |
| 27.913 | 3.1938 | 4.3 |
| 28.38 | 3.1423 | 5.4 |
| 29.02 | 3.0744 | 15.7 |
| 29.915 | 2.9844 | 4.6 |
| 31.941 | 2.7996 | 4.5 |
| 33.417 | 2.6793 | 4.5 |
| 35.201 | 2.5475 | 4.8 |
| 36.042 | 2.4899 | 2.8 |

Example 17

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran Isomorphic Solvate THF:water (2 mL, 20:80) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran (100 mg), and the contents were stirred at room temperature overnight. The contents were then heated to 40° C. and stirred overnight. The solids were filtered and collected to yield Form G hemi-Tetrahydrofuran.

The XRPD scan is shown in FIG. 17 and the peak assignments are in Table 17:

TABLE 17

| 2θ | d (Å) | Relative Intensity |
|---|---|---|
| 5.148 | 17.1528 | 3.5 |
| 5.521 | 15.995 | 13.1 |
| 7.719 | 11.4438 | 91.4 |
| 8.018 | 11.0172 | 28.3 |
| 9.379 | 9.4216 | 28.6 |
| 11.102 | 7.963 | 42.1 |
| 12.281 | 7.201 | 49.9 |
| 12.737 | 6.9445 | 17.6 |
| 13.263 | 6.67 | 13.8 |
| 13.897 | 6.3673 | 3.3 |
| 14.097 | 6.2772 | 5.9 |
| 15.558 | 5.6909 | 20.2 |
| 16.142 | 5.4863 | 16.5 |
| 16.544 | 5.3541 | 32.6 |
| 16.955 | 5.2253 | 10.4 |
| 17.26 | 5.1336 | 16.1 |
| 17.519 | 5.0583 | 17.4 |
| 18.096 | 4.8982 | 16.6 |
| 18.837 | 4.7072 | 15.6 |
| 19.26 | 4.6047 | 16.8 |
| 19.72 | 4.4982 | 19.6 |
| 20.26 | 4.3795 | 22.6 |
| 20.645 | 4.2989 | 5.3 |
| 21.022 | 4.2225 | 30.3 |
| 21.243 | 4.1792 | 22.2 |
| 21.865 | 4.0617 | 7.5 |
| 22.6 | 3.9311 | 9.2 |
| 23.079 | 3.8507 | 100 |
| 23.359 | 3.8052 | 34.1 |
| 24.099 | 3.69 | 55.8 |
| 24.48 | 3.6333 | 11.5 |
| 24.934 | 3.5683 | 6.3 |
| 25.222 | 3.5281 | 10.7 |
| 26.839 | 3.3191 | 17.6 |
| 27.282 | 3.2662 | 16.1 |
| 27.503 | 3.2404 | 37.7 |
| 28.281 | 3.1531 | 6.7 |
| 28.52 | 3.1272 | 7.7 |
| 29.062 | 3.07 | 6.3 |
| 29.814 | 2.9943 | 9 |
| 31.297 | 2.8558 | 4.3 |
| 32.39 | 2.7619 | 5.4 |

Example 18

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form G mono-Tetrahydrofuran Isomorphic Solvate THF (150 mL) was added to a flask containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form A (5.17 g), and the contents were heated to reflux until all of the solids dissolved. The heat was removed, and the flask was allowed to cool to room temperature with stirring overnight. The volume was reduced to about 50 mL by nitrogen evaporation. The flask was stored in a refrigerator overnight. The contents of the flask were filtered and washed with THF (2×10 mL). The solids were dried at 50° C. under vacuum overnight to yield Form G mono-Tetrahydrofuran.

The XRPD scan is shown in FIG. 18 and the peak assignments are in Table 18:

TABLE 18

| 2θ | d (Å) | Relative Intensity |
|---|---|---|
| 5.522 | 15.9921 | 20.2 |
| 7.72 | 11.4432 | 87.8 |
| 8.003 | 11.039 | 45.6 |
| 9.417 | 9.3841 | 39.8 |
| 11.137 | 7.9379 | 60.5 |
| 12.401 | 7.1321 | 58.8 |
| 12.734 | 6.946 | 24.7 |
| 13.281 | 6.6612 | 16.6 |
| 13.825 | 6.4002 | 4.9 |
| 14.083 | 6.2837 | 9.5 |
| 15.559 | 5.6908 | 19.6 |
| 16.159 | 5.4806 | 19.6 |
| 16.599 | 5.3365 | 44.8 |
| 16.961 | 5.2233 | 18.7 |
| 17.318 | 5.1164 | 27.2 |
| 17.54 | 5.0521 | 18.3 |
| 18.14 | 4.8864 | 22.5 |
| 18.858 | 4.702 | 19.9 |
| 19.3 | 4.5952 | 17.8 |
| 19.739 | 4.4939 | 27.1 |
| 20.257 | 4.3802 | 21.8 |
| 21.017 | 4.2235 | 40.5 |
| 21.24 | 4.1796 | 29.3 |
| 22.601 | 3.9309 | 12.2 |
| 23.022 | 3.8601 | 100 |
| 23.397 | 3.799 | 38.6 |
| 24.042 | 3.6985 | 77.4 |
| 24.419 | 3.6423 | 11.8 |
| 25.222 | 3.5281 | 9.6 |
| 26.82 | 3.3214 | 23.9 |
| 27.482 | 3.2429 | 38.2 |
| 28.463 | 3.1333 | 10.5 |
| 29.06 | 3.0703 | 8.2 |
| 29.8 | 2.9957 | 8.5 |
| 30.664 | 2.9132 | 5.6 |
| 32.382 | 2.7625 | 7 |

Example 19

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form G Isopropyl Acetate Isomorphic Solvate Isopropyl acetate (5 mL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (500 mg), and the contents were stirred at room temperature for 48 hours. The contents were filtered and dried overnight in a vacuum oven at room temperature to yield Form G Isopropyl Acetate.

The XRPD scan is shown in FIG. 19 and the peak assignments are in Table 19:

TABLE 19

| 2θ | d (Å) | Relative Intensity |
|---|---|---|
| 5.601 | 15.765 | 18.2 |
| 7.803 | 11.3215 | 61.8 |
| 8.299 | 10.6452 | 55.3 |
| 9.361 | 9.4403 | 52.3 |
| 9.841 | 8.9804 | 11.8 |
| 11.398 | 7.7568 | 59.8 |
| 12.7 | 6.9646 | 49.6 |
| 13.18 | 6.712 | 52.7 |
| 14.026 | 6.3092 | 5 |
| 15.961 | 5.5483 | 34.8 |
| 16.64 | 5.3232 | 52.6 |
| 17.121 | 5.1748 | 28.6 |
| 17.457 | 5.076 | 10.6 |
| 18.099 | 4.8973 | 36.6 |
| 18.655 | 4.7526 | 22.1 |
| 19.04 | 4.6573 | 17.9 |
| 19.639 | 4.5166 | 38.4 |
| 19.979 | 4.4405 | 49.1 |
| 20.58 | 4.3122 | 26.8 |
| 21.323 | 4.1636 | 17.8 |
| 21.738 | 4.0851 | 46.5 |
| 22.58 | 3.9345 | 27.7 |
| 23.438 | 3.7924 | 100 |
| 23.739 | 3.745 | 32.1 |
| 24.381 | 3.6478 | 51.6 |
| 24.737 | 3.5961 | 34.4 |
| 25.084 | 3.5472 | 12.2 |
| 26.605 | 3.3478 | 10.1 |
| 27.821 | 3.2042 | 46.9 |
| 29.303 | 3.0454 | 6.8 |
| 29.899 | 2.986 | 14.5 |
| 31.171 | 2.867 | 5.3 |
| 31.641 | 2.8255 | 8.5 |
| 32.799 | 2.7283 | 5.4 |
| 33.295 | 2.6888 | 6 |
| 38.788 | 2.3197 | 6.4 |

Example 20

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form G Methyl Isobutyl Ketone Isomorphic Solvate MIBK (400 µL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (50 mg), and the suspension was stirred at room temperature overnight. The solids were filtered and dried to yield Form G Methyl Isobutyl Ketone.

The XRPD scan is shown in FIG. 20 and the peak assignments are in Table 20:

TABLE 20

| 2θ | d (Å) | Relative Intensity |
|---|---|---|
| 4.824 | 18.302 | 12.3 |
| 5.638 | 15.6616 | 26.6 |
| 7.78 | 11.3544 | 95.5 |
| 8.217 | 10.7513 | 58.1 |
| 9.298 | 9.5039 | 50.4 |
| 11.239 | 7.8665 | 72.1 |
| 11.515 | 7.6787 | 13.8 |
| 12.341 | 7.1661 | 46.1 |
| 12.575 | 7.0334 | 46.9 |
| 13.079 | 6.7636 | 50.2 |
| 13.437 | 6.5842 | 19 |
| 14.338 | 6.1723 | 16.4 |
| 15.715 | 5.6346 | 16.1 |
| 16.221 | 5.4599 | 29.8 |
| 16.503 | 5.3672 | 69.4 |
| 16.993 | 5.2135 | 28.4 |
| 17.415 | 5.0881 | 25.4 |
| 17.961 | 4.9347 | 29.2 |
| 18.503 | 4.7914 | 32.5 |
| 19.036 | 4.6585 | 24.8 |
| 19.35 | 4.5835 | 21.3 |
| 19.66 | 4.512 | 22.7 |
| 19.858 | 4.4674 | 52 |
| 20.52 | 4.3247 | 24 |
| 21.221 | 4.1834 | 27.4 |
| 21.442 | 4.1408 | 50 |
| 21.641 | 4.1032 | 28.3 |
| 22.305 | 3.9825 | 25.8 |
| 22.644 | 3.9236 | 16.1 |
| 23.28 | 3.8178 | 100 |
| 23.619 | 3.7637 | 46.7 |
| 24.562 | 3.6214 | 56.6 |
| 24.997 | 3.5593 | 23.7 |
| 27.477 | 3.2435 | 27.1 |
| 27.759 | 3.2111 | 50.5 |
| 28.302 | 3.1508 | 23.6 |
| 29.898 | 2.9862 | 17.4 |
| 31.866 | 2.806 | 14.3 |
| 33.135 | 2.7014 | 10.4 |

Example 21

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form H MTBE (600 µL) was added to a vial containing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (90 mg), and the contents were stirred at room temperature overnight. The solids were filtered and dried at room temperature to yield Form H (Methyl tert-Butyl Ether solvate).

The XRPD scan is shown in FIG. 21 and the peak assignments are in Table 21:

TABLE 21

| 2θ | d (Å) | Relative Intensity |
|---|---|---|
| 7.38 | 11.9685 | 14.9 |
| 9.246 | 9.5576 | 11.1 |
| 11.18 | 7.908 | 100 |
| 12.701 | 6.9638 | 12.2 |
| 16.08 | 5.5075 | 55.8 |
| 18.696 | 4.7422 | 9.9 |
| 19.58 | 4.5302 | 30.1 |
| 22.04 | 4.0298 | 73.9 |
| 24.741 | 3.5955 | 21.7 |
| 25.501 | 3.4901 | 29.6 |
| 26.738 | 3.3314 | 13.3 |
| 27.86 | 3.1997 | 11.7 |
| 28.198 | 3.1621 | 7.5 |
| 31.901 | 2.803 | 7.3 |
| 33.618 | 2.6637 | 7.8 |

Example 22

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form I Xylene (600 μL) was added to a vial containing amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (90 mg), and the contents were stirred at room temperature overnight. The solids were filtered and dried at room temperature to yield Form I (Xylenes solvate).

The XRPD scan is shown in FIG. 22 and the peak assignments are in Table 22:

TABLE 22

| 2θ | d (Å) | Relative Intensity |
|---|---|---|
| 4.318 | 20.4483 | 11.8 |
| 7.2 | 12.268 | 100 |
| 8.065 | 10.9535 | 33.7 |
| 8.421 | 10.4921 | 19.4 |
| 9.603 | 9.2023 | 8.9 |
| 10.343 | 8.5459 | 34.1 |
| 11.101 | 7.9636 | 33.8 |
| 12.117 | 7.2984 | 37.7 |
| 12.664 | 6.9844 | 20.2 |
| 13.057 | 6.7751 | 17.4 |
| 14.961 | 5.9169 | 22.7 |
| 15.222 | 5.816 | 28.1 |
| 16.319 | 5.4272 | 35.3 |
| 16.559 | 5.3491 | 64.2 |
| 16.798 | 5.2735 | 27.6 |
| 17.578 | 5.0414 | 19.1 |
| 18.303 | 4.8434 | 59.5 |
| 18.904 | 4.6907 | 24.3 |
| 19.32 | 4.5905 | 39.8 |
| 19.54 | 4.5394 | 39.6 |
| 20.261 | 4.3794 | 33.3 |
| 20.641 | 4.2997 | 35.9 |
| 21.082 | 4.2107 | 27.8 |
| 22.282 | 3.9866 | 40.3 |
| 23.101 | 3.8471 | 44 |
| 23.942 | 3.7137 | 21.6 |
| 25.134 | 3.5403 | 7.6 |
| 25.541 | 3.4847 | 20.7 |
| 26.341 | 3.3807 | 27.7 |
| 27.198 | 3.2761 | 9.2 |
| 27.395 | 3.2529 | 9.6 |
| 27.667 | 3.2216 | 7.4 |
| 29.58 | 3.0174 | 9.7 |

Example 23

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form J 2-Methoxyethanol (4 mL) was added to a 20 mL scint vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (1013.25 mg), and the contents were stirred at room temperature for about 6 hours. The contents were filtered and washed with 2-methoxyethanol (2×10 mL). The solids were dried on the filter at room temperature for about 1 hour to yield Form J (2-Methoxyethanol solvate).

The XRPD scan is shown in FIG. 23 and the peak assignments are in Table 23:

TABLE 23

| 2θ | d (Å) | Relative Intensity |
|---|---|---|
| 4.019 | 21.9675 | 4.5 |
| 4.479 | 19.7134 | 53.2 |
| 6.777 | 13.0322 | 25.4 |
| 8.982 | 9.838 | 49.8 |
| 10.358 | 8.5335 | 3.2 |
| 11.874 | 7.4469 | 2.4 |
| 12.083 | 7.319 | 4.5 |
| 12.724 | 6.9517 | 18.9 |
| 13.521 | 6.5434 | 29.6 |
| 14.463 | 6.1192 | 4.7 |
| 15.014 | 5.896 | 6.2 |
| 16.963 | 5.2228 | 100 |
| 18.078 | 4.903 | 88.2 |
| 18.797 | 4.7169 | 39.4 |
| 19.317 | 4.5912 | 11.4 |
| 19.858 | 4.4673 | 32.5 |
| 20.156 | 4.4019 | 25.4 |
| 20.838 | 4.2595 | 23.3 |
| 21.761 | 4.0808 | 31.2 |
| 22.118 | 4.0158 | 9.4 |
| 22.682 | 3.9171 | 12.9 |
| 23.298 | 3.8149 | 19 |
| 24.062 | 3.6955 | 15.2 |
| 24.658 | 3.6076 | 16.7 |
| 24.957 | 3.5649 | 16.9 |
| 25.664 | 3.4683 | 21.4 |
| 26.167 | 3.4028 | 6.4 |
| 26.734 | 3.3319 | 6 |
| 26.998 | 3.2999 | 4.1 |
| 27.299 | 3.2642 | 16.3 |
| 27.497 | 3.2411 | 9.8 |
| 27.638 | 3.2249 | 6.9 |
| 28.779 | 3.0996 | 2.7 |
| 30.02 | 2.9742 | 4.9 |
| 31.106 | 2.8729 | 3.1 |
| 32.043 | 2.791 | 10.5 |
| 33.279 | 2.69 | 4.5 |
| 33.604 | 2.6648 | 4.6 |
| 34.407 | 2.6044 | 4.4 |
| 35.097 | 2.5548 | 3.2 |
| 36.444 | 2.4634 | 4.4 |
| 36.655 | 2.4497 | 2.8 |
| 37.891 | 2.3726 | 2.2 |
| 38.179 | 2.3553 | 2.9 |
| 38.459 | 2.3388 | 2.3 |
| 39.413 | 2.2844 | 2.2 |

Example 24

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form K DME (4 mL) was added to a 20 mL scint vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (939.4 mg), and the contents were stirred at room temperature for about 6 hours. The contents were filtered and washed with DME (2×10 mL). The solids were dried at 50° C. under vacuum overnight to yield Form K (Dimethoxyethane solvate).

The XRPD scan is shown in FIG. 24 and the peak assignments are in Table 24:

TABLE 24

| 2θ | d (Å) | Relative Intensity |
|---|---|---|
| 6.923 | 12.7574 | 32.9 |
| 8.499 | 10.3956 | 8.4 |

TABLE 24-continued

| 2θ | d (Å) | Relative Intensity |
|---|---|---|
| 10.137 | 8.7186 | 3.2 |
| 11.036 | 8.011 | 12.5 |
| 11.836 | 7.4712 | 28.8 |
| 12.054 | 7.3363 | 4.3 |
| 12.743 | 6.9411 | 10.2 |
| 13.259 | 6.6723 | 5.8 |
| 13.923 | 6.3553 | 38.8 |
| 14.775 | 5.9908 | 10.3 |
| 15.797 | 5.6056 | 62.7 |
| 16.96 | 5.2237 | 20.8 |
| 17.16 | 5.1632 | 31.8 |
| 17.62 | 5.0293 | 58.8 |
| 17.998 | 4.9246 | 34.6 |
| 18.482 | 4.7967 | 3.2 |
| 18.683 | 4.7455 | 8 |
| 18.999 | 4.6673 | 39.5 |
| 21.041 | 4.2187 | 4.9 |
| 21.24 | 4.1797 | 9.2 |
| 21.796 | 4.0744 | 4.8 |
| 21.898 | 4.0555 | 4.7 |
| 22.177 | 4.0051 | 4.5 |
| 22.78 | 3.9005 | 100 |
| 23 | 3.8638 | 77.9 |
| 23.336 | 3.8088 | 3.8 |
| 23.863 | 3.7259 | 3.6 |
| 24.205 | 3.674 | 7.1 |
| 24.503 | 3.63 | 8.2 |
| 25.269 | 3.5217 | 4.2 |
| 25.701 | 3.4635 | 42.8 |
| 27.101 | 3.2876 | 27.3 |
| 28.26 | 3.1554 | 6 |
| 28.821 | 3.0952 | 5.8 |
| 29.258 | 3.0499 | 4.2 |
| 29.441 | 3.0314 | 6.6 |
| 29.864 | 2.9894 | 4.5 |
| 30.444 | 2.9338 | 5.6 |
| 30.749 | 2.9054 | 2.5 |
| 31.942 | 2.7995 | 5.5 |
| 32.94 | 2.7169 | 2.8 |
| 33.864 | 2.6449 | 4.3 |
| 35.505 | 2.5264 | 2.3 |
| 36.018 | 2.4915 | 3.3 |
| 37.375 | 2.4041 | 2.3 |
| 38.245 | 2.3514 | 2.3 |
| 38.876 | 2.3147 | 2.4 |
| 39.333 | 2.2888 | 2.4 |

Example 25

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form L MeOAc (400 μL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form E (50 mg), and the contents were stirred overnight at room temperature. The solids were filtered and dried to yield Form L (Methyl Acetate solvate).

The XRPD scan is shown in FIG. 25 and the peak assignments are in Table 25:

TABLE 25

| 2θ | d (Å) | Relative Intensity |
|---|---|---|
| 5.028 | 17.5604 | 5.3 |
| 6.978 | 12.657 | 10.4 |
| 7.602 | 11.6193 | 13.4 |
| 8.301 | 10.6435 | 15.1 |

TABLE 25-continued

| 2θ | d (Å) | Relative Intensity |
|---|---|---|
| 9.34 | 9.4614 | 5.5 |
| 9.638 | 9.1691 | 3.5 |
| 11.523 | 7.673 | 22.9 |
| 12.281 | 7.2015 | 3.5 |
| 12.758 | 6.9332 | 20.1 |
| 14.899 | 5.9414 | 64.5 |
| 15.463 | 5.7257 | 10.4 |
| 16.198 | 5.4675 | 12.2 |
| 16.98 | 5.2176 | 100 |
| 17.521 | 5.0575 | 9.1 |
| 18.478 | 4.7978 | 12.7 |
| 18.958 | 4.6773 | 89.8 |
| 19.62 | 4.5211 | 27.2 |
| 20.822 | 4.2627 | 16.4 |
| 21.062 | 4.2147 | 37.3 |
| 21.462 | 4.137 | 20.3 |
| 22.122 | 4.015 | 9.2 |
| 22.457 | 3.9558 | 47.9 |
| 23.019 | 3.8606 | 15.7 |
| 23.661 | 3.7572 | 7.4 |
| 24.126 | 3.6859 | 7.3 |
| 24.6 | 3.6159 | 16.9 |
| 25.7 | 3.4636 | 16.9 |
| 26.311 | 3.3845 | 7.2 |
| 27.183 | 3.2779 | 17.1 |
| 27.819 | 3.2044 | 11.7 |
| 28.64 | 3.1144 | 12.5 |
| 29.736 | 3.002 | 6.2 |
| 30.939 | 2.888 | 5.1 |
| 31.197 | 2.8647 | 4.3 |
| 32.037 | 2.7915 | 5.7 |
| 32.379 | 2.7627 | 6.1 |
| 32.742 | 2.7329 | 4.9 |
| 33.764 | 2.6525 | 4.5 |
| 35.919 | 2.4981 | 3.8 |
| 38.746 | 2.3222 | 3.3 |

Example 26

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form M THF:water (0.4 mL, 1:1) was added to a flask containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol (50 mg), and the contents were stirred for 24 hours at room temperature. The solids were filtered and dried at room temperature to yield Form M (Tetrahydrofuran:Water solvate) (86% yield).

The XRPD scan is shown in FIG. 26 and the peak assignments are in Table 26:

TABLE 26

| 2θ | d (Å) | Relative Intensity |
|---|---|---|
| 8.982 | 9.8379 | 100 |
| 10.375 | 8.5192 | 24.7 |
| 11.194 | 7.8982 | 4.2 |
| 13.379 | 6.6124 | 13.3 |
| 14.422 | 6.1366 | 7.7 |
| 15.136 | 5.8487 | 34.5 |
| 15.561 | 5.6899 | 26.3 |
| 16.057 | 5.5153 | 8.5 |
| 16.255 | 5.4484 | 10.3 |
| 17.009 | 5.2086 | 3.6 |
| 17.383 | 5.0975 | 3.7 |
| 17.859 | 4.9625 | 7.4 |
| 18.201 | 4.8702 | 23.4 |

TABLE 26-continued

| 2θ | d (Å) | Relative Intensity |
|---|---|---|
| 18.54 | 4.7819 | 7.5 |
| 18.819 | 4.7115 | 7.8 |
| 20.738 | 4.2798 | 47.8 |
| 21.395 | 4.1497 | 21.8 |
| 22.583 | 3.9341 | 15.8 |
| 23.083 | 3.8501 | 68.1 |
| 23.455 | 3.7897 | 13.6 |
| 23.863 | 3.7259 | 3.6 |
| 24.419 | 3.6422 | 4.4 |
| 24.715 | 3.5993 | 4.2 |
| 24.943 | 3.5669 | 4.9 |
| 25.438 | 3.4987 | 3.3 |
| 25.822 | 3.4474 | 3.8 |
| 26.44 | 3.3683 | 5.2 |
| 26.76 | 3.3287 | 29.9 |
| 27.301 | 3.2639 | 6.8 |
| 28.126 | 3.17 | 2.9 |
| 29.178 | 3.0581 | 6 |
| 29.459 | 3.0296 | 13.8 |
| 30.543 | 2.9245 | 8.5 |
| 32.507 | 2.7522 | 3.1 |
| 34.461 | 2.6005 | 3.3 |

Example 27

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form N A solution of 1% NaCMC and 0.1% Tween® in water (2 mL) was added to a vial containing N4-(4-([1,2,4]triazolo[1,5-c]pyridin-7-yloxy)-3-methylphenyl)-N6-(4,4-dimethyl-4,5-dihydrooxazol-2-yl)quinazoline-4,6-diamine Form B Ethanol (51.26 mg). The vial was placed on a stir plate and allowed to stir for 2 weeks at room temperature. Solids were collected by filtration and washed with water (2×3 mL). The solids were collected and dried under vacuum at room temperature overnight to yield Form N (Hydrate).

The XRPD scan is shown in FIG. 27 and the peak assignments are in Table 27:

TABLE 27

| 2θ | d (Å) | Relative Intensity |
|---|---|---|
| 7.04 | 12.5463 | 33.6 |
| 8.142 | 10.8505 | 9.2 |
| 8.521 | 10.3682 | 15.6 |
| 8.902 | 9.9256 | 6.9 |
| 10.238 | 8.6335 | 8.5 |
| 11.16 | 7.9217 | 14.5 |
| 11.941 | 7.4055 | 29 |
| 12.918 | 6.8476 | 9.5 |
| 13.36 | 6.6221 | 7.4 |
| 14.02 | 6.3115 | 36.9 |
| 14.903 | 5.9398 | 9.6 |
| 15.88 | 5.5764 | 66.7 |
| 17.378 | 5.0988 | 32.6 |
| 17.759 | 4.9903 | 53.9 |
| 18.08 | 4.9025 | 35.3 |
| 19.202 | 4.6185 | 40.1 |
| 21.302 | 4.1676 | 11.2 |
| 21.895 | 4.0561 | 3.6 |
| 22.92 | 3.877 | 100 |
| 24.074 | 3.6937 | 4.8 |
| 24.701 | 3.6013 | 10.9 |
| 25.881 | 3.4398 | 41.7 |
| 27.319 | 3.2618 | 29.9 |

TABLE 27-continued

| 2θ | d (Å) | Relative Intensity |
|---|---|---|
| 28.401 | 3.14 | 8.5 |
| 28.999 | 3.0766 | 5.5 |
| 29.539 | 3.0216 | 6 |
| 30.041 | 2.9722 | 4.9 |
| 30.578 | 2.9213 | 5.8 |
| 32.138 | 2.7829 | 5 |
| 33.081 | 2.7057 | 5.1 |
| 34.001 | 2.6346 | 4.7 |
| 35.623 | 2.5183 | 3.8 |
| 36.195 | 2.4797 | 4.8 |
| 37.291 | 2.4093 | 2.3 |

Example 28

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form O THF (40 g) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G hemi-Tetrahydrofuran (3 g), and the contents were agitated at 50° C. The contents were filtered and washed with THF (3×6 mL). Solids were dried in a vacuum oven at 45° C. with a nitrogen bleed to yield Form O (Anhydrous) (45% yield).

The XRPD scan is shown in FIG. 28 and the peak assignments are in Table 28:

TABLE 28

| 2θ | d (Å) | Relative Intensity |
|---|---|---|
| 8.161 | 10.825 | 10.4 |
| 8.875 | 9.9558 | 6 |
| 9.361 | 9.4402 | 4.7 |
| 9.96 | 8.8737 | 3.5 |
| 10.522 | 8.4007 | 9.9 |
| 11.238 | 7.8669 | 100 |
| 12.722 | 6.9528 | 6.4 |
| 13.541 | 6.534 | 10.6 |
| 15.043 | 5.8845 | 7.4 |
| 15.544 | 5.6961 | 8.7 |
| 16.079 | 5.5079 | 21 |
| 16.52 | 5.3618 | 41 |
| 17.63 | 5.0266 | 5.6 |
| 18.701 | 4.741 | 6.7 |
| 19.198 | 4.6193 | 9.3 |
| 19.98 | 4.4404 | 36.8 |
| 21.243 | 4.1791 | 6.8 |
| 22.179 | 4.0048 | 59.7 |
| 22.677 | 3.9179 | 19.2 |
| 23.141 | 3.8405 | 20.9 |
| 24.86 | 3.5786 | 18.7 |
| 25.638 | 3.4718 | 25.8 |
| 26.861 | 3.3164 | 8.1 |
| 27.979 | 3.1864 | 10.1 |
| 28.376 | 3.1427 | 4.7 |
| 30.583 | 2.9208 | 6 |
| 31.917 | 2.8017 | 4.5 |
| 32.657 | 2.7398 | 2.2 |
| 33.861 | 2.6451 | 5.3 |

Example 29

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form P Water (12 mL) was added to a vial containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form G Tetrahydrofuran (1.5 g), and the contents were agitated at room temperature. The contents were filtered and washed with THF:water (1:2.2 v/v. 7.2 mL) and water (7.2 mL). The wet cake was dried in a vacuum oven at 55° C. with a nitrogen bleed to yield Form P (Anhydrous) (81% yield).

The XRPD scan is shown in FIG. 29 and the peak assignments are in Table 29:

TABLE 29

| 2θ | d (Å) | Relative Intensity |
|---|---|---|
| 6.962 | 12.687 | 5.1 |
| 9.901 | 8.9266 | 38.5 |
| 11.043 | 8.0059 | 25.4 |
| 11.422 | 7.7411 | 1.4 |
| 12.48 | 7.0867 | 1.7 |
| 13.123 | 6.7412 | 6.9 |
| 13.74 | 6.4396 | 28.6 |
| 14.577 | 6.0716 | 10.9 |
| 15.403 | 5.7481 | 20.5 |
| 15.662 | 5.6536 | 48.4 |
| 16.424 | 5.3929 | 13.9 |
| 17.661 | 5.0179 | 32 |
| 18.777 | 4.7221 | 6.7 |
| 19.92 | 4.4537 | 8.1 |
| 20.541 | 4.3204 | 22.4 |
| 21.684 | 4.0951 | 4.3 |
| 22.14 | 4.0118 | 11.7 |
| 23.04 | 3.857 | 14.6 |
| 23.5 | 3.7826 | 100 |
| 24.271 | 3.6641 | 1.8 |
| 24.76 | 3.5929 | 17.9 |
| 25.359 | 3.5093 | 8.3 |
| 26.982 | 3.3018 | 10.3 |
| 27.619 | 3.2271 | 11.9 |
| 28.419 | 3.138 | 5.2 |
| 29.022 | 3.0742 | 6.1 |
| 29.923 | 2.9837 | 9.1 |
| 30.781 | 2.9024 | 6.3 |
| 31.72 | 2.8186 | 4.6 |
| 32.044 | 2.7909 | 3 |
| 32.314 | 2.7682 | 2.2 |
| 33.441 | 2.6774 | 3.2 |
| 34.377 | 2.6066 | 5.8 |
| 35.815 | 2.5052 | 2.6 |
| 36.376 | 2.4678 | 3.4 |
| 37.083 | 2.4224 | 2.1 |
| 38.365 | 2.3443 | 1.8 |
| 38.827 | 2.3175 | 2.1 |
| 39.437 | 2.283 | 3.1 |

Example 30

Amorphous N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine Form B Ethanol (402 mg) was added to a vial containing 3:7 water:THF (40 mL). The solution was sonicated and stirred until all the solids were dissolved. The solution was then frozen in a dry ice/acetone bath (4 hours) and lyophilized over a period of 48 hours to yield an amorphous powder.

The XRPD scan is shown in FIG. 30.

Example 31

Pharmaceutical Composition

A pharmaceutical composition may be prepared by forming a powder in capsule ("PIC") composition containing 25 mg or 100 mg of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine from Examples 1 to 30. The PIC composition may be prepared in size 00 white opaque hard gelatin capsules.

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating a disease or disorder modulated by ErbB2, comprising administering to a mammal in need of such treatment an effective amount of a crystalline polymorph of N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine freebase, wherein the disease or disorder modulated by ErbB2 is breast cancer, and wherein the polymorph is selected from the group consisting of Form C, Form D, Form, E, Form F, Form G, Form H, Form I, Form J, Form K, Form L, Form M, Form N, Form O and Form P.

2. The method of claim 1, wherein the breast cancer is ErbB2 positive.

3. The method of claim 1, wherein one or more additional compounds having anti-cancer properties are administered in combination.

4. The method of claim 1, wherein the polymorph is selected from the group consisting of Form C, Form G, Form M, Form O and Form P.

5. The method of claim 4, wherein the cancer is ErbB2 positive.

6. The method of claim 4, wherein one or more additional compounds having anti-cancer properties are administered in combination.

7. The method of claim 4, wherein said polymorph has an XRPD pattern substantially the same as FIG. 10.

8. The method of claim 4, wherein said polymorph is characterized by at least one specific XRPD diffraction peak (2θ degrees ±0.2) at about 5.0.

9. The method of claim 1, wherein said polymorph has an XRPD pattern substantially the same as FIG. 17.

10. The method of claim 1, wherein said polymorph is characterized by at least one specific XRPD diffraction peak (2θ degrees ±0.2) at about 7.7, 11.1, 12.3, 23.1 and 24.1.

11. The method of claim 1, wherein said polymorph has an XRPD pattern substantially the same as FIG. 18.

12. The method of claim 1, wherein said polymorph is characterized by at least one specific XRPD diffraction peak (2θ degrees ±0.2) at about 7.7, 11.1, 12.4, 23.0 and 24.0.

13. The method of claim 1, wherein said polymorph has an XRPD pattern substantially the same as FIG. 19.

14. The method of claim 1, wherein said polymorph is characterized by at least one specific XRPD diffraction peak (2θ degrees ±0.2) at about 7.8, 8.3, 11.4, 13.2 and 23.4.

15. The method of claim 1, wherein said polymorph has an XRPD pattern substantially the same as FIG. 20.

16. The method of claim 1, wherein said polymorph is characterized by at least one specific XRPD diffraction peak (2θ degrees ±0.2) at about 7.8, 8.2, 11.2, 16.5 and 23.2.

17. The method of claim 1, wherein said polymorph has an XRPD pattern substantially the same as FIG. 26.

18. The method of claim 1, wherein said polymorph is characterized by at least one specific XRPD diffraction peak (2θ degrees ±0.2) at about 9.0.

19. The method of claim 1, wherein said polymorph has an XRPD pattern substantially the same as FIG. 28.

20. The method of claim 1, wherein said polymorph is characterized by at least one specific XRPD diffraction peak (2θ degrees ±0.2) at about 11.2.

21. The method of claim 1, wherein said polymorph has an XRPD pattern substantially the same as FIG. 29.

22. The method of claim 1, wherein said polymorph is characterized by at least one specific XRPD diffraction peak (2θ degrees ±0.2) at about 23.5.

23. The method of claim 4, wherein said polymorph has an XRPD pattern substantially the same as FIG. 17.

24. The method of claim 4, wherein said polymorph is characterized by at least one specific XRPD diffraction peak (2θ degrees ±0.2) at about 7.7, 11.1, 12.3, 23.1 and 24.1.

25. The method of claim 4, wherein said polymorph has an XRPD pattern substantially the same as FIG. 18.

26. The method of claim 4, wherein said polymorph is characterized by at least one specific XRPD diffraction peak (2θ degrees ±0.2) at about 7.7, 11.1, 12.4, 23.0 and 24.0.

27. The method of claim 4, wherein said polymorph has an XRPD pattern substantially the same as FIG. 19.

28. The method of claim 4, wherein said polymorph is characterized by at least one specific XRPD diffraction peak (2θ degrees ±0.2) at about 7.8, 8.3, 11.4, 13.2 and 23.4.

29. The method of claim 4, wherein said polymorph has an XRPD pattern substantially the same as FIG. 20.

30. The method of claim 4, wherein said polymorph is characterized by at least one specific XRPD diffraction peak (2θ degrees ±0.2) at about 7.8, 8.2, 11.2, 16.5 and 23.2.

31. The method of claim 4, wherein said polymorph has an XRPD pattern substantially the same as FIG. 26.

32. The method of claim 4, wherein said polymorph is characterized by at least one specific XRPD diffraction peak (2θ degrees ±0.2) at about 9.0.

33. The method of claim 4, wherein said polymorph has an XRPD pattern substantially the same as FIG. 28.

34. The method of claim 4, wherein said polymorph is characterized by at least one specific XRPD diffraction peak (2θ degrees ±0.2) at about 11.2.

35. The method of claim 4, wherein said polymorph has an XRPD pattern substantially the same as FIG. 29.

36. The method of claim 4, wherein said polymorph is characterized by at least one specific XRPD diffraction peak (2θ degrees ±0.2) at about 23.5.

* * * * *